US006380376B1

(12) United States Patent
Paul et al.

(10) Patent No.: US 6,380,376 B1
(45) Date of Patent: Apr. 30, 2002

(54) PROTEINS ENCODED BY POLYNUCLEIC ACIDS OF PORCINE REPRODUCTIVE AND RESPIRATORY SYNDROME VIRUS (PRRSV)

(75) Inventors: Prem S. Paul, Ames, IA (US); Yanjin Zhang, San Antonio, TX (US)

(73) Assignee: Iowa State University Research Foundation, Ames, IA (US)

( * ) Notice: Subject to any disclaimer, the term of this patent is extended or adjusted under 35 U.S.C. 154(b) by 0 days.

(21) Appl. No.: 09/019,793

(22) Filed: Feb. 6, 1998

Related U.S. Application Data

(63) Continuation-in-part of application No. 08/478,316, filed on Jun. 7, 1995, now Pat. No. 6,251,397, which is a continuation-in-part of application No. 08/301,435, filed on Sep. 1, 1994, which is a continuation-in-part of application No. 08/131,625, filed on Oct. 5, 1993, now Pat. No. 5,695,766, which is a continuation-in-part of application No. 07/969,071, filed on Oct. 30, 1992, now abandoned.

(51) Int. Cl.$^7$ ............................................... C07H 21/00
(52) U.S. Cl. ......................................... 536/23.72; 435/5
(58) Field of Search ........................... 536/23.72; 435/5

(56) References Cited

U.S. PATENT DOCUMENTS 5,695,766 A   12/1997   Paul et al.

FOREIGN PATENT DOCUMENTS

| EP | 0 595 436 | 5/1994 |
|---|---|---|
| WO | WO 96/06619 | 3/1996 |
| WO | WO 96/40932 | 12/1996 |

OTHER PUBLICATIONS

Weiland et al., Monoclonal antibodies to the GP5 of porcine reproductive and respiratory syndrome virus are more effective in virus neutralization than monoclonal antibodies to the GP4. Veterinary Microbiology 66:171–186, 1999.*

V. Kapur, et al. Journal of General Virology, vol. 77, pp. 1271–1276, "Genetic Variation in Porcine Reproductive and Respiratory Syndrome Virus Isolates in the Midwestern United States", 1996.

X.–J. Meng et al., *Arch Virol.* (1995) 140:745–55, Springer–Verlag, Austria.

X.–J. Meng et al., *J. Gen. Virol.* (1995) 76:3181–88, Society of General Microbiology, Great Britain.

* cited by examiner

*Primary Examiner*—Donna C. Wortman
(74) *Attorney, Agent, or Firm*—Oblon, Spivak, McClelland, Maier & Neustadt, P.C.

(57) ABSTRACT

The present invention provides a purified preparation containing, for example, at least one polypeptide selected from the group consisting of proteins encoded by one or more open reading frames (ORF's) of an Iowa strain of porcine reproductive and respiratory syndrome virus (PRRSV), antigenic regions of such proteins which are at least 5 amino acids in length and which effectively protect a porcine host against a subsequent challenge with a PRRSV isolate, and combinations thereof in which amino acids non-essential for antigenicity may be conservatively substituted. The present invention also concerns a vaccine comprising an effective amount of such a protein; antibodies which specifically bind to such a protein; methods of producing the same; and methods of protecting a pig against a PRRSV, treating a pig infected by a PRRSV, and detecting PRRSV in a pig.

6 Claims, 28 Drawing Sheets

```
                                              +1>ORF2
VR2385   CCTGTCATTGAACCAACTTTAGGCCTGAATTGAGATGAAATGGGGTCTATGCAAAGCCTT   60
ISU3927  ...A................G..T..AG.C...A...C.........C...........   60
ISU55    ...A..........................A............................   60
ISU22    ..............................A..........G.C...............   60
VR2332   ..............................A............C...............   60
ISU1894  ..C...........................A............CG..............   60
ISU79    ..............................A............C...............   60

VR2385   TTTGACAAAATTGGCCAACTTTTTGTGGATGCTTTCACGGAGTTCTTGGTGTCCATTGTT   120
ISU3927  ........G..C..T.............................................   120
ISU55    ..................C.........................................   120
ISU22    ............................................................   120
VR2332   ............................................................   120
ISU1894  ............................................................   120
ISU79    ............................................................   120

VR2385   GATATCATTATATTTTTGGCCATTTTGTTTGGCTTCACCATCGCAGGTTGGCTGGTGGTC   180
ISU2927  .........C...........................T..C..C...............   180
ISU55    ..........................................C.................   180
ISU22    ..........................................C.................   180
VR2332   ..........................................C.................   180
ISU1894  .........C................................C.................   180
ISU79    ...........C..............................C.................   180

VR2385   TTTTGCATCAGATTGGTTTGCTCCGCGATACTCCGTGCGCGCCCTGCCATTCACTCTGAG   240
ISU3297  ..................................................C.........   240
ISU55    ..................C..........................................   240
ISU22    .............................................................   240
VR2332   ..................................A..........................   240
ISU1894  ..................................A..........................   240
ISU79    ..................................A..........................   240

VR2385   CAATTACAGAAGATCCTATGAGGCCTTTCTCTCTCAGTGCCAGGTGGACATTCCCACCTG   300
ISU3297  ............................T....................G...........   300
ISU55    ............................T..................................   300
ISU22    ...................T........T..C.....A..........................   300
VR2332   ...................T........T..C.....A..........................   300
ISU1894  ...................T.........T.A..C....A..........................   300
ISU79    ...................T........T..C.....A..........................   300

VR2385   GGGAACTAAACATCCTTTGGGGATGCTTTGGCACCATAAGGTGTCAACCCTGATTGATGA   360
ISU3927  ......A.G........A....................C.......................   360
ISU55    .....T...............T...........................................   360
ISU22    ....................T.G..........................................   360
VR2332   ..................................................................   360
ISU1894  .....................T............................................   360
ISU79    .....................T............................................   360
```

FIG.1A

```
VR2385   AATGGTGTCGCGTCGAATGTACCGCATCATGGAAAAAGCAGGACAGGCTGCCTGGAAACA   420
ISU3927  ............................................................   420
ISU55    ............................................................   420
ISU22    ...........................................G................   420
VR2332   ...........................................G................   420
ISU1894  ............C..............................G................   420
ISU79    G...........................................................   420

VR2385   GGTAGTGAGCGAGGCTACGCTGTCTCGCATTAGTAGTTTGGATGTGGTGGCTCATTTTCA   480
ISU3927  ...G.....T................G...........................C....   480
ISU55    ...G...................................................C....   480
ISU22    ...G...................................................C....   480
VR2332   ...G.........................................................   480
ISU1894  ...G........................C.................................  480
ISU79    ...G..........................................................  480

VR2385   GCATCTTGCCGCCATTGAAGCCGAGACCTGTAAATATCTGGCCTCTCGGCTGCCCATGCT   540
ISU3927  ...C..........................T..........T............T....   540
ISU55    ..........................................T.................   540
ISU22    ........T.................................T......C..........   540
VR2332   .....A....................................T......C..........   540
ISU1894  ..........................................T......C..........   540
ISU79    ............C.............................T......C..........   540
                                             -89(mRNA3)
VR2385   ACACCACCTGCGCATGACAGGGTCAAATGTAACCATAGTGTATAATAGTACTTTGAATCA   600
ISU3927  ....A......T..T................_____..........C............   600
ISU55    ....A.........................._____.........................   600
ISU22    ....A.........................._____.........................   600
VR2332   ....A.........................._____...............C.........   600
ISU1894  ...TA........A................._____.................C.G.G..   600
ISU79    ....A.........................._____..........................G   600
                                                                    +1>
VR2385   GGTGTTTGCTGTTTTCCCAACCCCTGGTTCCCGGCCAAAGCTTCATGATTTCCAGCAATG   660
ISU3927  .........A...........C.....T..........C..........T...........   660
ISU55    ....C....A....................................T...............   660
ISU22    .........A....................................T...............   660
VR2332   .........A....T...............................T...............   660
ISU1894  .........A....................................T...............   660
ISU79    .........A..................................C..T...............   660
         ORF3
VR2385   GCTAATAGCTGTACATTCCTCTATATTTTCCTCTGTTGCAGCTTCTTGTACTCTTTTTGT   720
ISU3927  ....................C....CC..................................   720
ISU55    ..............................................................   720
ISU22    .T.................C......................C....................   720
VR2332   .T.................C............................................  720
ISU1894  .T.................C............................................  720
ISU79    ..........G........C................................C..........   720
```

FIG. 1B

```
VR2385   TGTGCTGTGGTTGCGGGTTCCAATGCTACGTACTGTTTTTGGTTTCCGCTGGTTAGGGGC  780
ISU3927  ....T......A...A.G............T.............................  780
ISU55    ...........................T..C.............................  780
VR2385   ............................................................  780
ISU22    ........................A.....T.............................  780
VR2332   ........................A...................................  780
ISU1894  .....C.....................................................G  780
ISU79    ........................A...................................  780
                              **<ORF2
VR2385   AATTTTTCTTTCGAACTCACGGTGAATTACACGGTGTGCCCGCCTTGCCTCACCCGGCAA  840
ISU3927  ......C.....G....T....................A....................G  840
ISU55    ..............A.....C..............T..A.....................  840
VR2385   ............................................................  840
ISU22    ..........G........................T..A.....................  840
VR2332   ..............A....................T..A.....................  840
ISU1894  .....C.....T.......................T..A.....................  840
ISU79    ..............TA..........A..................................  840
                               ***
VR2385   GCAGCCGCAGAGGCCTACGAACCCGGCAGGTCCCTTTGGTGCAGGATAGGGCATGATCGA  900
ISU3927  .......C..AT......AA.....T..............C...A................  900
ISU55    ......A...............T......T....................T........C  900
ISU22    ..........AT.........T......T.....................T.....C...  900
VR2332   ......A...AT.........T......T.....................T.....C...  900
ISU1894  ..........T..........T......T.....................T.....C...  900
ISU79    .....................T......T.....................T.C.......  900

VR2385   TGTGGGGAGGACGATCATGATGAACTAGGGTTTGTGGTGCCGTCTGGCCTCTCCAGCGAA  960
ISU3927  .....T.........C..C........A...ACA..A....C..........AA...    960
ISU55    ...............C............................................  960
ISU22    ...............C..G.........A....A...AC.....T...............  960
VR2332   ...............C..G.........A....A.A...C....................  960
ISU1894  ...............C..G.........A....A.A...C....................  960
ISU79    .....A......C....C..G........A....A.A........................  960
           -236(mRNA3-1)
VR2385   GGCCACTTGACCAGTGCTTACGCCTGGTTGGCGTCCCTGTCCTTCAGCTATACGGCCCAG  1020
ISU3927  .T...T_____....T.............TT........T..C.................  1020
ISU55    ...........____...T..................T....T....T..C..A......  1020
ISU22    ...........T....T...................TTT...........C.........  1020
VR2332   ...........TG...T..................T.T............C.........  1020
ISU1894  ...........T....T...................TTT...........C.........  1020
ISU79    ...........___..T..................T.T............C.........  1020
                                                      +1>ORF4-1
VR2385   TTCCATCCCGAGATATTCGGGATAGGGAATGTGAGTCGAGTCTATGTTGACATCAAGCAC  1080
ISU3927  ..T............A......AAG......_____..........T..T          1080
ISU55    ......T..................A...T._____..........G...T         1080
ISU22    .................C.............T._____..........A..T         1080
VR2332   ................................T._____..........A..T       1080
ISU1894  ................................T._____..........A..T       1080
ISU79    .....C..........................T._____..........A..T       1080
```

FIG. 1C

```
VR2385   CAATTCATTTGCGCTGTTCATGATGGGCAGAACACCACCTTGCCCCACCATGACAACATT  1140
ISU3927  ...C.......T.........C...........................T.G........  1140
ISU55    ............C.....C..C..........G....T.....T.G.........T...  1140
ISU22    ...C....C.....C..AA.....C........A..............T.GT........  1140
VR2332   ...C....C.....C..AA.....C...........................T.GT....  1140
ISU1894  ...C.........C..AA......C...A......G................T.GT........T...  1140
ISU79    ...C....C.....C..AA.....C...........................T.GT............  1140
                                                              -10(mRNA4)
VR2385   TCAGCCGTGCTTCAGACCTATTACCAGCATCAGGTCGACGGGGGCAATTGGTTTCACCTA  1200
ISU3927  ..T......T.........A..C..A....T..T.....C....___...  1200
ISU55    .........T.C.....T........A.....A.........C............___...  1200
ISU22    ..........T..............A.....A..............T.....___...  1200
VR2332   ..........T..............A.....A...............C....___...  1200
ISU1894  ..........T..............A.....A........T..C........___...  1200
ISU79    ..G......T..............A.....A.................C...___...  1200
         +1>ORF4                                                  **
VR2385   GAATGGGTGCGTCCCTTCTTTTCCTCTTGGTTGGTTTTAAATGTCTCTTGGTTTCTCAGG  1260
ISU3927  ......C...................................G......C.........  1260
ISU55    ......C.....................................................  1260
ISU22    ......C.T...............A...................................  1260
VR2332   ......C.T...............G...................................  1260
ISU1894  ......C.T...............A..........................A........  1260
ISU79    ......C.................A...................................  1260
         *<ORF3-1
VR2385   CGTTCGCCTGCAAGCCATGTTTCAGTTCGAGTCTTTCAGACATCAAGACCAACACCACCG  1320
ISU3927  ............................................................  1320
ISU55    ..................................G.....T..................  1320
ISU22    ............A.....................G....T.T..................  1320
VR2332   ............A.....................G....T.T..................  1320
ISU1894  ............A.....C...............G....T.T............T....  1320
ISU79    ............A.....................G....T....................  1320

VR2385   CAGCGGCAGGCTTTGCTGTCCTCCAAGACATCAGTTGCCTTAGGCATCGCAACTCGGCCT  1380
ISU3927  .G..A...AAT..C.........G......G.C...........G........A..A  1380
ISU55    ....................................................T.......  1380
ISU22    .......A...................G..........................G........  1380
VR2332   .......A...............................................G........  1380
ISU1894  .......A.....................................................  1380
ISU79    .......A.....................................................  1380
                                                    ***<ORF3
VR2385   CTGAGGCGATTCGCAAAGTCCCTCAGTGCCGCACGGCGATAGGGACACCCGTGTATATCA  1440
ISU3927  ........T......A............................................  1440
ISU55    ........T......A........T..T...................A.......T.  1440
ISU22    ...............A............T..............................T.  1440
VR2332   ...............A............T............................G.T.  1440
ISU1894  ...............A............T..............................T.  1440
ISU79    ...............A............T.....................TA.......T.  1440
```

FIG. 1D

```
VR2385   CTGTCACAGCCAATGTTACCGATGAGAATTATTTGCATTCCTCTGATCTTCTCATGCTTT  1500
ISU3927  ..A...........A..A........C...........T.....................  1500
ISU55    ..G...........A.............................C...............  1500
ISU22    .CA...........G..A..............A....T....C.................  1500
VR2332   .CA...........G..A..............A....T....C.................  1500
ISU1894  .CA...........G..A..............A....T....C.................  1500
ISU79    .CA...........G..A....A.........A....T....C.............C...  1500

VR2385   CTTCTTGCCTTTTCTATGCTTCTGAGATGAGTGAAAAGGGATTTAAGGTGGTATTTGGCA  1560
ISU3927  .C.............C.....................G..........G...........  1560
ISU55    ...............C.................................A..........  1560
ISU22    ...............C..................................G.........  1560
VR2332   .............................................................  1560
ISU1894  ...............C..................................A.....C...  1560
ISU79    ...................................................G......T.  1560

VR2385   ATGTGTCAGGCATCGTGGCAGTGTGCGTCAACTTCACCAGTTACGTCCAACATGTCAAGG  1620
ISU3927  ..........C......T......A....T..T......C..T........C.......  1620
ISU55    .................T..............T......C....................  1620
ISU22    .................T......T...T..T......C..T...............G..  1620
VR2332   .................T......T...T..T......C....................  1620
ISU1894  .................T......T...T..T......C..................G..  1620
ISU79    .................T......T..T..T......C.....T.............G..  1620

VR2385   AATTTACCCAACGTTCCTTGGTAGTTGACCATGTGCGGCTGCTCCATTTCATGACGCCCG  1680
ISU3927  .G..........C.....A..G..C........................A..T.......  1680
ISU55    ............C...........C........................A..T.......  1680
ISU22    .G..........C........G..C...........T.............A..T.......  1680
VR2332   .G..........C...C....G..C...........T.............A..T.......  1680
ISU1894  .G..........C...C....G..C...........T.............A..T.......  1680
ISU79    .G..........C.....A..G..C.........................A..T.......  1680
                                                              ***<ORF4
VR2385   AGACCATGAGGTGGGCAACTGTTTTAGCCTGTCTTTTTACCATTCTGTTGGCAATTTGAA  1740
ISU3927  .A..T..........................CG...........................  1740
ISU55    ..................................G............C............  1740
ISU22    ..................................G..........................  1740
VR2332   ..................................G..........................  1740
ISU1894  .A................................G..........C...............  1740
ISU79    ....................C.............G.T.........................  1740
              +1>ORF5
VR2385   TGTTTAAGTATGTTGGGGAAATGCTTGACCGCGGGCTGTTGCTCGCAATTGCTTTTTTTA  1800
ISU3927  ............................................G..C..........G  1800
ISU55    ......................................A.......TC..........G  1800
ISU22    .....C..................................G..........C...G    1800
VR2332   .............A..........................G..........C...G    1800
ISU1894  ........................................G..........C...G    1800
ISU79    ..................T.....................G..........C...G    1800
```

FIG. 1E

```
VR2385    TGGTGTATCGTGCCGTCTTGTTTTGTTGCGCTCGTCAGCGCCAACGGGAACAGCGGCTCA    1860
ISU3927   ................TC...C...C..................AAC.G......---..C    1860
ISU55     ..................G..............C..........A.C.G..A.A....T    1860
ISU22     ....T...........TC......C..T.....C.........G.AAC.G....A....C    1860
VR2332    ................TC......C..T.....C..A......G.AACG.....A....C    1860
ISU1894   ................TC......C..T.....C..A......G..CC......A....C    1860
ISU79     ................TC.....AC..T.....C.GA....C..A.C......A....T    1860

VR2385    AATTTACAGCTGATTTACAACTTGACGCTATGTGAGCTGAATGGCACAGATTGGCTAGCT    1920
ISU3927   C.......T.......T...C......................C.....G...       1917
ISU55     C.......T.......T....................................T....    1920
ISU22     C..C........................................................    1920
VR2332    C..C........................................................    1920
ISU1894   C..C........................................................    1920
ISU79     C..C.G..AT...................................................    1920

VR2385    AATAAATTTGACTGGGCAGTGGAGTGTTTTGTCATTTTTCCTGTGTTGACTCACATTGTC    1980
ISU3927   .........T......A................C.....C..................T    1977
ISU55     GG.G.........................................................    1980
ISU22     .........T......A................C.....C..T................    1980
VR2332    ..C......T......A................C.....C..T................    1980
ISU1894   G........T......A................C.....C..T................    1980
ISU79     G...G....T......A.C...............C.........T...............    1980

VR2385    TCTTATGGTGCCCTCACTACTAGCCATTTCCTTGACACAGTCGGTCTGGTCACTGTGTCT    2040
ISU3927   ..C......A.....C..C..........................T..............    2037
ISU55     ..C............C..C..........................................    2040
ISU22     ..C...............C........................C.T.A............    2040
VR2332    ..C...............C........................C.T.A............    2040
ISU1894   ..C...................C....................CCT.A............    2040
ISU79     ..C.....C.....C..C......................A.T.C.T.A............    2040

VR2385    ACCGCTGGGTTTGTTCACGGGCGGTATGTTCTGAGTAGCATGTACGCGGTCTGTGCCCTG    2100
ISU3927   .....C.....CA...............................C...............    2097
ISU55     .....C..C...TCC..............................C...............    2100
ISU22     .....C.....................C................C...............    2100
VR2332    .....C.....................C..A.............C...............    2100
ISU1894   .....C.....................C..A.............C...............    2100
ISU79     .....C.....................C..A.............C...............    2100

VR2385    GCTGCGTTGATTTGCTTCGTCATTAGGCTTGCGAAGAATTGCATGTCCTGGCGCTACTCA    2160
ISU3927   ........T...................T..........C..................T    2157
ISU55     ..............................T..A...........................    2160
ISU22     ............C......A...C...T....A............................G    2160
VR2332    ............C...........T....A..............................G.G    2160
ISU1894   ........AGC..................T....A.........................T..G    2160
ISU79     ............C................T...T............................    2160
```

FIG.1F

```
VR2385   TGTACCAGATATACCAACTTTCTTCTGGACACTAAGGGCAGACTCTATCGTTGGCGGTCG   2220
ISU3927  ....................C......................................A   2217
ISU55    ............................................................   2220
ISU22    ..........................C.................................   2220
VR2332   ............................................................   2220
ISU1894  ......................................................AT...   2220
ISU79    .....T.......................T..............................   2220

VR2385   CCTGTCATCATAGAGAAAAGGGGCAAAGTTGAGGTCGAAGGTCACCTGATCGACCTCAAA   2280
ISU3927  ..................G....T..G..................T..........A...   2277
ISU55    .......................T.....................T...........G   2280
ISU22    ..............................................T............   2280
VR2332   ..............................................T............   2280
ISU1894  ..............................................T............   2280
ISU79    ..................G...........................T.......T.....   2280

VR2385   AGAGTTGTGCTTGATGGTTCCGCGGCTACCCCTGTAACCAGAGTTTCAGCGGAACAATGG   2340
ISU3927  .A.........................A.....T..........................   2337
ISU55    ............................A......A.....A............G......   2340
VR2385   ............................................................   2340
ISU22    ...........................T...A.....A......................   2340
VR2332   ...........................T...A.....A......................   2340
ISU1894  ..........C................T...A.....A......................   2340
ISU79    ...........................T...A.....A......................   2340
                        ***<ORF5
VR2385   AGTCGTCCTTAG   2352
ISU3927  G......C...   2349
ISU55    G..........   2352
VR2385   ...........   2352
ISU22    G..........   2352
VR2332   G..........   2352
ISU1894  G..........   2352
ISU79    G..........   2352
```

FIG. 1G

```
A
VR2385  MKWGLC--K----AFLTKLAN-FLWMLSRSSWCPLLLISLYFWPFCLASPSQVGWWSFASDWFAPRYSVRALPFTLSNYRRSYEAFLSQCQ  83
ISU22   .......P----..................................................P.........................  83
ISU79   .......P----.........................S........................P.........................  83
ISU55   .......P----..................................................P.........................  83
ISU1894 .......P----.........................S........................P.........................  83
ISU3927 Q..P---..RSV..........................S.......................P.........................  83
VR2332  ...P---..................................LPA..................P.........................  83
LV      .Q..H.GV.SASCSWTPS.SSLLV.LI-----..PF----.Y.

```
        GFVPSGLSSEGHLTSAYAWLASLSFSYTTQFHPEIFGIGNWSRVYVDIKHQFICAVHDGQNTTLPHHDNISAVLQTYYQHQVDGGNWFH
B
VR2385  MANSCTFLYIFLCCSFLYSFCCAVVAGSNATYCFWFPLVRGNFSFELTVNYTVCPPCLTRQAAAEAYEPGRSLWCRIGHDRCGEDDHDEL  90
ISU55   ...............................................T.........................Y..............  90
ISU79   .V...A..H.......L........T....................................I.........Y..............  90
ISU1894 .V......H.......................A............M...........V..............Y..............  90
ISU22   ........H.......................T.F...........................I.........Y..............  90
ISU3927 ........H.L.............V.TDA..F..............M.................QI...N...N.............  90
VR2332  .V......H..............................................................T.I.........Y...  90
LV      ..HQ.ARFHF..GFIC.LVHS.LASN.SS.L.........AH..T....I..I.M.S.S..RQRL...NM..K......E..R......  90

VR2385  GFVPSGLSSEGHLTSAYAWLASLSFSYTTQFHPEIG

```
VR2385    MGASLLFLLVGFKCLLLVSQAFACKPCFSSSLSDIKTNTNTAAAGFAVLQDISCLRHRN-SASE---AIRKVPQCRTAIGTPVYITVTANVT    86
VR2332    .AS......V.....................A...................D-..........-.........I...........V.I.....    86
ISU55     .A.............................A..............Y...-..........-.........I.....F.I....M.......    86
ISU1894   .AS....M.......................A...............S..-..........-.........I...............I....    86
ISU22     .AS....M.......................A...............S.G.D-.

D

```
VR2385    MLGKCLTAGCCSQLLFLWCIVPSCFVA--LVSANGNSGSNLQLIYNLTLCELNGTDWLANKFDWAVECFVIFPVLTHIVSYGALTTSHFL    88
VR2332    ..E......R.S.....F.AV--..AN.SND.S.H.................................S..................    88
ISU55     .........Y.S.....W.--..A...SSNS.H..............................GE.......................  88
ISU1894   .........R.S.....F.AV--..AN.SA..S.H................................D..S.................  88
ISU79     .........R.S..F..F.AV--..A..SNS.S.H....................................S.................  88
ISU22     .......V.....R.S.....F.TV--..AD.HS..S.H.............................DR..S.................  88
ISU3927   ..............RS.F.LA.-........S.H..........................................S.............  87
L

```
                              -89         +1>ORF3
ISU-1894-mRNA3                GUAACC...AUG
ISU-79-mRNA3                  GUAACC...AUG

-236        +1>ORF4
ISU-1894                      UUGACu...AUG
ISU-79-mRNA                   UUGACC...AUG

-10         +1>ORF4
ISU-1894-mRNA4                UUCACC...AUG
ISU-79-mRNA4                  UUCACC...AUG
```

```
                           -26 (mRNA2)                  +1>ORF2
ISU79    GTTTTATTTCCCTCCGGGCCCTGTCATTGAACCAACTTTAGGCCTGAATTGAAATGAAAT  60
ISU1894  ..............C.....-----...................................

ISU79    GGGGTCCATGCAAAGCCTTTTTGACAAAATTGGCCAACTTTTTGTGGATGCTTTCACGGA 120
ISU1894  .......G.................................................... 120

ISU79    GTTCTTGGTGTCCATTGTTGATATCATTATATTCTTGGCCATTTTGTTTGGCTTCACCAT 180
ISU1894  ....C................C.....T................................ 180

ISU79    CGCCGGTTGGCTGGTGGTCTTTTGCATCAGATTGGTTTGCTCCGCGATACTCCGTACGCG 240
ISU1894  ............................................................ 240

ISU79    CCCTGCCATTCACTCTGAGCAATTACAGAAGATCTTATGAGGCCTTTCTTTCCCAGTGCC 300
ISU1894  .....................................................T.A... 300

ISU79    AAGTGGACATTCCCACCTGGGGAACTAAACATCCTTTGGGGATGTTTTGGCACCATAAGG 360
ISU1894  ............................................................ 360

ISU79    TGTCAACCCTGATTGATGAGATGGTGTCGCGTCGAATGTACCGCATCATGGAAAAAGCAG 420
ISU1894  .....................A...........C.......................... 420

ISU79    GACAGGCTGCCTGGAAACAGGTGGTGAGCGAGGCTACGCTGTCTCGCATTAGTAGTTTGG 480
ISU1894  .G............................................C............ 480

ISU79    ATGTGGTGGCTCATTTTCAGCATCTTGCCGCCATCGAAGCCGAGACCTGTAAATATTTGG 540
ISU1894  ..........................T.........T....................... 540
                                                         -89(mRNA3)
ISU79    CCTCCCGGCTGCCCATGCTACACAACCTGCGCATGACAGGGTCAAATGTAACCATAGTGT 600
ISU1894  ................T.........A...................-----......... 600

ISU79    ATAATAGTACTTTGAATCGGGTGTTTGCTATTTTCCCAACCCCTGGTTCCCGGCCAAAGC 660
ISU1894  ...........C.G.G.A.......................................... 660
         +1>ORF3
ISU79    TTCATGACTTTCAGCAATGGCTAATAGCTGTGCATTCCTCCATATTTTCCTCTGTTGCAG 720
ISU1894  .......T.......T......A...................................... 720

ISU79    CTTCTTGTACTCTCTTTGTTGTGCTGTGGTTGCGGGTTCCAATACTACGTACTGTTTTTG 780
ISU1894  ............T.............C...........G..................... 780
                                               ***<ORF2(ISU79)
ISU79    GTTTCCGCTGGTTAGGGGCAATTTTTCTTTCGAACTCATAGTGAATTACACGGTGTGCCC 840
ISU1894  ...................G........C...........G...............T.. 840
                                                      ***<ORF2(ISU1894)
```

FIG. 9A

```
ISU79   ACCTTGCCTCACCCGGCAAGCAGCCGCAGAGGCCTACGAACCCGGTAGGTCTCTTTGGTG 900
ISU1894 .........................................T.................900

ISU79   CAGGATAGGGTACGATCGATGTGGAGAGGACGACCATGACGAGCTAGGGTTTATGATACC 960
IAU1894 ..........T..C........G........T............................960
                          -236(ISU79 mRNA3-1)
ISU79   GTCTGGCCTCTCCAGCGAAGGCCACTTGACCAGTGTTTACGCCTGGTTGGCGTTCTTGTC 1020
ISU1894 .C.............................T..................T.....1020

ISU79   CTTCAGCTACACGGCCCAGTTCCACCCCGAGATATTCGGGATAGGGAATGTGAGTCGAGT 1080
ISU1894 .....................T......................................1080
         +1>ORF3-1
ISU79   TTATGTTGACATCAAACATCAACTCATCTGCGCCGAACATGACGGGCAGAACACCACCTT 1140
ISU1894 .............................T..........A......G.......1140

ISU79   GCCTCGTCATGACAACATTTCGGCCGTGTTTCAGACCTATTACCAACATCAAGTCGACGG 1200
ISU1894 ..............T.....A................................T..1200
         -10(mRNA4)+1>ORF4
ISU79   CGGCAATTGGTTTCACCTAGAATGGCTGCGTCCCTTCTTTTCCTCATGGTTGGTTTTAAA 1260
ISU1894 ..........._____....T.....................................1260
                  ***<ORF3-1
ISU79   TGTCTCTTGGTTTCTCAGGCGTTCGCCTGCAAACCATGTTTCAGTTCGAGTCTTGCAGAC 1320
ISU1894 ..........A..................C................T1320

ISU79   ATTAAGACCAACACCACCGCAGCGGCAAGCTTTGCTGTCCTCCAAGACATCAGTTGCCTT 1380
ISU1894 ..............T.............................................1380
                                                                  **
ISU79   AGGCATCGCAACTCGGCCTCTGAGGCGATTCGCAAAATCCCTCAGTGCCGTACGGCGATA 1440
ISU1894 ............................................................1440
         *<ORF3
ISU79   GGGACACCTATGTATATTACCATCACAGCCAATGTGACAGATGAAAATTATTTACATTCT 1500
ISU1894 ........CG.............................G...............1500

ISU79   TCTGATCTCCTCATGCTCTCTTCTTGCCTTTTCTATGCTTCTGAGATGAGTGAAAAGGGA 1560
ISU1894 ...............T.........C........................A...1560

ISU79   TTTGAGGTGGTTTTTGGCAATGTGTCAGGCATCGTGGCTGTGTGTGTCAATTTTACCAGC 1620
ISU1894 ..CA.......A...............................................1620
                                                           -105
ISU79   TACGTTCAACATGTCAGGGAGTTTACCCAACGCTCCTTGATGGTCGACCATGTGCGGCTG 1680
ISU1894 .....C..............................C..G......_____....T..1680
                                         -70       -55(ISU79 mRNA5)
ISU79   CTCCATTTCATGACACCTGAGACCATGAGGTGGGCAACCGTTTTAGCCTGTCTTTTTGCT 1740
ISU1894 .................A.....................T...................C1740
         -70(ISU1894 mRNA5)
```

FIG. 9B

```
                            ***<ORF4      +1>ORF5
ISU79    ATTCTGTTGGCAATTTGAATGTTTAAGTATGTTGGGGAAATGCTTGACCGTGGGCTGTTG1800
ISU1894  ......C..........................................C........1800

ISU79    CTCGCGATTGCTTTCTTTGTGGTGTATCGTGCCGTTCTGTTTTACTGTGCTCGCCGACGC1860
ISU1894  .........................................G...........A....1860

ISU79    CCACAGCAACAGCAGCTCTCATCTGCAATTGATTTACAACTTGACGCTATGTGAGCTGAA1920
ISU1894  .AG.GC...........C.....A..GC................................1920

ISU79    TGGCACAGATTGGCTAGCTGATAGATTTGATTGGGCAGTGGAGAGCTTTGTCATCTTTCC1980
ISU79    ...............A........................T..................1980

ISU79    TGTTTTGACTCACATTGTCTCCTATGGCGCCCTCACCACCAGCCATTTCCTTGACACAAT2040
ISU1894  C....................T........T..T......C............G.2040

ISU79    TGCTTTAGTCACTGTGTCTACCGCCGGGTTTGTTCACGGGCGGTATGTCCTAAGTAGCAT2100
ISU1894  C..C........................................................2100

ISU79    CTACGCGGTCTGTGCCCTGGCTGCGTTGACTTGCTTCGTCATTAGGTTTGTGAAGAATTG2160
ISU1894  ..........................AG................CA............2160

ISU79    CATGTCCTGGCGCTACTCATGTACTAGATATACCAACTTTCTTCTGGATACTAAGGGCAG2220
ISU1894  ..............T..G.....C........................C...........2220

ISU79    ACTCTATCGTTGGCGGTCGCCTGTCATCATAGAGAAGAGGGGCAAAGTTGAGGTCGAAGG2280
ISU1894  ..............AT....................A......................2280
                                                      -32      -23(mRNA6)
ISU79    TCATCTGATCGATCTCAAAAGAGTTGTGCTTGATGGTTCCGTGGCAACCCCTATAACCAG2340
ISU1894  ...........C.................C..........................2340
              +1>ORF6           ***<ORF5
ISU79    AGTTTCAGCGGAACAATGGGGTCGTCCTTAGATGACTTCTGTTATGATAGTACGGCTCCA2400
ISU1894  ..................................................CC........2400

ISU79    CAAAAGGTGCTTTTGGCATTTTCTATTACCTACACGCCAGTAATGATATATGCCCTAAAG2460
ISU1894  ..............G....................G....................2460

ISU79    GTGAGTCGCGGCCGACTGCTAGGGCTTCTGCACCTTTTGATTTTCCTGAACTGTGCTTTC2520
ISU1894  .......................................C........T........2520

ISU79    ACCTTCGGGTACATGACATTCATGCACTTTCAGAGTACAAATAAGGTCGCGCTCACTATG2580
ISU1894  ................G........................................2580
```

FIG. 9C

```
ISU79    GGAGCAGTAGTTGCACTCCTTTGGGGGGTGTACTCAGCCATAGAAACCTGGAAATTCATC2640
ISU1894  ............................................................2640

ISU79    ACCTCCAGATGCCGTTTGTGCTTGCTAGGCCGCAAGTACATTCTGGCCCCTGCCCACCAC2700
ISU1894  ............................................................2700
                                                       -129
ISU79    GTTGAAAGTGCCGCAGGCTTTCATCCGATTGCGGCAAATGATAACCACGCATTTGTCGTC2760
ISU1894  ............................................................2760

ISU79    CGGCGTCCCGGCTCCACTACGGTCAACGGCACATTGGTGCCCGGGTTGAAAAGCCTCGTG2820
ISU1894  ............................................................2820
                                               -15 (mRNA7)    +1>ORF7***<ORF6
ISU79    TTGGGTGGCAGAAAAGCTGTTAAACAGGGAGTGGTAAACCTTGTCAAATATGCCAAATAA2880
ISU1894  ............................................................2880

ISU79    CAACGGCAAGCAGCAGAAGAGAAAGAAGGGGGATGGCCAGCCAGTCAATCAGCTGTGCCA2940
ISU1894  ............................................................2940

ISU79    GATGCTGGGTAAGATCATCGCCCAGCAAAACCAGTCTAGAGGCAAGGGACCGGGAAAGAA3000
ISU1894  .....................T...............C.....................3000

ISU79    AAATAAGAAGAAAAACCCGGAGAAGCCCCATTTTCCTCTAGCGACTGAAGATGATGTCAG3060
ISU1894  ...C........................................................3060

ISU79    ACATCACTTTACCCCTAGTGAGCGGCAATTGTGTCTGTCGTCAATCCAAACTGCCTTTAA3120
ISU1894  ........C...........................................G..C....3120

ISU79    TCAAGGCGCTGGGACTTGCACCCTGTCAGATTCAGGGAGGATAAGTTACACTGTGGAGTT3180
ISU1894  ............................................................3180
                                                                    **
ISU79    TAGTTTGCCTACGCATCATACTGTGCGCTTGATCCGCGTCACAGCATCACCCTCAGCATG3240
ISU1894  .........A..................................................3240
         *<ORF7
ISU79    ATGGGCTGGCATTCTTGAGGCATCCCAGTGTTTGAATTGGAAGAATGCGTGGT 3293
ISU1894  .................................................... 3293
```

FIG. 9D

REACTIVITY[a] OF THE MAbs WITH PRRSV FIELD ISOLATES DETECTED WITH FIXED-CELL ELISA

| VIRUS ISOLATE | | MAbs TO GP4 PROTEIN | | | | MAbs TO GP5 PROTEIN | | | | | | MAb TO N |
|---|---|---|---|---|---|---|---|---|---|---|---|---|
| NAME | SOURCE | PP4bB3 | PP4bC5 | PP4cB11 | PP4dG6 | PP5eA12 | PP5eD3 | PP5dB4 | PP5cH5 | PP5cG12 | PP5bH4 | PP7eF11 |
| VR2385 | IOWA | 512 | 64 | 512 | 32 | >256 | >256 | >256 | 512 | 256 | 64 | >1600 |
| ISU28 | IOWA | 1024 | 64 | 128 | <32 | 256 | 256 | 128 | 128 | 64 | 32 | >3200 |
| RP20 | VIRGINIA | 512 | 256 | 1024 | 32 | 64 | 128 | 64 | 512 | 256 | <32 | >1600 |
| RP45 | MINNESOTA | 128 | 32 | 256 | 128 | 128 | >256 | >256 | 256 | 64 | 32 | >1600 |
| RP10 | IOWA | 128 | 32 | 16 | 128 | >256 | >256 | 128 | 64 | 64 | 32 | >3200 |
| RP11 | IOWA | 1024 | 8 | 32 | >256 | >256 | >256 | 128 | 128 | 32 | <32 | >1600 |
| ISU22 | IOWA | 512 | 64 | 32 | 32 | 128 | 128 | 64 | 128 | 32 | 32 | >3200 |
| ISU7229 | IOWA | 512 | 64 | 32 | <32 | 64 | 64 | 64 | 128 | 32 | 32 | >3200 |
| ISU-55 | IOWA | 512 | 16 | 16 | <32 | 128 | 128 | 64 | 128 | 64 | 32 | >3200 |
| RP29 | IOWA | 1024 | 512 | 64 | 32 | 128 | 128 | 32 | 128 | 64 | <32 | >3200 |
| RP12 | IOWA | 1024 | 64 | 1024 | 64 | <32 | 128 | <32 | 256 | 64 | <32 | >1600 |
| RP15 | MINNESOTA | 512 | 512 | 512 | <32 | <32 | <32 | <32 | 128 | 128 | <32 | >1600 |
| ISU4 | IOWA | 1024 | 128 | 32 | <32 | 32 | <32 | <32 | 128 | 64 | <32 | >3200 |
| RP18 | VIRGINIA | 1024 | 16 | 64 | <32 | <32 | <32 | 32 | 64 | 64 | 32 | >1600 |
| RP24 | IOWA | 1024 | 128 | 32 | <32 | <32 | 32 | 32 | 128 | 64 | 32 | >3200 |
| RP46 | MINNESOTA | 256 | 64 | 32 | 32 | 32 | 128 | 32 | 128 | 64 | 32 | >3200 |
| RP22 | IOWA | 512 | 32 | 32 | <32 | 64 | 64 | 32 | 128 | 64 | <32 | >3200 |
| RP40 | MISSOURI | 128 | 32 | 32 | 64 | 64 | 128 | 64 | 128 | 32 | 32 | >3200 |
| ISU33 | IOWA | 128 | 32 | 32 | <32 | 64 | 128 | 64 | 128 | 16 | <32 | >3200 |
| RP17 | VIRGINIA | 64 | 32 | 16 | 64 | 128 | 128 | 32 | 64 | 32 | <32 | >3200 |
| ISU51 | IOWA | <8 | <8 | <8 | 32 | 256 | 256 | 64 | <8 | 8 | <32 | 800 |
| RP36 | IOWA | 32 | <32 | <32 | 32 | <32 | 64 | 32 | 32 | 32 | 32 | >3200 |
| RP31 | IOWA | 32 | <32 | <32 | 32 | 32 | 32 | 64 | 128 | 64 | 32 | >3200 |

A. REACTIVITY WAS EXPRESSED AS TITERS OF THE REACTION OF MAbs WITH PRRSV ISOLATES. END-POINT TITERS WERE EXPRESSED AS THE RECIPROCAL OF THE HIGHEST DILUTION OF THE MAbs SHOWING ABSORBANCE $A_{405}$ LARGER THAN THE SUM OF AVERAGE NEGATIVE CONTROL'S $A_{405}$ PLUS 3 STANDARD DEVIATIONS.

PRIMERS-USED TO AMPLIFY PRRSV ORFs 2 THROUGH 7 GENES WITH PCR

| ORF | FORWARD PRIMER | REVERSE PRIMER |
| --- | --- | --- |
| 2 | 5'GCACGGATCCGAATTAACATG AAATGGGGT 3' | 5'CCACCTGCAGATTCACCGTGA GTTCGAAAG 3' |
| 3 | 5'CGTCGGATCCTCCTACAATGG CTAATAGCT 3' | 5'CGCGCTGCAGTGTCCCTATCG ACGTGCGGC 3' |
| 4 | 5'GTATGGATCCGCAATTGGTTT CACCTATAA 3' | 5'ATAGGAATTCAACAAGACGGC ACGATACAC 3' |
| 5 | 5'TGCCAGGATCCGTGTTTAAAT ATGTTGGGG 3' | 5'CGTGGAATTCATAGAAAACGC CAAGAGCAC 3' |
| 6 | 5'GGGGATCCAGAGTTTCAGCGG 3' | 5'GGGAATTCTGGCACAGCTGAT TGAC 3' |
| 7 | 5'GGGGATCCTTGTTAAATATGC C 3' | 5'GGGAATTCACCACGCATTC 3' |

FIG.15

RECOMBIANT PROTEINS OF PRRSV ORFs 2 to 5 EXPRESSED IN INSECT CELLS

| ORF | PREDICTED $M_t$ OF PRODUCT $(kDa)^a$ | N-LINKED GLYCOSYLATION SITES$^a$ | EXPRESSED PRODUCTS IN INSECT CELLS $(kDa)^b$ | BANDS AFTER TUNICAMYCIN TREATMENT $(kDa)^c$ | POSSIBLE CORE PROTEIN $(kDa)^d$ |
|---|---|---|---|---|---|
| 2 | 29.5 | 2 | 27, 29 | 25, 27 | 25 |
| 3 | 28.7 | 7 | 22-43 | 22-27 | 27 |
| 4 | 19.5 | 4 | 15-30 | 15, 18 | 15 |
| 5 | 22.2 | 2 | 16-26 | 16, 18 | 16 |

A. PREDICTED $M_t$ OF PRODUCTS OF PRRSV ORFS 2 TO 5 AND N-GLYCOSYLATION SITES ARE BASED ON NUCLEOTIDE SEQUENCE STUDIES (MENG ET AL, 1994 & MOROZOV ET AL., 1995).
B. EXPRESSED PRODUCTS IN INSECT CELLS (DETAILS SEE RESULT SECTION AND FIG. 5).
C. BANDS AFTER TUNICAMYCIN TREATMENT WERE DETERMINED BY IMMUNOBLOTTING ANALYSIS (DETAILS SEE RESULT SECTION AND FIG. 6).
D. LEADER-FREE CORE PROTEINS ARE DETERMINED ON THE BASIS OF TUNICAMYCIN TREATMENT ANALYSIS. THE PRESENCE OF THE OTHER BANDS IN THE RECOMBINANT PRODUCTS AFTER TUNICAMYCIN TREATMENT WAS POSSIBLY DUE TO O-LINKED GLYCOSYLATION, PHOSPHORYLATION OR OTHER POST-TRANSLATIONAL MODIFICATIONS.

FIG.16

SEQUENCE LISTING

<160> NUMBER OF SEQ ID NOS: 108

<210> SEQ ID NO 1
<211> LENGTH: 2352
<212> TYPE: DNA
<213> ORGANISM: Porcine reproductive and respiratory syndrome virus

<400> SEQUENCE: 1

```
cctgtcattg aaccaacttt aggcctgaat tgagatgaaa tggggtctat gcaaagcctt        60
tttgacaaaa ttggccaact ttttgtggat gctttcacgg agttcttggt gtccattgtt       120
gatatcatta tattttggc cattttgttt ggcttcacca tcgcaggttg gctggtggtc       180
```

-continued

```
ttttgcatca gattggtttg ctccgcgata ctccgtgcgc gccctgccat tcactctgag    240
caattacaga agatcctatg aggcctttct ctctcagtgc caggtggaca ttcccacctg    300
gggaactaaa catcccttgg ggatgctttg gcaccataag gtgtcaaccc tgattgatga    360
aatggtgtcg cgtcgaatgt accgcatcat ggaaaaagca ggacaggctg cctggaaaca    420
ggtagtgagc gaggctacgc tgtctcgcat tagtagtttg gatgtggtgg ctcattttca    480
gcatcttgcc gccattgaag ccgagacctg taaatatctg gcctctcggc tgcccatgct    540
acaccacctg cgcatgacag ggtcaaatgt aaccatagtg tataatagta ctttgaatca    600 ggtgttttgct gttttcccaa cccctggttc ccggccaaag cttcatgatt tccagcaatg    660
gctaatagct gtacattcct ctatattttc ctctgttgca gcttcttgta ctcttttgt    720 tgtgctgtgg ttgcgggttc caatgctacg tactgttttt ggtttccgct ggttaggggc    780 aattttctt tcgaactcac ggtgaattac acggtgtgcc cgccttgcct cacccggcaa    840
gcagccgcag aggcctacga acccggcagg tcccttggt gcaggatagg gcatgatcga    900 tgtgggagg acgatcatga tgaactaggg tttgtggtgc cgtctggcct ctccagcgaa    960
ggccacttga ccagtgctta cgcctggttg gcgtccctgt ccttcagcta acggcccag    1020 ttccatcccg agatattcgg gatagggaat gtgagtcgag tctatgttga catcaagcac    1080
caattcattt gcgctgttca tgatgggcag aacaccacct gcccccacca tgacaacatt    1140
tcagccgtgc ttcagaccta ttaccagcat caggtcgacg ggggcaattg gtttcaccta    1200
gaatgggtgc gtcccttctt ttcctcttgg ttggttttaa atgtctcttg gtttctcagg    1260
cgttcgcctg caagccatgt ttcagttcga gtctttcaga catcaagacc aacaccaccg    1320
cagcggcagg ctttgctgtc ctccaagaca tcagttgcct taggcatcgc aactcggcct    1380
ctgaggcgat tcgcaaagtc cctcagtgcc gcacggcgat agggacaccc gtgtatatca    1440
ctgtcacagc caatgttacc gatgagaatt atttgcattc ctctgatctt tcatgctttt    1500
cttcttgcct tttctatgct tctgagatga gtgaaaaggg atttaaggtg gtatttggca    1560
atgtgtcagg catcgtggca gtgtgcgtca acttcaccag ttacgtccaa catgtcaagg    1620
aatttaccca acgttccttg gtagttgacc atgtgcggct gctccatttc atgacgcccg    1680
agaccatgag gtgggcaact gttttagcct gtcttttttac cattctgttg gcaatttgaa    1740
tgtttaagta tgttggggaa atgcttgacc gcgggctgtt gctcgcaatt gcttttttta    1800
tggtgtatcg tgccgtcttg ttttgttgcg ctcgtcagcg ccaacgggaa cagcggctca    1860
aatttacagc tgatttacaa cttgacgcta tgtgagctga atggcacaga ttggctagct    1920
aataaatttg actgggcagt ggagtgtttt gtcattttc ctgtgttgac tcacattgtc    1980
tcttatggtg ccctcactac tagccatttc cttgacacag tcggtctggt cactgtgtct    2040
accgctgggt tgttcacgg gcggtatgtt ctgagtagca tgtacgcggt ctgtgccctg    2100
gctgcgttga tttgcttcgt cattaggctt gcgaagaatt gcatgtcctg cgcgctactca    2160 tgtaccagat ataccaactt tcttctggac actaagggca gactctatcg ttggcggtcg    2220
cctgtcatca tagagaaaag gggcaaagtt gaggtcgaag gtcacctgat cgacctcaaa    2280
agagttgtgc ttgatggttc cgcggctacc cctgtaacca gagtttcagc ggaacaatgg    2340
agtcgtcctt ag                                                       2352
```

<210> SEQ ID NO 2
<211> LENGTH: 2349
<212> TYPE: DNA
<213> ORGANISM: Porcine reproductive and respiratory syndrome virus -continued

<400> SEQUENCE: 2

```
cctatcattg aaccaacttt gggtctagac tgaaatgcaa tggggtccat gcaaagcctt      60
tttgacaaga tcggtcaact ttttgtggat gctttcacgg agttcttggt gtccattgtt     120
gatatcatca tattttttggc cattttgttt ggcttcacca ttgccggctg gctggtggtc    180
ttttgcatca gattggtttg ctccgcgata ctccgtgcgc gccctgccat tcaccctgag     240
caattacaga agatcctatg aggcctttct ttctcagtgc caggtggaca ttcccgcctg     300
gggaacaaga catcctttag ggatgctttg gcaccacaag gtgtcaaccc tgattgatga     360
aatggtgtcg cgtcgaatgt accgcatcat ggaaaaagca ggacaggctg cctggaaaca     420
ggtggtgagt gaggctacgc tgtctcgcat tagtggtttg gatgtggtgg cccatttttca    480
gcaccttgcc gccattgaag ccgagacttg taaatatttg gcctctcggt tgcccatgct     540
acacaacctg cgtattacag ggtcaaatgt aaccatagtg cataatagta ctttgaatca     600
ggtgtttgct attttcccaa ccccggttc tcggccaaag ctccatgatt ttcagcaatg      660
gctaatagct gtacattcct cgatatcctc ctctgttgca gcttcttgta ctcttttttgt    720
tgtgttgtgg ttacggatgc caatgctacg ttctgttttt ggtttccgct ggttaggggc     780
aattttttcct tcgagctcat ggtgaattac acggtgtgcc caccttgcct cacccggcaa    840
gcagccgcac agatctacga acccaacagg tctctttggt gcaggatcgg gaatgatcga     900
tgtggtgagg acgatcacga cgaactagga tttacagtac cgcctggcct ctccaaagaa    960
gtccatttga ccagtgttta cgcctggttg gcgtttctgt ccttcagtaa cacggcccag   1020
tttcatcccg agatattcgg aatagggaat gtgagtaagg tctatgttga catcaatcat   1080
caactcattt gtgctgttca tgacgggcag aacaccacct gcctcgcca tgacaacatt    1140
tctgccgtgt ttcagaccta ttaccaacac caagtcgatg gtggcaactg gtttcaccta   1200
gaatggctgc gtcccttctt ttcctcttgg ttggttttga atgtctcctg gtttctcagg   1260
cgttcgcctg caagccatgt ttcagttcga gtctttcaga catcaagacc aacaccaccg   1320
cggcagcaaa tttcgctgtc ctccaggaca tcggctgcct taggcatggc aactcgacca   1380
ctgaggcgtt tcgcaaaatc cctcagtgcc gcacggcgat agggacaccc gtgtatatca   1440
ctatcacagc caatgtaaca gatgagaact atttgcattc ttctgatctt ctcatgcttt   1500
cctcttgcct tttctacgct tctgagatga gtgaaaaggg gtttaaggtg gtgtttggca   1560
atgtgtcagg caccgtggct gtgtgcatca attttaccag ctatgtccaa cacgtcaagg   1620
agtttaccca acgctcctta gtggtcgacc atgtgcggct gctccatttc atgacacctg   1680
aaaactatgag gtgggcaact gttttagcct gtcttttcgc cattctgttg gcaatttgaa   1740
tgtttaagta tgttggggaa atgcttgacc gcgggctgtt gctcgcgatc gcttttttttg   1800
tggtgtatcg tgccgttctg tcttgctgcg ctcgtcagcc caacaacag cagctcccat    1860
ttacagttga tttataacct gacgctatgt gagctgaatg gcacagactg gctggctaat   1920
aaatttgatt gggcagtgga gagttttgtc atctttcccg tgttgactca cattgtttcc   1980
tatggtgcac tcaccaccag ccatttcctt gacacagtcg gtctggttac tgtgtctacc   2040
gccgggtttc atcacgggcg gtatgttctg agtagcatct acgcggtctg tgccctggct   2100
gcgtttattt gcttcgtcat taggtttgcg aagaactgca tgtcctggcg ctactcttgt   2160
accagatata ccaacttcct tctggacact aagggcagcc tctatcgttg gcggtcacct   2220
gtcatcatag agaaaggggg taaggttgag gtcgaaggtc atctgatcga cctaaaaaaa   2280
```

-continued

```
gttgtgcttg atggttccgc ggcaacccct ttaaccagag tttcagcgga acaatggggt    2340
cgtccctag                                                           2349

<210> SEQ ID NO 3
<211> LENGTH: 2352
<212> TYPE: DNA
<213> ORGANISM: Porcine reproductive and respiratory syndrome virus

<400> SEQUENCE: 3
cctatcattg aaccaacttt aggcctgaat tgaaatgaaa tggggtctat gcaaagcctt      60
tttgacaaaa ttggccaact tttcgtggat gctttcacgg agttcttggt gtccattgtt    120
gatatcatta tattttggc cattttgttt ggcttcacca tcgccggttg gctggtggtc     180
ttttgcatca gattggtttg ctccgcgata ctccgtgcgc gccctgccat tcactctgag    240
caattacaga gatcctatg aggcctttct ttctcagtgc caggtggaca ttcccacctg     300
gggaattaaa catcctttgg ggatgctttg gcaccataag gtgtcaaccc tgattgatga    360
aatggtgtcg cgtcgaatgt accgcatcat ggaaaaagca ggacaggctg cctggaaaca    420
ggtggtgagc gaggctacgc tgtctcgcat tagtagtttg gatgtggtgg ctcactttca    480
gcatcttgcc gccattgaag ccgagacctg taaatatttg gcctctcggc tgcccatgct    540
acacaacctg cgcatgacag ggtcaaatgt aaccatagtg tataatagta ctttgaatca    600
ggtgcttgct atttttcccaa ccctggttc ccggccaaag cttcatgatt tcagcaatg     660
gctaatagct gtacattcct ctatattttc ctctgttgca gcttcttgta ctctttttgt    720
tgtgctgtgg ttgcgggttc caatgctacg tattgctttt ggtttccgct ggttaggggc    780
aattttcctt tcgaactcac agtgaactac acggtgtgtc caccttgcct cacccggcaa    840
gcagccacag aggcctacga acctggcagg tctctttggt gcaggatagg gtatgatcgc    900
tgtgggagg acgatcatga tgaactaggg tttgtggtgc cgtctggcct ctccagcgaa    960
ggccacttga ccagtgttta cgcctggttg gcgttcctgt ctttcagtta cacagcccag   1020
ttccatcctg agatattcgg atagggaat gtgagtcaag tttatgttga catcaggcat    1080
caattcattt gcgccgttca cgacgggcag aacgccactt gcctcgcca tgacaatatt    1140
tcagccgtgt tccagactta ttaccaacat caagtcgacg gcggcaattg gtttcaccta   1200
gaatggctgc gtcccttctt ttcctcttgg ttggttttaa atgtctcttg gtttctcagg   1260
cgttcgcctg caagccatgt ttcagttcga gtcttgcaga cattaagacc aacaccaccg   1320
cagcggcagg ctttgctgtc ctccaagaca tcagttgcct taggtatcgc aactcggcct   1380
ctgaggcgtt tcgcaaaatc cctcagtgtc gtacggcgat agggacaccc atgtatatta   1440
ctgtcacagc caatgtaacc gatgagaatt atttgcattc ctctgacctt tcatgctttt   1500
cttcttgcct tttctacgct tctgagatga gtgaaaaggg atttaaagtg gtatttggca   1560
atgtgtcagg catcgtggct gtgtgcgtca actttaccag ctacgtccaa catgtcaagg   1620
aatttaccca cgctccttg gtagtcgacc atgtgcggct gctccatttc atgacacctg    1680
agaccatgag gtgggcaact gttttagcct gtctttttgc cattctgttg gccatttgaa    1740
tgtttaagta tgttggggaa atgcttgacc gcgggctatt gctcgtcatt gcttttttg    1800
tggtgtatcg tgccgtcttg gtttgttgcg ctcgccagcg ccaacagcag caacagctct   1860
catttacagt tgatttataa cttgacgcta tgtgagctga atggcacaga ttggttagct    1920
ggtgaatttg actgggcagt ggagtgtttt gtcatttttc ctgtgttgac tcacattgtc   1980
tcctatggtg ccctcaccac cagccatttc cttgacacag tcggtctggt cactgtgtct    2040
```

-continued

```
accgccggct tttcccacgg gcggtatgtt ctgagtagca tctacgcggt ctgtgccctg    2100
gctgcgttga tttgcttcgt cattaggttt acgaagaatt gcatgtcctg gcgctactca    2160
tgtaccagat ataccaactt tcttctggac actaagggca gactctatcg ttggcggtcg    2220
cctgtcatca tagagaaaag gggtaaagtt gaggtcgaag gtcatctgat cgacctcaag    2280
agagttgtgc ttgatggttc cgcggcaacc cctataacca agtttcagc ggagcaatgg     2340 ggtcgtcctt ag                                                        2352
```

<210> SEQ ID NO 4
<211> LENGTH: 2351
<212> TYPE: DNA
<213> ORGANISM: Porcine reproductive and respiratory syndrome virus

<400> SEQUENCE: 4

```
cctgtcattg aaccaacttt aggcctgaat tgaaatgaaa tgggggccat gcaaagcctt      60
tttgacaaaa ttggccaact ttttgtggat gctttcacgg agttcttggt gtccattgtt     120
gatatcatta tattttggc cattttgttt ggcttcacca tcgccggttg gctggtggtc      180
ttttgcatca gattggtttg ctccgcgata ctccgtgcgc gccctgccat tcactctgag    240
caattacaga gatcttatg aggcctttct ttcccagtgc caagtggaca ttcccacctg    300
gggaactaaa catcctttgg ggatgttgtg gcaccataag gtgtcaaccc tgattgatga    360
aatggtgtcg cgtcgaatgt accgcatcat ggaaaaagca gggcaggctg cctggaaaca   420
ggtggtgagc gaggctacgc tgtctcgcat tagtagtttg gatgtggtgg ctcattttca    480
gcatcttgct gccattgaag ccgagacctg taaatatttg gcctcccggc tgcccatgct    540
acacaacctg cgcatgacag ggtcaaatgt aaccatagtg tataatagta ctttgaatca    600
ggtgtttgct atttttccaa cccctggttc ccggccaaag cttcatgatt ttcagcaatg    660
gttaatagct gtacattcct ccatatttc ctctgttgca gcttcctgta ctctttttgt    720
tgtgctgtgg ttgcgggttc aatactacg ttctgttttt ggtttccgct ggttaggggc    780
aatttttctt tcgagctcac ggtgaattac acggtgtgtc caccttgcct cacccggcaa    840
gcagccgcag agatctacga acccggtagg tctctttggt gcaggatagg gtatgaccga    900
tgtggggagg acgatcatga cgagctaggg tttatggtac cacctggctt ctccagcgaa    960
ggccacttga ctagtgttta cgcctggttg gcgtttttgt ccttcagcta cacggcccag   1020
ttccatcccg agatattcgg ataggggaac gtgagtcgag tttatgttga catcaaacat   1080
caactcatct gcgccgaaca tgacgggcaa acaccacct tgcctcgtca tgacaacatt    1140
tcagccgtgt ttcagaccta ttaccaacat caagtcgacg gtggcaattg gtttcaccta   1200
gaatggcttc gtcccttctt ttcctcatgg ttggttttaa atgtctcttg gtttctcagg   1260
cgttcgcctg caaaccatgt ttcagttcga gtcttgcaga tattaagacc aacaccaccg   1320
cagcggcaag ctttgctgtc ctccaagaca tcggttgcct taggcatcgc gactcggcct   1380
ctgaggcgat tcgcaaaatc cctcagtgcc gtacggcgat agggacaccc gtgtatatta   1440
ccatcacagc caatgtgaac gatgagaatt atttacattc ttctgatctc ctcatgcttt   1500
cttcttgcct tttctatgct tctgagatga gtgaaaaggg gttaaggtg gtatttggca    1560 atgtgtcagg catcgtggct gtgtgtgtca attttaccag ctatgtccaa catgtcaggg   1620
agtttaccca acgctccttg gtggtcgacc atgtgcggt gctccatttc atgacacctg    1680
agaccatgag gtgggcaact gtttagcct gtctttttgc cattctgttg gcaatttgaa    1740
```

-continued

```
tgtttaagca tgttggggaa atgcttgacc gcgggctgtt gctcgcgatt gctttctttg    1800
tggtttatcg tgccgttctg ttttgctgtg ctcgccagcg ccagcaacag cagcagctcc    1860
catctacagt tgatttataa cttgacgcta tgtgagctga atggcacaga ttggttagct    1920
aataaatttg attgggcagt ggagagtttt gtcatctttc ccgttttgac tcacattgtc    1980
tcctatggtg ccctcactac cagccatttc cttgacacag tcgctttagt cactgtgtct    2040
accgccgggt ttgttcacgg gcggtatgtc ctgagtagca tctacgcggt ctgtgccctg    2100
gctgcgttga cttgcttcat catcaggttt gcaaagaatt gcatgtcctg gcgctactcg    2160
tgtaccagat ataccaactt tctcctggac actaagggca gactctatcg ttggcggtcg    2220
cctgtcatca tagagaaaag gggcaaagtt gaggtcgaag gtcactgatc gacctcaaaa    2280
gagttgtgct tgatggttcc gtggcaaccc ctataaccag agattcagcg aacaatggg    2340 gtcgtcctta g                                                         2351

<210> SEQ ID NO 5
<211> LENGTH: 2352
<212> TYPE: DNA
<213> ORGANISM: Porcine reproductive and respiratory syndrome virus

<400> SEQUENCE: 5
cctgtcattg aaccaacttt aggcctgaat tgaaatgaaa tggggtccat gcaaagcctt      60
tttgacaaaa ttggccaact ttttgtggat gctttcacgg agttcttggt gtccattgtt     120
gatatcatta tattcttggc cattttgttt ggcttcacca tcgccggttg gctggtggtc     180
ttttgcatca gattggtttg ctccgcgata ctccgtacgc gccctgccat tcactctgag     240
caattacaga agatcttatg aggcctttct ttcccagtgc caagtggaca ttcccacctg     300
gggaactaaa catccttttgg ggatgttttg gcaccataag gtgtcaaccc tgattgatga     360
gatggtgtcg cgtcgaatgt accgcatcat ggaaaaagca ggacaggctg cctggaaaca     420
ggtggtgagc gaggctacgc tgtctcgcat tagtagtttg gatgtggtgg ctcatttttca     480 gcatcttgcc gccatcgaag ccgagacctg taaatatttg gcctcccggc tgcccatgct     540
acacaacctg cgcatgacag ggtcaaatgt aaccatagtg tataatagta ctttgaatcg     600
ggtgtttgct atttttccca cccctggttc ccggccaaag cttcatgact ttcagcaatg     660
gctaatagct gtgcattcct ccatattttc ctctgttgca gcttcttgta ctctctttgt     720
tgtgctgtgg ttgcgggttc aatactacg tactgttttt ggtttccgct ggttagggggc     780 aattttttctt tcgaactcat agtgaattac acggtgtgcc caccttgcct cacccggcaa     840
gcagccgcag aggcctacga acccgtaggg tctctttggt gcaggatagg gtacgatcga     900
tgtggagagg acgaccatga cgagctaggg tttatgatac cgtctggcct ctccagcgaa     960
ggccacttga ccagtgttta cgcctggttg gcgttcttgt ccttcagcta cggcccag     1020 ttccaccccg agatattcgg gatagggaat gtgagtcgag tttatgttga catcaaacat    1080
caactcatct gcgccgaaca tgacgggcag aacaccacct tgcctcgtca tgacaacatt    1140
tcggccgtgt ttcagaccta ttaccaacat caagtcgacg gcggcaattg gtttcaccta    1200
gaatggctgc gtcccttctt ttcctcatgg ttggttttaa atgtctcttg gtttctcagg    1260
cgttcgcctg caaaccatgt ttcagttcga gtcttgcaga cattaagacc aacaccaccg    1320
cagcggcaag ctttgctgtc ctccaagaca tcagttgcct taggcatcgc aactcggcct    1380
ctgaggcgat tcgcaaaatc cctcagtgcc gtacggcgat agggacacct atgtatatta    1440
ccatcacagc caatgtgaca gatgaaaatt atttacattc ttctgatctc ctcatgctct    1500
```

-continued

```
cttcttgcct tttctatgct tctgagatga gtgaaaaggg atttgaggtg gttttttggca     1560 atgtgtcagg catcgtggct gtgtgtgtca attttaccag ctacgttcaa catgtcaggg     1620
agtttaccca acgctccttg atggtcgacc atgtgcggct gctccatttc atgacacctg     1680
agaccatgag gtgggcaacc gttttagcct gtcttttgc tattctgttg gcaatttgaa      1740
tgtttaagta tgttggggaa atgcttgacc gtgggctgtt gctcgcgatt gctttctttg     1800
tggtgtatcg tgccgttctg ttttactgtg ctcgccgacg cccacagcaa cagcagctct     1860
catctgcaat tgatttacaa cttgacgcta tgtgagctga atggcacaga ttggctagct     1920
gatagatttg attgggcagt ggagagcttt gtcatctttc ctgttttgac tcacattgtc     1980
tcctatggcg ccctcaccac cagccatttc cttgacacaa ttgctttagt cactgtgtct     2040
accgccgggt ttgttcacgg gcggtatgtc ctaagtagca tctacgcggt ctgtgccctg     2100
gctgcgttga cttgcttcgt cattaggttt gtgaagaatt gcatgtcctg gcgctactca     2160
tgtactagat ataccaactt tcttctggat actaagggca gactctatcg ttggcggtcg     2220
cctgtcatca tagagaagag gggcaaagtt gaggtcgaag gtcatctgat cgatctcaaa     2280
agagttgtgc ttgatggttc cgtggcaacc cctataacca gagtttcagc ggaacaatgg     2340
ggtcgtcctt ag                                                          2352

<210> SEQ ID NO 6
<211> LENGTH: 2352
<212> TYPE: DNA
<213> ORGANISM: Porcine reproductive and respiratory syndrome virus

<400> SEQUENCE: 6
cctgtcattg aaccaacttt aggcctgaat tgagatgaaa tggggtctat gcaaagcctt       60
tttgacaaaa ttggccaact ttttgtggat gctttcacgg agttcttggt gtccattgtt      120
gatatcatta tattttggc cattttgttt ggcttcacca tcgcaggttg gctggtggtc       180
ttttgcatca gattggtttg ctccgcgata ctccgtgcgc gccctgccat tcactctgag       240
caattacaga agatcctatg aggcctttct ctctcagtgc caggtggaca ttcccacctg       300
gggaactaaa catcctttgg ggatgctttg gcaccataag gtgtcaaccc tgattgatga      360
aatggtgtcg cgtcgaatgt accgcatcat ggaaaaagca ggacaggctg cctggaaaca      420
ggtagtgagc gaggctacgc tgtctcgcat tagtagtttg gatgtggtgg ctcattttca      480
gcatcttgcc gccattgaag ccgagacctg taaatatctg gcctctcggc tgcccatgct      540
acaccacctg cgcatgacag gtcaaatgt aaccatagtg tataatagta ctttgaatca      600
ggtgtttgct gttttcccaa cccctggttc ccggccaaag cttcatgatt ccagcaatg      660 gctaatagct gtacattcct ctatattttc ctctgttgca gcttcttgta ctcttttgt      720 tgtgctgtgg ttgcgggttc caatgctacg tactgttttt ggtttccgct ggttagggc      780 aatttttctt tcgaactcac ggtgaattac acggtgtgcc cgccttgcct cacccggcaa     840
gcagccgcag aggcctacga acccggcagg tccctttggt gcaggatagg gcatgatcga      900
tgtggggagg acgatcatga tgaactaggg tttgtggtgc cgtctggcct ctccagcgaa      960
ggccacttga ccagtgctta cgcctggttg gcgtccctgt ccttcagcta tcggcccag      1020 ttccatcccg agatattcgg gatagggaat gtgagtcgag tctatgttga catcaagcac     1080
caattcattt gcgctgttca tgatgggcag aacaccaccc tgccccacca tgacaacatt     1140
tcagccgtgc ttcagaccta ttaccagcat caggtcgacg ggggcaattg gtttcaccta     1200
```

-continued

| | |
|---|---|
| gaatgggtgc gtcccttctt ttcctcttgg ttggttttaa atgtctcttg gtttctcagg | 1260 |
| cgttcgcctg caagccatgt ttcagttcga gtctttcaga catcaagacc aacaccaccg | 1320 |
| cagcggcagg ctttgctgtc ctccaagaca tcagttgcct taggcatcgc aactcggcct | 1380 |
| ctgaggcgat tcgcaaagtc cctcagtgcc gcacggcgat agggacaccc gtgtatatca | 1440 |
| ctgtcacagc caatgttacc gatgagaatt atttgcattc ctctgatctt tcatgctttt | 1500 |
| cttcttgcct tttctatgct tctgagatga gtgaaaaggg atttaaggtg gtatttggca | 1560 |
| atgtgtcagg catcgtggca gtgtgcgtca acttcaccag ttacgtccaa catgtcaagg | 1620 |
| aatttaccca acgttccttg gtagttgacc atgtgcggct gctccatttc atgacgcccg | 1680 |
| agaccatgag gtgggcaact gtttttagcct gtcttttttac cattctgttg gcaatttgaa | 1740 |
| tgtttaagta tgttggggaa atgcttgacc gcgggctgtt gctcgcaatt gcttttttta | 1800 |
| tggtgtatcg tgccgtcttg ttttgttgcg ctcgtcagcg ccaacgggaa cagcggctca | 1860 |
| aatttacagc tgatttacaa cttgacgcta tgtgagctga atggcacaga ttggctagct | 1920 |
| aataaatttg actgggcagt ggagtgtttt gtcattttt ctgtgttgac tcacattgtc | 1980 |
| tcttatggtg ccctcactac tagccatttc cttgacacag tcggtctggt cactgtgtct | 2040 |
| accgctgggt ttgttcacgg gcggtatgtt ctgagtagca tgtacgcggt ctgtgccctg | 2100 |
| gctgcgttga tttgcttcgt cattaggctt gcgaagaatt gcatgtcctg gcgctactca | 2160 |
| tgtaccagat ataccaactt tcttctggac actaagggca gactctatcg ttggcggtcg | 2220 |
| cctgtcatca tagagaaaag gggcaaagtt gaggtcgaag gtcacctgat cgacctcaaa | 2280 |
| agagttgtgc ttgatggttc cgcggctacc cctgtaacca gagtttcagc ggaacaatgg | 2340 |
| agtcgtcctt ag | 2352 |

<210> SEQ ID NO 7
<211> LENGTH: 2352
<212> TYPE: DNA
<213> ORGANISM: Porcine reproductive and respiratory syndrome virus

<400> SEQUENCE: 7

| | |
|---|---|
| cccgtcattg aaccaacttt aggcctgaat tgaaatgaaa tggggtccgt gcaaagcctt | 60 |
| tttgacaaaa ttggccaact ttttgtggat gctttcacgg agttcctggt gtccattgtt | 120 |
| gatatcatca tattttggc cattttgttt ggcttcacca tcgccggttg ctggtggtc | 180 |
| ttttgcatca gattggtttg ctccgcgata ctccgtacgc gccctgccat tcactctgag | 240 |
| caattacaga agatcttatg aggcctttt atcccagtgc caagtggaca ttcccacctg | 300 |
| gggaactaaa catccttgg ggatgttttg gcaccataag gtgtcaaccc tgattgatga | 360 |
| aatggtgtcg cgtcgcatgt accgcatcat ggaaaaagca gggcaggctg cctggaaaca | 420 |
| ggtggtgagc gaggctacgc tgtcccgcat tagtagtttg gatgtggtgg ctcattttca | 480 |
| gcatcttgcc gccattgaag ccgagacttg taaatatttg gcctcccggc tgcccatgct | 540 |
| acataacctg cgcataacag ggtcaaatgt aaccatagtg tataatagta cttcggagca | 600 |
| ggtgttttgct attttcccaa cccctggttc ccggccaaag cttcatgatt ttcagcaatg | 660 |
| gttaatagct gtacattcct ccatattttc ctctgttgca gcttcttgta ctcttttgt | 720 |
| tgtgctgtgg ctgcgggttc caatgctacg tactgttttt ggtttccgct ggttagggg | 780 |
| aattttttcct tcgaactcat ggtgaattac acggtgtgtc caccttgcct cacccggcaa | 840 |
| gcagccgcag aggtctacga acccggtagg tctctttggt gcaggatagg gtatgaccga | 900 |
| tgtggggagg acgatcatga cgagctaggg tttatgatac cgcctggcct ctccagcgaa | 960 |

```
ggccacttga ctagtgttta cgcctggttg gcgttttgt ccttcagcta cacggcccag    1020
ttccatcccg agatattcgg datagggaat gtgagtcgag tttatgttga catcaaacat    1080
caactcattt gcgccgaaca tgacggacag aacgccacct tgcctcgtca tgacaatatt    1140
tcagccgtgt ttcagaccta ttaccaacat caagtcgatg gcggcaattg gtttcaccta    1200
gaatggcttc gtcccttctt ttcctcatgg ttggttttaa atgtctcttg gtatctcagg    1260
cgttcgcctg caaaccatgc ttcagttcga gtcttgcaga tattaagacc aacactaccg    1320
cagcggcaag ctttgctgtc ctccaagaca tcagttgcct taggcatcgc aactcggcct    1380
ctgaggcgat tcgcaaaatc cctcagtgcc gtacggcgat agggacaccc gtgtatatta    1440
ccatcacagc caatgtgaca gatgagaatt atttacattc ttctgatctc ctcatgcttt    1500
cttcttgcct tttctacgct tctgagatga gtgaaaaagg attcaaggtg gtatttggca    1560
atgtgtcagg catcgtggct gtgtgtgtca attttaccag ctacgtccaa catgtcaggg    1620
agtttaccca acgctccctg gtggtcgacc atgtgcggtt gctccatttc atgacacctg    1680
aaaccatgag gtgggcaact gttttagcct gtctttttgc cattctgctg caatttgaa    1740 tgtttaagta tgttggggaa atgcttgacc gcgggctgtt gctcgcgatt gctttctttg    1800
tggtgtatcg tgccgttctg ttttgctgtg ctcgccaacg ccagcgccaa cagcagctcc    1860
catctacagc tgatttacaa cttgacgcta tgtgagctga atggcacaga ttggctagct    1920
gataaatttg attgggcagt ggagagtttt gtcatctttc ccgttttgac tcacattgtc    1980
tcctatggtg ccctcactac tagccatctc cttgacacag tcgccttagt cactgtgtct    2040
accgccgggt tgttcacgg gcggtatgtc ctaagtagca tctacgcggt ctgtgccctg    2100
gctgcgttag cttgcttcgt cattaggttt gcaaagaatt gcatgtcctg gcgctattcg    2160
tgtaccagat ataccaactt tcttctggac actaagggca gactctatcg ttggcattcg    2220
cctgtcatca tagagaaaag gggcaaagtt gaggtcgaag gtcatctgat cgacctcaaa    2280
agagttgtgc ttgacggttc cgtggcaacc cctataacca gagtttcagc ggaacaatgg    2340
ggtcgtcctt ag                                                        2352
```

<210> SEQ ID NO 8
<211> LENGTH: 256
<212> TYPE: PRT
<213> ORGANISM: Porcine reproductive and respiratory syndrome virus

<400> SEQUENCE: 8

```
Met Lys Trp Gly Leu Cys Lys Ala Phe Leu Thr Lys Leu Ala Asn Phe
  1               5                  10                  15

Leu Trp Met Leu Ser Arg Ser Ser Trp Cys Pro Leu Leu Ile Ser Leu
             20                  25                  30

Tyr Phe Trp Pro Phe Cys Leu Ala Ser Pro Ser Gln Val Gly Trp Trp
         35                  40                  45

Ser Phe Ala Ser Asp Trp Phe Ala Pro Arg Tyr Ser Val Arg Ala Leu
     50                  55                  60

Pro Phe Thr Leu Ser Asn Tyr Arg Arg Ser Tyr Glu Ala Phe Leu Ser
 65                  70                  75                  80

Gln Cys Gln Val Asp Ile Pro Thr Trp Gly Thr Lys His Pro Leu Gly
                 85                  90                  95

Met Leu Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
```

-continued

```
                115                 120                 125
Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Met Leu Arg Met Thr Gly
                165                 170                 175

Ser Asn Val Thr Ile Val Tyr Asn Ser Thr Leu Asn Gln Val Phe Ala
                180                 185                 190

Val Phe Pro Thr Pro Gly Ser Arg Pro Lys Leu His Asp Phe Gln Gln
                195                 200                 205

Trp Leu Ile Ala Val His Ser Ser Ile Phe Ser Val Ala Ala Ser
    210                 215                 220

Cys Thr Leu Phe Val Val Leu Trp Leu Arg Val Pro Met Leu Arg Thr
225                 230                 235                 240

Val Phe Gly Phe Arg Trp Leu Gly Ala Ile Phe Leu Ser Asn Ser Arg
                245                 250                 255
```

<210> SEQ ID NO 9
<211> LENGTH: 256
<212> TYPE: PRT
<213> ORGANISM: Porcine reproductive and respiratory syndrome virus

<400> SEQUENCE: 9

```
Met Lys Trp Gly Pro Cys Lys Ala Phe Leu Thr Lys Leu Ala Asn Phe
1               5                   10                  15

Leu Trp Met Leu Ser Arg Ser Ser Trp Cys Pro Leu Leu Ile Ser Leu
                20                  25                  30

Tyr Phe Trp Pro Phe Cys Leu Ala Ser Pro Ser Pro Val Gly Trp Trp
            35                  40                  45

Ser Phe Ala Ser Asp Trp Phe Ala Pro Arg Tyr Ser Val Arg Ala Leu
        50                  55                  60

Pro Phe Thr Leu Ser Asn Tyr Arg Arg Ser Tyr Glu Ala Phe Leu Ser
65                  70                  75                  80

Gln Cys Gln Val Asp Ile Pro Thr Trp Gly Thr Lys His Pro Leu Gly
                85                  90                  95

Met Leu Trp His His Lys Val Ser Thr Leu Ile Asp Glu Met Val Ser
                100                 105                 110

Arg Arg Met Tyr Arg Ile Met Glu Lys Ala Gly Gln Ala Ala Trp Lys
            115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu Asn Gln Val Phe Ala
                180                 185                 190

Ile Phe Pro Thr Pro Gly Ser Arg Pro Lys Leu His Asp Phe Gln Gln
                195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Ile Leu Arg Ser
225                 230                 235                 240
```

```
Val Phe Gly Phe Arg Trp Leu Gly Ala Ile Phe Leu Ser Ser Ser Arg
                245                 250                 255

<210> SEQ ID NO 10
<211> LENGTH: 255
<212> TYPE: PRT
<213> ORGANISM: Porcine reproductive and respiratory syndrome virus

<400> SEQUENCE: 10

Met Lys Trp Gly Pro Cys Lys Ala Phe Leu Thr Lys Leu Ala Asn Phe
  1               5                  10                  15

Leu Trp Met Leu Ser Arg Ser Ser Trp Cys Pro Leu Leu Ile Ser Leu
                 20                  25                  30

Ser Phe Trp Pro Phe Cys Leu Ala Ser Pro Ser Pro Val Gly Trp Trp
             35                  40                  45

Ser Phe Ala Ser Asp Trp Phe Ala Pro Arg Tyr Ser Val Arg Ala Leu
         50                  55                  60

Pro Phe Thr Leu Ser Asn Tyr Arg Arg Ser Tyr Glu Ala Phe Leu Ser
 65                  70                  75                  80

Gln Cys Gln Val Asp Ile Pro Thr Trp Gly Thr Lys His Pro Leu Gly
                 85                  90                  95

Met Phe Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu Asn Arg Val Phe Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Ile Leu Arg Thr
225                 230                 235                 240

Val Phe Gly Phe Arg Trp Leu Gly Ala Ile Phe Leu Ser Asn Ser
                245                 250                 255

<210> SEQ ID NO 11
<211> LENGTH: 256
<212> TYPE: PRT
<213> ORGANISM: Porcine reproductive and respiratory syndrome virus

<400> SEQUENCE: 11

Met Lys Trp Gly Leu Cys Lys Ala Phe Leu Thr Lys Leu Ala Asn Phe
  1               5                  10                  15

Ser Trp Met Leu Ser Arg Ser Ser Trp Cys Pro Leu Leu Ile Ser Leu
                 20                  25                  30

Tyr Phe Trp Pro Phe Cys Leu Ala Ser Pro Ser Pro Val Gly Trp Trp
             35                  40                  45

Ser Phe Ala Ser Asp Trp Phe Ala Pro Arg Tyr Ser Val Arg Ala Leu
         50                  55                  60
```

```
Pro Phe Thr Leu Ser Asn Tyr Arg Arg Ser Tyr Glu Ala Phe Leu Ser
 65                  70                  75                  80

Gln Cys Gln Val Asp Ile Pro Thr Trp Gly Ile Lys His Pro Leu Gly
             85                  90                  95

Met Phe Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
            115                 120                 125

Gln Val Val Ser Glu Ala Thr Leu Ser Arg Ile Ser Ser Leu Asp Val
        130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu Asn Gln Val Leu Ala
            180                 185                 190

Ile Phe Pro Thr Pro Gly Ser Arg Pro Lys Leu His Asp Phe Gln Gln
            195                 200                 205

Trp Leu Ile Ala Val His Ser Ser Ile Phe Ser Ser Val Ala Ala Ser
        210                 215                 220

Cys Thr Leu Phe Val Val Leu Trp Leu Arg Val Pro Met Leu Arg Ile
225                 230                 235                 240

Ala Phe Gly Phe Arg Trp Leu Gly Ala Ile Phe Leu Ser Asn Ser Gln
                245                 250                 255

<210> SEQ ID NO 12
<211> LENGTH: 256
<212> TYPE: PRT
<213> ORGANISM: Porcine reproductive and respiratory syndrome virus

<400> SEQUENCE: 12

Met Lys Trp Gly Pro Cys Lys Ala Phe Leu Thr Lys Leu Ala Asn Phe
  1               5                  10                  15

Leu Trp Met Leu Ser Arg Ser Ser Trp Cys Pro Leu Leu Ile Ser Ser
             20                  25                  30

Tyr Phe Trp Pro Phe Cys Leu Ala Ser Pro Ser Pro Val Gly Trp Trp
         35                  40                  45

Ser Phe Ala Ser Asp Trp Phe Ala Pro Arg Tyr Ser Val Arg Ala Leu
     50                  55                  60

Pro Phe Thr Leu Ser Asn Tyr Arg Arg Ser Tyr Glu Ala Phe Leu Ser
 65                  70                  75                  80

Gln Cys Gln Val Asp Ile Pro Thr Trp Gly Thr Lys His Pro Leu Gly
             85                  90                  95

Met Phe Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
            115                 120                 125

Gln Val Val Ser Glu Ala Thr Leu Ser Arg Ile Ser Ser Leu Asp Val
        130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Ile Thr Gly
                165                 170                 175

Ser Asn Val Thr Ile Val Tyr Asn Ser Thr Ser Glu Gln Val Phe Ala
            180                 185                 190
```

```
Ile Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
        210                 215                 220

Cys Thr Leu Phe Val Val Leu Trp Leu Arg Val Pro Met Leu Arg Thr
225                 230                 235                 240

Val Phe Gly Phe Arg Trp Leu Gly Gly Ile Phe Pro Ser Asn Ser Trp
                245                 250                 255

<210> SEQ ID NO 13
<211> LENGTH: 256
<212> TYPE: PRT
<213> ORGANISM: Porcine reproductive and respiratory syndrome virus

<400> SEQUENCE: 13

Met Gln Trp Gly Pro Cys Lys Ala Phe Leu Thr Arg Ser Val Asn Phe
1                   5                   10                  15

Leu Trp Met Leu Ser Arg Ser Ser Trp Cys Pro Leu Leu Ile Ser Ser
                20                  25                  30

Tyr Phe Trp Pro Phe Cys Leu Ala Ser Pro Leu Pro Ala Gly Trp Trp
            35                  40                  45

Ser Phe Ala Ser Asp Trp Phe Ala Pro Arg Tyr Ser Val Arg Ala Leu
        50                  55                  60

Pro Phe Thr Leu Ser Asn Tyr Arg Arg Ser Tyr Glu Ala Phe Leu Ser
65                  70                  75                  80

Gln Cys Gln Val Asp Ile Pro Ala Trp Gly Thr Arg His Pro Leu Gly
                85                  90                  95

Met Leu Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Gly Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Ile Thr Gly
                165                 170                 175

Ser Asn Val Thr Ile Val His Asn Ser Thr Leu Asn Gln Val Phe Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Ser Ser Val Ala Ala Ser
        210                 215                 220

Cys Thr Leu Phe Val Val Leu Trp Leu Arg Met Pro Met Leu Arg Ser
225                 230                 235                 240

Val Phe Gly Phe Arg Trp Leu Gly Ala Ile Phe Pro Ser Ser Ser Trp
                245                 250                 255

<210> SEQ ID NO 14
<211> LENGTH: 256
<212> TYPE: PRT
<213> ORGANISM: Porcine reproductive and respiratory syndrome virus

<400> SEQUENCE: 14

Met Lys Trp Gly Pro Cys Lys Ala Phe Leu Thr Lys Leu Ala Asn Phe
1                   5                   10                  15
```

Leu Trp Met Leu Ser Arg Ser Ser Trp Cys Pro Leu Leu Ile Ser Leu
             20                  25                  30

Tyr Phe Trp Pro Phe Cys Leu Ala Ser Pro Ser Pro Val Gly Trp Trp
             35                  40                  45

Ser Phe Ala Ser Asp Trp Phe Ala Pro Arg Tyr Ser Val Arg Ala Leu
 50                  55                  60

Pro Phe Thr Leu Ser Asn Tyr Arg Arg Ser Tyr Glu Ala Phe Leu Ser
 65                  70                  75                  80

Gln Cys Gln Val Asp Ile Pro Thr Trp Gly Thr Lys His Pro Leu Gly
             85                  90                  95

Met Leu Trp His His Lys Val Ser Thr Leu Ile Asp Glu Met Val Ser
             100                 105                 110

Arg Arg Met Tyr Arg Ile Met Glu Lys Ala Gly Gln Ala Ala Trp Lys
             115                 120                 125

Gln Val Val Ser Glu Ala Thr Leu Ser Arg Ile Ser Ser Leu Asp Val
             130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
             165                 170                 175

Ser Asn Val Thr Ile Val Tyr Asn Ser Thr Leu Asn Gln Val Phe Ala
             180                 185                 190

Ile Phe Pro Thr Pro Gly Ser Arg Pro Lys Leu His Asp Phe Gln Gln
             195                 200                 205

Trp Leu Ile Ala Val His Ser Ser Ile Phe Ser Ser Val Ala Ala Ser
             210                 215                 220

Cys Thr Leu Phe Val Val Leu Trp Leu Arg Val Pro Ile Leu Arg Thr
225                 230                 235                 240

Val Phe Gly Phe Arg Trp Leu Gly Ala Ile Phe Leu Ser Asn Ser Gln
             245                 250                 255

<210> SEQ ID NO 15
<211> LENGTH: 249
<212> TYPE: PRT
<213> ORGANISM: Porcine reproductive and respiratory syndrome virus

<400> SEQUENCE: 15

Met Gln Trp Gly His Cys Gly Val Lys Ser Ala Ser Cys Ser Trp Thr
 1               5                  10                  15

Pro Ser Leu Ser Ser Leu Leu Val Trp Leu Ile Leu Pro Phe Ser Leu
             20                  25                  30

Pro Tyr Cys Leu Gly Ser Pro Ser Gln Asp Gly Tyr Trp Ser Phe Phe
             35                  40                  45

Ser Glu Trp Phe Ala Pro Arg Phe Ser Val Arg Ala Leu Pro Phe Thr
 50                  55                  60

Leu Pro Asn Tyr Arg Arg Ser Tyr Glu Gly Leu Leu Pro Asn Cys Arg
 65                  70                  75                  80

Pro Asp Val Pro Gln Phe Ala Val Lys His Pro Leu Gly Met Phe Trp
             85                  90                  95

His Met Arg Val Ser His Leu Ile Asp Glu Met Val Ser Arg Arg Ile
             100                 105                 110

Tyr Gln Thr Met Glu His Ser Gly Gln Ala Ala Trp Lys Gln Val Val
             115                 120                 125

Gly Glu Ala Thr Leu Thr Lys Leu Ser Gly Leu Asp Ile Val Thr His

```
            130                 135                 140
Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
                180                 185                 190

Gly Thr Arg Pro Lys Leu Thr Asp Phe Arg Gln Trp Leu Ile Ser Val
                195                 200                 205

His Ala Ser Ile Phe Ser Ser Val Ala Ser Val Thr Leu Phe Ile
                210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245

<210> SEQ ID NO 16
<211> LENGTH: 254
<212> TYPE: PRT
<213> ORGANISM: Porcine reproductive and respiratory syndrome virus

<400> SEQUENCE: 16

Met Ala Asn Ser Cys Thr Phe Leu Tyr Ile Phe Leu Cys Cys Ser Phe
  1               5                  10                  15

Leu Tyr Ser Phe Cys Cys Ala Val Val Ala Gly Ser Asn Ala Thr Tyr
                 20                  25                  30

Cys Phe Trp Phe Pro Leu Val Arg Gly Asn Phe Ser Phe Glu Leu Thr
             35                  40                  45

Val Asn Tyr Thr Val Cys Pro Pro Cys Leu Thr Arg Gln Ala Ala Ala
         50                  55                  60

Glu Ala Tyr Glu Pro Gly Arg Ser Leu Trp Cys Arg Ile Gly His Asp
 65                  70                  75                  80

Arg Cys Gly Glu Asp Asp His Asp Glu Leu Gly Phe Val Val Pro Ser
                 85                  90                  95

Gly Leu Ser Ser Glu Gly His Leu Thr Ser Ala Tyr Ala Trp Leu Ala
                100                 105                 110

Ser Leu Ser Phe Ser Tyr Thr Thr Gln Phe His Pro Glu Ile Phe Gly
            115                 120                 125

Ile Gly Asn Val Ser Arg Val Tyr Val Asp Ile Lys His Gln Phe Ile
        130                 135                 140

Cys Ala Val His Asp Gly Gln Asn Thr Thr Leu Pro His His Asp Asn
145                 150                 155                 160

Ile Ser Ala Val Leu Gln Thr Tyr Tyr Gln His Gln Val Asp Gly Gly
                165                 170                 175

Asn Trp Phe His Leu Glu Trp Val Arg Pro Phe Phe Ser Ser Trp Leu
                180                 185                 190

Val Leu Asn Val Ser Trp Phe Leu Arg Arg Ser Pro Ala Ser His Val
            195                 200                 205

Ser Val Arg Val Phe Gln Thr Ser Arg Pro Thr Pro Pro Gln Arg Gln
        210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Ala Arg Arg
                245                 250
```

<210> SEQ ID NO 17
<211> LENGTH: 254
<212> TYPE: PRT
<213> ORGANISM: Porcine reproductive and respiratory syndrome virus

<400> SEQUENCE: 17

```
Met Ala Asn Ser Cys Thr Phe Leu Tyr Ile Phe Leu Cys Cys Ser Phe
  1               5                  10                  15

Leu Tyr Ser Phe Cys Cys Ala Val Val Ala Gly Ser Asn Ala Thr Tyr
             20                  25                  30

Cys Phe Trp Phe Pro Leu Val Arg Gly Asn Phe Ser Phe Glu Leu Thr
         35                  40                  45

Val Asn Tyr Thr Val Cys Pro Pro Cys Leu Thr Arg Gln Ala Ala Thr
     50                  55                  60

Glu Ala Tyr Glu Pro Gly Arg Ser Leu Trp Cys Arg Ile Gly Tyr Asp
 65                  70                  75                  80

Arg Cys Gly Glu Asp Asp His Asp Glu Leu Gly Phe Val Val Pro Ser
                 85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Gln Val Tyr Val Asp Ile Arg His Gln Phe Ile
    130                 135                 140

Cys Ala Val His Asp Gly Gln Asn Ala Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Ser His Val
        195                 200                 205

Ser Val Arg Val Leu Gln Thr Leu Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Val Val Arg Arg
                245                 250
```

<210> SEQ ID NO 18
<211> LENGTH: 254
<212> TYPE: PRT
<213> ORGANISM: Porcine reproductive and respiratory syndrome virus

<400> SEQUENCE: 18

```
Met Ala Asn Ser Cys Ala Phe Leu His Ile Phe Leu Cys Cys Ser Phe
  1               5                  10                  15

Leu Tyr Ser Leu Cys Cys Ala Val Val Ala Gly Ser Asn Thr Thr Tyr
             20                  25                  30

Cys Phe Trp Phe Pro Leu Val Arg Gly Asn Phe Ser Phe Glu Leu Ile
         35                  40                  45

Val Asn Tyr Thr Val Cys Pro Pro Cys Leu Thr Arg Gln Ala Ala Ala
     50                  55                  60

Glu Ala Tyr Glu Pro Gly Arg Ser Leu Trp Cys Arg Ile Gly Tyr Asp
 65                  70                  75                  80
```

Arg Cys Gly Glu Asp Asp His Asp Glu Leu Gly Phe Met Ile Pro Ser
                85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
            115                 120                 125

Ile Gly Asn Val Ser Arg Val Tyr Val Asp Ile Lys His Gln Leu Ile
    130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
                180                 185                 190

Val Leu Asn Val Ser Trp Phe Leu Arg Arg Ser Pro Ala Asn His Val
            195                 200                 205

Ser Val Arg Val Leu Gln Thr Leu Arg Pro Thr Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250

<210> SEQ ID NO 19
<211> LENGTH: 254
<212> TYPE: PRT
<213> ORGANISM: Porcine reproductive and respiratory syndrome virus

<400> SEQUENCE: 19

Met Val Asn Ser Cys Thr Phe Leu His Ile Phe Leu Cys Cys Ser Phe
 1               5                  10                  15

Leu Tyr Ser Phe Cys Cys Ala Val Ala Ala Gly Ser Asn Ala Thr Tyr
                20                  25                  30

Cys Phe Trp Phe Pro Leu Val Arg Gly Asn Phe Ser Phe Glu Leu Met
            35                  40                  45

Val Asn Tyr Thr Val Cys Pro Pro Cys Leu Thr Arg Gln Ala Ala Ala
    50                  55                  60

Glu Val Tyr Glu Pro Gly Arg Ser Leu Trp Cys Arg Ile Gly Tyr Asp
65                  70                  75                  80

Arg Cys Gly Glu Asp Asp His Asp Glu Leu Gly Phe Met Ile Pro Pro
                85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
            115                 120                 125

Ile Gly Asn Val Ser Arg Val Tyr Val Asp Ile Lys His Gln Leu Ile
    130                 135                 140

Cys Ala Glu His Asp Gly Gln Asn Ala Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
                180                 185                 190

Val Leu Asn Val Ser Trp Tyr Leu Arg Arg Ser Pro Ala Asn His Ala
            195                 200                 205

```
Ser Val Arg Val Leu Gln Ile Leu Arg Pro Thr Leu Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250

<210> SEQ ID NO 20
<211> LENGTH: 254
<212> TYPE: PRT
<213> ORGANISM: Porcine reproductive and respiratory syndrome virus

<400> SEQUENCE: 20

Met Val Asn Ser Cys Thr Phe Leu His Ile Phe Leu Cys Cys Ser Phe
1               5                   10                  15

Leu Tyr Ser Phe Cys Cys Ala Val Ala Gly Ser Asn Thr Thr Phe
            20                  25                  30

Cys Phe Trp Phe Pro Leu Val Arg Gly Asn Phe Ser Phe Glu Leu Thr
            35                  40                  45

Val Asn Tyr Thr Val Cys Pro Pro Cys Leu Thr Arg Gln Ala Ala Ala
        50                  55                  60

Glu Ile Tyr Glu Pro Gly Arg Ser Leu Trp Cys Arg Ile Gly Tyr Asp
65                  70                  75                  80

Arg Cys Gly Glu Asp Asp His Asp Glu Leu Gly Phe Met Val Pro Pro
                85                  90                  95

Gly Phe Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Arg Val Tyr Val Asp Ile Lys His Gln Leu Ile
    130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Asn His Val
        195                 200                 205

Ser Val Arg Val Leu Gln Ile Leu Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250

<210> SEQ ID NO 21
<211> LENGTH: 254
<212> TYPE: PRT
<213> ORGANISM: Porcine reproductive and respiratory syndrome virus

<400> SEQUENCE: 21

Met Ala Asn Ser Cys Thr Phe Leu His Ile Leu Leu Cys Cys Ser Phe
1               5                   10                  15

Leu Tyr Ser Phe Cys Cys Val Val Val Thr Asp Ala Asn Ala Thr Phe
            20                  25                  30
```

```
Cys Phe Trp Phe Pro Leu Val Arg Gly Asn Phe Ser Phe Glu Leu Met
         35                  40                  45
Val Asn Tyr Thr Val Cys Pro Pro Cys Leu Thr Arg Gln Ala Ala Ala
 50                  55                  60
Gln Ile Tyr Glu Pro Asn Arg Ser Leu Trp Cys Arg Ile Gly Asn Asp
 65                  70                  75                  80
Arg Cys Gly Glu Asp Asp His Asp Glu Leu Gly Phe Thr Val Pro Pro
                 85                  90                  95
Gly Leu Ser Lys Glu Val His Leu Thr Ser Val Tyr Ala Trp Leu Ala
             100                 105                 110
Phe Leu Ser Phe Ser Tyr Thr Ala Gln Phe His Pro Glu Ile Phe Gly
             115                 120                 125
Ile Gly Asn Val Ser Lys Val Tyr Val Asp Ile Asn His Gln Leu Ile
         130                 135                 140
Cys Ala Val His Asp Gly Gln Asn Thr Thr Leu Pro Arg His Asp Asn
145                 150                 155                 160
Ile Ser Ala Val Phe Gln Thr Tyr Tyr Gln His Gln Val Asp Gly Gly
                 165                 170                 175
Asn Trp Phe His Leu Glu Trp Leu Arg Pro Phe Phe Ser Ser Trp Leu
             180                 185                 190
Val Leu Asn Val Ser Trp Phe Leu Arg Arg Ser Pro Ala Ser His Val
             195                 200                 205
Ser Val Arg Val Phe Gln Thr Ser Arg Pro Thr Pro Arg Gln Gln
         210                 215                 220
Ile Ser Leu Ser Ser Arg Thr Ser Ala Ala Leu Gly Met Ala Thr Arg
225                 230                 235                 240
Pro Leu Arg Arg Phe Ala Lys Ser Leu Ser Ala Ala Arg Arg
                 245                 250

<210> SEQ ID NO 22
<211> LENGTH: 254
<212> TYPE: PRT
<213> ORGANISM: Porcine reproductive and respiratory syndrome virus

<400> SEQUENCE: 22

Met Val Asn Ser Cys Thr Phe Leu His Ile Phe Leu Cys Cys Ser Phe
 1               5                  10                  15
Leu Tyr Ser Phe Cys Cys Ala Val Val Ala Gly Ser Asn Thr Thr Tyr
             20                  25                  30
Cys Phe Trp Phe Pro Leu Val Arg Gly Asn Phe Ser Phe Glu Leu Thr
         35                  40                  45
Val Asn Tyr Thr Val Cys Pro Pro Cys Leu Thr Arg Gln Ala Ala Thr
 50                  55                  60
Glu Ile Tyr Glu Pro Gly Arg Ser Leu Trp Cys Arg Ile Gly Tyr Asp
 65                  70                  75                  80
Arg Cys Gly Glu Asp Asp His Asp Glu Leu Gly Phe Met Ile Pro Pro
                 85                  90                  95
Gly Leu Ser Ser Glu Gly His Leu Thr Gly Val Tyr Ala Trp Leu Ala
             100                 105                 110
Phe Leu Ser Phe Ser Tyr Thr Ala Gln Phe His Pro Glu Ile Phe Gly
             115                 120                 125
Ile Gly Asn Val Ser Arg Val Tyr Val Asp Ile Lys His Gln Leu Ile
         130                 135                 140
Cys Ala Glu His Asp Gly Gln Asn Thr Thr Leu Pro Arg His Asp Asn
```

```
                    145                 150                 155                 160
Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Asn His Val
        195                 200                 205

Ser Val Arg Val Leu Gln Ile Leu Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250

<210> SEQ ID NO 23
<211> LENGTH: 265
<212> TYPE: PRT
<213> ORGANISM: Porcine reproductive and respiratory syndrome virus

<400> SEQUENCE: 23

Met Ala His Gln Cys Ala Arg Phe His Phe Leu Cys Gly Phe Ile
  1               5                  10                  15

Cys Tyr Leu Val His Ser Ala Leu Ala Ser Asn Ser Ser Ser Thr Leu
                 20                  25                  30

Cys Phe Trp Phe Pro Leu Ala His Gly Asn Thr Ser Phe Glu Leu Thr
             35                  40                  45

Ile Asn Tyr Thr Ile Cys Met Pro Cys Ser Thr Ser Gln Ala Ala Arg
         50                  55                  60

Gln Arg Leu Glu Pro Gly Arg Asn Met Trp Cys Lys Ile Gly His Asp
 65                  70                  75                  80

Arg Cys Glu Glu Arg Asp His Asp Glu Leu Leu Met Ser Ile Pro Ser
                 85                  90                  95

Gly Tyr Asp Asn Leu Lys Leu Glu Gly Tyr Tyr Ala Trp Leu Ala Phe
                100                 105                 110

Leu Ser Phe Ser Tyr Ala Ala Gln Phe His Pro Glu Leu Phe Gly Ile
            115                 120                 125

Gly Asn Val Ser Arg Val Phe Val Asp Lys Arg His Gln Phe Ile Cys
        130                 135                 140

Ala Glu His Asp Gly His Asn Ser Thr Val Ser Thr Gly His Asn Ile
145                 150                 155                 160

Ser Ala Leu Tyr Ala Ala Tyr Tyr His His Gln Ile Asp Gly Gly Asn
                165                 170                 175

Trp Phe His Leu Glu Trp Leu Arg Pro Leu Phe Ser Ser Trp Leu Val
            180                 185                 190

Leu Asn Ile Ser Trp Phe Leu Arg Arg Ser Pro Val Ser Pro Val Ser
        195                 200                 205

Arg Arg Ile Tyr Gln Ile Leu Arg Pro Thr Arg Pro Arg Leu Pro Val
    210                 215                 220

Ser Trp Ser Phe Arg Thr Ser Ile Val Ser Asp Leu Thr Gly Ser Gln
225                 230                 235                 240

Gln Arg Lys Arg Lys Phe Pro Ser Glu Ser Arg Pro Asn Val Val Lys
                245                 250                 255

Pro Ser Val Leu Pro Ser Thr Ser Arg
                260                 265
```

```
<210> SEQ ID NO 24
<211> LENGTH: 178
<212> TYPE: PRT
<213> ORGANISM: Porcine reproductive and respiratory syndrome virus

<400> SEQUENCE: 24

Met Gly Ala Ser Leu Leu Phe Leu Val Gly Phe Lys Cys Leu Leu
  1               5                  10                  15

Val Ser Gln Ala Phe Ala Cys Lys Pro Cys Phe Ser Ser Leu Ser
                 20                  25                  30

Asp Ile Lys Thr Asn Thr Thr Ala Ala Gly Phe Ala Val Leu Gln
                 35                  40                  45

Asp Ile Ser Cys Leu Arg His Arg Asn Ser Ala Ser Glu Ala Ile Arg
         50                  55                  60

Lys Val Pro Gln Cys Arg Thr Ala Ile Gly Thr Pro Val Tyr Ile Thr
 65                  70                  75                  80

Val Thr Ala Asn Val Thr Asp Glu Asn Tyr Leu His Ser Ser Asp Leu
                 85                  90                  95

Leu Met Leu Ser Ser Cys Leu Phe Tyr Ala Ser Glu Met Ser Glu Lys
                100                 105                 110

Gly Phe Lys Val Val Phe Gly Asn Val Ser Gly Ile Val Ala Val Cys
                115                 120                 125

Val Asn Phe Thr Ser Tyr Val Gln His Val Lys Glu Phe Thr Gln Arg
            130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Thr Ile Leu Leu
                165                 170                 175

Ala Ile

<210> SEQ ID NO 25
<211> LENGTH: 178
<212> TYPE: PRT
<213> ORGANISM: Porcine reproductive and respiratory syndrome virus

<400> SEQUENCE: 25

Met Ala Ser Ser Leu Leu Phe Leu Val Val Gly Phe Lys Cys Leu Leu
  1               5                  10                  15

Val Ser Gln Ala Phe Ala Cys Lys Pro Cys Phe Ser Ser Leu Ala
                 20                  25                  30

Asp Ile Lys Thr Asn Thr Thr Ala Ala Ala Ser Phe Ala Val Leu Gln
                 35                  40                  45

Asp Ile Ser Cys Leu Arg His Arg Asp Ser Ala Ser Glu Ala Ile Arg
         50                  55                  60

Lys Ile Pro Gln Cys Arg Thr Ala Ile Gly Thr Pro Val Tyr Val Thr
 65                  70                  75                  80

Ile Thr Ala Asn Val Thr Asp Glu Asn Tyr Leu His Ser Ser Asp Leu
                 85                  90                  95

Leu Met Leu Ser Ser Cys Leu Phe Tyr Ala Ser Glu Met Ser Glu Lys
                100                 105                 110

Gly Phe Lys Val Val Phe Gly Asn Val Ser Gly Ile Val Ala Val Cys
                115                 120                 125

Val Asn Phe Thr Ser Tyr Val Gln His Val Lys Glu Phe Thr Gln Arg
            130                 135                 140

Ser Leu Val Val Asp His Val Arg Leu Leu His Phe Met Thr Pro Glu
```

145                 150                 155                 160

Thr Met Arg Trp Ala Thr Val Leu Ala Cys Leu Phe Ala Ile Leu Leu
                165                 170                 175

Ala Ile

<210> SEQ ID NO 26
<211> LENGTH: 178
<212> TYPE: PRT
<213> ORGANISM: Porcine reproductive and respiratory syndrome virus

<400> SEQUENCE: 26

Met Ala Ala Ser Leu Leu Phe Leu Leu Val Gly Phe Lys Cys Leu Leu
 1               5                  10                  15

Val Ser Gln Ala Phe Ala Cys Lys Pro Cys Phe Ser Ser Leu Ala
                20                  25                  30

Asp Ile Lys Thr Asn Thr Thr Ala Ala Gly Phe Ala Val Leu Gln
                35                  40                  45

Asp Ile Ser Cys Leu Arg Tyr Arg Asn Ser Ala Ser Glu Ala Phe Arg
         50                  55                  60

Lys Ile Pro Gln Cys Arg Thr Ala Ile Gly Thr Pro Met Tyr Ile Thr
 65                  70                  75                  80

Val Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
                100                 105                 110

Gly Phe Lys Val Val Phe Gly Asn Val Ser Gly Ile Val Ala Val Cys
                115                 120                 125

Val Asn Phe Thr Ser Tyr Val Gln His Val Lys Glu Phe Thr Gln Arg
                130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile

<210> SEQ ID NO 27
<211> LENGTH: 178
<212> TYPE: PRT
<213> ORGANISM: Porcine reproductive and respiratory syndrome virus

<400> SEQUENCE: 27

Met Ala Ser Ser Leu Leu Phe Leu Met Val Gly Phe Lys Cys Leu Leu
 1               5                  10                  15

Val Ser Gln Ala Phe Ala Cys Lys Pro Cys Phe Ser Ser Leu Ala
                20                  25                  30

Asp Ile Lys Thr Asn Thr Thr Ala Ala Ser Phe Ala Val Leu Gln
                35                  40                  45

Asp Ile Ser Cys Leu Arg His Arg Asn Ser Ala Ser Glu Ala Ile Arg
         50                  55                  60

Lys Ile Pro Gln Cys Arg Thr Ala Ile Gly Thr Pro Val Tyr Ile Thr
 65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
                100                 105                 110

-continued

```
Gly Phe Lys Val Val Phe Gly Asn Val Ser Gly Ile Val Ala Val Cys
            115                 120                 125

Val Asn Phe Thr Ser Tyr Val Gln His Val Arg Glu Phe Thr Gln Arg
        130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile

<210> SEQ ID NO 28
<211> LENGTH: 178
<212> TYPE: PRT
<213> ORGANISM: Porcine reproductive and respiratory syndrome virus

<400> SEQUENCE: 28

Met Ala Ser Ser Leu Leu Phe Leu Met Val Gly Phe Lys Cys Leu Leu
  1               5                  10                  15

Val Ser Gln Ala Phe Ala Cys Lys Pro Cys Phe Ser Ser Ser Leu Ala
                20                  25                  30

Asp Ile Lys Thr Asn Thr Thr Ala Ala Ala Ser Phe Ala Val Leu Gln
            35                  40                  45

Asp Ile Gly Cys Leu Arg His Arg Asp Ser Ala Ser Glu Ala Ile Arg
        50                  55                  60

Lys Ile Pro Gln Cys Arg Thr Ala Ile Gly Thr Pro Val Tyr Ile Thr
 65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125

Val Asn Phe Thr Ser Tyr Val Gln His Val Arg Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile

<210> SEQ ID NO 29
<211> LENGTH: 178
<212> TYPE: PRT
<213> ORGANISM: Porcine reproductive and respiratory syndrome virus

<400> SEQUENCE: 29

Met Ala Ala Ser Leu Leu Phe Leu Met Val Gly Phe Lys Cys Leu Leu
  1               5                  10                  15

Val Ser Gln Ala Phe Ala Cys Lys Pro Cys Phe Ser Ser Ser Leu Ala
                20                  25                  30

Asp Ile Lys Thr Asn Thr Thr Ala Ala Ala Ser Phe Ala Val Leu Gln
            35                  40                  45

Asp Ile Ser Cys Leu Arg His Arg Asn Ser Ala Ser Glu Ala Ile Arg
        50                  55                  60

Lys Ile Pro Gln Cys Arg Thr Ala Ile Gly Thr Pro Met Tyr Ile Thr
 65                  70                  75                  80
```

```
Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
            100                 105                 110

Gly Phe Glu Val Val Phe Gly Asn Val Ser Gly Ile Val Ala Val Cys
            115                 120                 125

Val Asn Phe Thr Ser Tyr Val Gln His Val Arg Glu Phe Thr Gln Arg
    130                 135                 140

Ser Leu Met Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
            165                 170                 175

Ala Ile

<210> SEQ ID NO 30
<211> LENGTH: 178
<212> TYPE: PRT
<213> ORGANISM: Porcine reproductive and respiratory syndrome virus

<400> SEQUENCE: 30

Met Ala Ala Ser Leu Leu Phe Leu Leu Val Gly Phe Glu Cys Leu Leu
1               5                   10                  15

Val Ser Gln Ala Phe Ala Cys Lys Pro Cys Phe Ser Ser Ser Leu Ser
            20                  25                  30

Asp Ile Lys Thr Asn Thr Thr Ala Ala Ala Asn Phe Ala Val Leu Gln
            35                  40                  45

Asp Ile Gly Cys Leu Arg His Gly Asn Ser Thr Thr Glu Ala Phe Arg
    50                  55                  60

Lys Ile Pro Gln Cys Arg Thr Ala Ile Gly Thr Pro Val Tyr Ile Thr
65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Thr Val Ala Val Cys
            115                 120                 125

Ile Asn Phe Thr Ser Tyr Val Gln His Val Lys Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
            165                 170                 175

Ala Ile

<210> SEQ ID NO 31
<211> LENGTH: 183
<212> TYPE: PRT
<213> ORGANISM: Porcine reproductive and respiratory syndrome virus

<400> SEQUENCE: 31

Met Ala Ala Ala Thr Leu Phe Phe Leu Ala Gly Ala Gln His Ile Met
1               5                   10                  15

Val Ser Glu Ala Phe Ala Cys Lys Pro Cys Phe Ser Thr His Leu Ser
            20                  25                  30

Asp Ile Glu Thr Asn Thr Thr Ala Ala Ala Gly Phe Met Val Leu Gln
```

```
                35                  40                  45
Asp Ile Asn Cys Phe Arg Pro His Gly Val Ser Ala Ala Gln Glu Lys
        50                  55                  60

Ile Ser Phe Gly Lys Ser Ser Gln Cys Arg Glu Ala Val Gly Thr Pro
 65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
               100                 105                 110

Met Ser Glu Lys Gly Phe Lys Val Ile Phe Gly Asn Val Ser Gly Val
           115                 120                 125

Val Ser Ala Cys Val Asn Phe Thr Asp Tyr Val Ala His Val Thr Gln
       130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
               165                 170                 175

Phe Ala Ile Leu Leu Ala Ile
           180

<210> SEQ ID NO 32
<211> LENGTH: 199
<212> TYPE: PRT
<213> ORGANISM: Porcine reproductive and respiratory syndrome virus

<400> SEQUENCE: 32

Met Leu Gly Lys Cys Leu Thr Ala Gly Cys Cys Ser Gln Leu Leu Phe
 1               5                  10                  15

Leu Trp Cys Ile Val Pro Ser Cys Phe Val Ala Leu Val Ser Ala Asn
                20                  25                  30

Gly Asn Ser Gly Ser Asn Leu Gln Leu Ile Tyr Asn Leu Thr Leu Cys
            35                  40                  45

Glu Leu Asn Gly Thr Asp Trp Leu Ala Asn Lys Phe Asp Trp Ala Val
        50                  55                  60

Glu Cys Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                85                  90                  95

Ser Thr Ala Gly Phe Val His Gly Arg Tyr Val Leu Ser Ser Met Tyr
           100                 105                 110

Ala Val Cys Ala Leu Ala Ala Leu Ile Cys Phe Val Ile Arg Leu Ala
       115                 120                 125

Lys Asn Cys Met Ser Trp Arg Tyr Ser Cys Thr Arg Tyr Thr Asn Phe
   130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
               165                 170                 175

Lys Arg Val Val Leu Asp Gly Ser Ala Ala Thr Pro Val Thr Arg Val
           180                 185                 190

Ser Ala Glu Gln Trp Arg Pro
       195

<210> SEQ ID NO 33
<211> LENGTH: 199
```

```
<212> TYPE: PRT
<213> ORGANISM: Porcine reproductive and respiratory syndrome virus

<400> SEQUENCE: 33

Met Leu Glu Lys Cys Leu Thr Ala Gly Cys Cys Ser Arg Leu Leu Ser
 1               5                  10                  15

Leu Trp Cys Ile Val Pro Phe Cys Phe Ala Val Leu Ala Asn Ala Ser
             20                  25                  30

Asn Asp Ser Ser Ser His Leu Gln Leu Ile Tyr Asn Leu Thr Leu Cys
         35                  40                  45

Glu Leu Asn Gly Thr Asp Trp Leu Ala Asn Lys Phe Asp Trp Ala Val
     50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr Val Leu Ser Ser Ile Tyr
                100                 105                 110

Ala Val Cys Ala Leu Ala Ala Leu Thr Cys Phe Val Ile Arg Phe Ala
            115                 120                 125

Lys Asn Cys Met Ser Trp Arg Tyr Ala Cys Thr Arg Tyr Thr Asn Phe
        130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Gly Arg Pro
            195

<210> SEQ ID NO 34
<211> LENGTH: 199
<212> TYPE: PRT
<213> ORGANISM: Porcine reproductive and respiratory syndrome virus

<400> SEQUENCE: 34

Met Leu Gly Lys Cys Leu Thr Ala Gly Tyr Cys Ser Ser Leu Leu Phe
 1               5                  10                  15

Leu Trp Cys Ile Val Pro Ser Trp Phe Val Ala Leu Ala Ser Ala Asn
             20                  25                  30

Ser Ser Asn Ser Ser His Leu Gln Leu Ile Tyr Asn Leu Thr Leu Cys
         35                  40                  45

Glu Leu Asn Gly Thr Asp Trp Leu Ala Gly Glu Phe Asp Trp Ala Val
     50                  55                  60

Glu Cys Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe Ser His Gly Arg Tyr Val Leu Ser Ser Ile Tyr
                100                 105                 110

Ala Val Cys Ala Leu Ala Ala Leu Ile Cys Phe Val Ile Arg Phe Thr
            115                 120                 125

Lys Asn Cys Met Ser Trp Arg Tyr Ser Cys Thr Arg Tyr Thr Asn Phe
        130                 135                 140
```

```
Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Ala Ala Thr Pro Ile Thr Lys Val
                180                 185                 190

Ser Ala Glu Gln Gly Arg Pro
        195
```

<210> SEQ ID NO 35
<211> LENGTH: 199
<212> TYPE: PRT
<213> ORGANISM: Porcine reproductive and respiratory syndrome virus

<400> SEQUENCE: 35

```
Met Leu Gly Lys Cys Leu Thr Ala Gly Cys Cys Ser Arg Leu Leu Ser
1               5                   10                  15

Leu Trp Cys Ile Val Pro Phe Cys Phe Ala Val Leu Ala Asn Ala Ser
                20                  25                  30

Ala Asn Ser Ser Ser His Leu Gln Leu Ile Tyr Asn Leu Thr Leu Cys
            35                  40                  45

Glu Leu Asn Gly Thr Asp Trp Leu Ala Asp Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Leu Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Ala Cys Phe Val Ile Arg Phe Ala
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp His Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
                180                 185                 190

Ser Ala Glu Gln Gly Arg Pro
        195
```

<210> SEQ ID NO 36
<211> LENGTH: 199
<212> TYPE: PRT
<213> ORGANISM: Porcine reproductive and respiratory syndrome virus

<400> SEQUENCE: 36

```
Met Leu Gly Lys Cys Leu Thr Val Gly Cys Cys Ser Arg Leu Leu Ser
1               5                   10                  15

Leu Trp Cys Ile Val Pro Phe Cys Phe Thr Val Leu Ala Asp Ala His
                20                  25                  30

Ser Asn Ser Ser Ser His Leu Gln Leu Ile Tyr Asn Leu Thr Leu Cys
            35                  40                  45

Glu Leu Asn Gly Thr Asp Trp Leu Ala Asp Arg Phe Asp Trp Ala Val
    50                  55                  60
```

```
Glu Ser Phe Val Ile Phe Pro Val Leu Thr His Ile Val Ser Tyr Gly
 65                  70                  75                  80

Ala Leu Thr Thr Ser His Phe Leu Asp Thr Ile Ala Leu Val Thr Val
                 85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Val
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Gly Arg Pro
            195

<210> SEQ ID NO 37
<211> LENGTH: 199
<212> TYPE: PRT
<213> ORGANISM: Porcine reproductive and respiratory syndrome virus

<400> SEQUENCE: 37

Met Leu Gly Lys Cys Leu Thr Ala Gly Cys Cys Ser Arg Leu Leu Ser
  1               5                  10                  15

Leu Trp Phe Ile Val Pro Phe Cys Phe Ala Val Leu Ala Ser Ala Ser
                 20                  25                  30

Asn Ser Ser Ser His Leu Gln Leu Ile Tyr Asn Leu Thr Leu Cys
             35                  40                  45

Glu Leu Asn Gly Thr Asp Trp Leu Ala Asn Lys Phe Asp Trp Ala Val
 50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Ile Ile Arg Phe Ala
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Gly Arg Pro
            195

<210> SEQ ID NO 38
<211> LENGTH: 198
<212> TYPE: PRT
<213> ORGANISM: Porcine reproductive and respiratory syndrome virus
```

<400> SEQUENCE: 38

```
Met Leu Gly Lys Cys Leu Thr Ala Gly Cys Cys Ser Arg Ser Leu Phe
 1               5                  10                  15

Leu Trp Cys Ile Val Pro Phe Cys Leu Ala Ala Leu Val Ser Ala Asn
                20                  25                  30

Asn Ser Ser Ser His Leu Gln Leu Ile Tyr Asn Leu Thr Leu Cys Glu
            35                  40                  45

Leu Asn Gly Thr Asp Trp Leu Ala Asn Lys Phe Asp Trp Ala Val Glu
        50                  55                  60

Ser Phe Val Ile Phe Pro Val Leu Thr His Ile Val Ser Tyr Gly Ala
 65                  70                  75                  80

Leu Thr Thr Ser His Phe Leu Asp Thr Val Gly Leu Val Thr Val Ser
                85                  90                  95

Thr Ala Gly Phe His His Gly Arg Tyr Val Leu Ser Ser Ile Tyr Ala
            100                 105                 110

Val Cys Ala Leu Ala Ala Phe Ile Cys Phe Val Ile Arg Phe Ala Lys
        115                 120                 125

Asn Cys Met Ser Trp Arg Tyr Ser Cys Thr Arg Tyr Thr Asn Phe Leu
130                 135                 140

Leu Asp Thr Lys Gly Arg Leu Tyr Arg Trp Arg Ser Pro Val Ile Ile
145                 150                 155                 160

Glu Lys Gly Gly Lys Val Glu Val Glu Gly His Leu Ile Asp Leu Lys
                165                 170                 175

Lys Val Val Leu Asp Gly Ser Ala Ala Thr Pro Leu Thr Arg Val Ser
                180                 185                 190

Ala Glu Gln Gly Arg Pro
            195
```

<210> SEQ ID NO 39
<211> LENGTH: 200
<212> TYPE: PRT
<213> ORGANISM: Porcine reproductive and respiratory syndrome virus

<400> SEQUENCE: 39

```
Met Arg Cys Ser His Lys Leu Gly Arg Phe Leu Thr Pro His Ser Cys
 1               5                  10                  15

Phe Trp Trp Leu Phe Leu Leu Cys Thr Gly Leu Ser Trp Ser Phe Ser
                20                  25                  30

Asp Asn Gly Gly Asp Ser Ser Thr Tyr Gln Tyr Ile Tyr Asn Leu Thr
            35                  40                  45

Ile Cys Glu Leu Asn Gly Thr Asp Trp Leu Ser His Phe Gly Trp
        50                  55                  60

Ala Val Glu Thr Phe Val Leu Tyr Pro Val Ala Thr His Ile Leu Ser
 65                  70                  75                  80

Leu Gly Phe Leu Thr Thr Ser His Phe Phe Asp Ala Leu Gly Leu Gly
                85                  90                  95

Ala Val Ser Thr Ala Gly Phe Val Gly Gly Arg Tyr Val Leu Cys Ser
            100                 105                 110

Val Tyr Gly Ala Cys Ala Phe Ala Phe Val Cys Phe Val Ile Arg
        115                 120                 125

Ala Ala Lys Asn Cys Met Ala Cys Arg Tyr Ala Arg Thr Arg Phe Thr
130                 135                 140

Asn Phe Ile Val Asp Asp Arg Gly Arg Val His Arg Trp Lys Ser Pro
145                 150                 155                 160
```

```
                    Ile Val Val Glu Lys Leu Gly Lys Ala Glu Val Asp Gly Asn Leu Val
                                    165                 170                 175

Thr Ile Lys His Val Val Leu Glu Gly Val Lys Ala Gln Pro Leu Thr
                                180                 185                 190

Arg Thr Ser Ala Glu Gln Glu Ala
                                195                 200

<210> SEQ ID NO 40
<211> LENGTH: 3293
<212> TYPE: DNA
<213> ORGANISM: Porcine reproductive and respiratory syndrome virus

<400> SEQUENCE: 40
gttttatttc cctccgggcc ctgtcattga accaacttta ggcctgaatt gaaatgaaat      60
ggggtccatg caaagccttt ttgacaaaat tggccaactt tttgtggatg ctttcacgga     120
gttcttggtg tccattgttg atatcattat attcttggcc attttgtttg gcttcaccat     180
cgccggttgg ctggtggtct tttgcatcag attggtttgc ccgcgatac tccgtacgcg      240 ccctgccatt cactctgagc aattacagaa gatcttatga ggcctttctt tcccagtgcc     300
aagtggacat tcccacctgg gaactaaac atcctttggg gatgttttgg caccataagg      360
tgtcaaccct gattgatgag atggtgtcgc gtcgaatgta ccgcatcatg gaaaaagcag     420
gacaggctgc ctggaaacag gtggtgagcg aggctacgct gtctcgcatt agtagtttgg     480
atgtggtggc tcattttcag catcttgccg ccatcgaagc cgagacctgt aaatatttgg     540
cctcccggct gcccatgcta cacaacctgc gcatgacagg gtcaaatgta accatagtgt     600
ataatagtac tttgaatcgg gtgtttgcta ttttcccaac ccctggttcc cggccaaagc     660
ttcatgactt tcagcaatgg ctaatagctg tgcattcctc catattttcc tctgttgcag     720
cttcttgtac tctctttgtt gtgctgtggt gcgggttcc aatactacgt actgtttttg      780
gtttccgctg gttaggggca ttttttcttt cgaactcata gtgaattaca cggtgtgccc     840
accttgcctc acccggcaag cagccgcaga ggcctacgaa cccggtaggt ctctttggtg     900
caggataggg tacgatcgat gtggagagga cgaccatgac gagctagggt ttatgatacc     960
gtctggcctc tccagcgaag gccacttgac cagtgtttac gcctggttgg cgttcttgtc    1020
cttcagctac acggcccagt tccacccga gatattcggg atagggaatg tgagtcgagt     1080
ttatgttgac atcaaacatc aactcatctg cgccgaacat gacgggcaga acaccacctt    1140
gcctcgtcat gacaacattt cggccgtgtt tcagacctat taccaacatc aagtcgacgg    1200
cggcaattgt tttcacctag aatggctgcg tcccttcttt tcctcatggt tggttttaaa    1260
tgtctcttgg tttctcaggc gttcgcctgc aaaccatgtt tcagttcgag tcttgcagac    1320
attaagacca acaccaccgc agcggcaagc tttgctgtcc tccaagacat cagttgcctt    1380
aggcatcgca actcggcctc tgaggcgatt cgcaaaatcc ctcagtgccg tacggcgata    1440
gggacaccta tgtatattac catcacagcc aatgtgacag atgaaaatta tttacattct    1500
tctgatctcc tcatgctctc ttcttgcctt ttctatgctt ctgagatgag tgaaagggga    1560
tttgaggtgg ttttttggca atgtgtcaggc atcgtggctg tgtgtgtcaa ttttaccagc    1620
tacgttcaac atgtcaggga gtttacccaa cgctccttga tggtcgacca tgtgcggctg    1680
ctccatttca tgacacctga gaccatgagg tgggcaaccg ttttagcctg tctttttgct    1740
attctgttgg caatttgaat gtttaagtat gttggggaaa tgcttgaccg tgggctgttg    1800
ctcgcgattg ctttctttgt ggtgtatcgt gccgttctgt tttactgtgc tcgccgacgc    1860
```

-continued

```
ccacagcaac agcagctctc atctgcaatt gatttacaac ttgacgctat gtgagctgaa    1920
tggcacagat tggctagctg atagatttga ttgggcagtg gagagctttg tcatctttcc    1980
tgttttgact cacattgtct cctatggcgc cctcaccacc agccatttcc ttgacacaat    2040
tgctttagtc actgtgtcta ccgccgggtt tgttcacggg cggtatgtcc taagtagcat    2100
ctacgcggtc tgtgccctgg ctgcgttgac ttgcttcgtc attaggtttg tgaagaattg    2160
catgtcctgg cgctactcat gtactagata taccaacttt cttctggata ctaagggcag    2220
actctatcgt tggcggtcgc ctgtcatcat agagaagagg ggcaaagttg aggtcgaagg    2280
tcatctgatc gatctcaaaa gagttgtgct tgatggttcc gtggcaaccc ctataaccag    2340
agtttcagcg gaacaatggg gtcgtcctta gatgacttct gttatgatag tacggctcca    2400
caaaaggtgc ttttggcatt ttctattacc tacacgccag taatgatata tgccctaaag    2460
gtgagtcgcg gccgactgct agggcttctg caccttttga ttttcctgaa ctgtgctttc    2520
accttcgggt acatgacatt catgcacttt cagagtacaa ataaggtcgc gctcactatg    2580
ggagcagtag ttgcactcct ttgggggggtg tactcagcca tagaaacctg gaaattcatc    2640
acctccagat gccgtttgtg cttgctaggc cgcaagtaca ttctggcccc tgcccaccac    2700
gttgaaagtg ccgcaggctt tcatccgatt gcggcaaatg ataaccacgc atttgtcgtc    2760
cggcgtcccg gctccactac ggtcaacggc acattggtgc ccgggttgaa aagcctcgtg    2820
ttgggtggca gaaaagctgt taaacaggga gtggtaaacc ttgtcaaata tgccaaataa    2880
caacggcaag cagcagaaga gaaagaaggg ggatggccag ccagtcaatc agctgtgcca    2940
gatgctgggt aagatcatcg cccagcaaaa ccagtctaga ggcaagggac cgggaaagaa    3000
aaataagaag aaaaacccgg agaagcccca ttttcctcta gcgactgaag atgatgtcag    3060
acatcacttt accccagtg agcggcaatt gtgtctgtcg tcaatccaaa ctgccttta a    3120
tcaaggcgct gggacttgca ccctgtcaga ttcagggagg ataagttaca ctgtggagtt    3180
tagtttgcct acgcatcata ctgtgcgctt gatccgcgtc acagcatcac cctcagcatg    3240
atgggctggc attcttgagg catcccagtg tttgaattgg aagaatgcgt ggt           3293
```

<210> SEQ ID NO 41
<211> LENGTH: 3293
<212> TYPE: DNA
<213> ORGANISM: Porcine reproductive and respiratory syndrome virus

<400> SEQUENCE: 41

```
gttttatttc cctccgggcc ccgtcattga accaacttta ggcctgaatt gaatgaaat     60
ggggtccgtg caaagccttt ttgacaaaat tggccaactt tttgtggatg ctttcacgga    120
gttcctggtg tccattgttg atatcatcat atttttggcc attttgtttg gcttcaccat    180
cgccggtttg ctggtggtct tttgcatcag attggtttgc tccgcgatac tccgtacgcg    240
ccctgccatt cactctgagc aattacagaa gatcttatga ggccttttta tcccagtgcc    300
aagtggacat tccaccctgg gaactaaaca tcctttggg gatgttttgg caccataagg    360
tgtcaaccct gattgatgaa atggtgtcgc gtcgcatgta ccgcatcatg gaaaaagcag    420
ggcaggctgc ctggaaacag gtggtgagcg aggctacgct gtcccgcatt agtagtttgg    480
atgtggtggc tcattttcag catcttgccg ccattgaagc cgagacttgt aaatatttgg    540
cctcccggct gcccatgcta cataacctgc gcataacagg gtcaaatgta accatagtgt    600
ataatagtac ttcggagcag gtgtttgcta ttttcccaac ccctggttcc cggccaaagc    660
```

-continued

| | |
|---|---|
| ttcatgattt tcagcaatgg ttaatagctg tacattcctc catattttcc tctgttgcag | 720 |
| cttcttgtac tcttttttgtt gtgctgtggc tgcgggttcc aatgctacgt actgtttttg | 780 |
| gtttccgctg gttaggggga attttccctt cgaactcatg gtgaattaca cggtgtgtcc | 840 |
| accttgcctc acccggcaag cagccgcaga ggtctacgaa cccggtaggt ctctttggtg | 900 |
| caggataggg tatgaccgat gtggggagga cgatcatgac gagctagggt ttatgatacc | 960 |
| gcctggcctc tccagcgaag gccacttgac tagtgtttac gcctggttgg cgttttttgtc | 1020 |
| cttcagctac acgcccagt tccatcccga gatattcggg atagggaatg tgagtcgagt | 1080 |
| ttatgttgac atcaaacatc aactcatttg cgccgaacat gacggacaga acgccacctt | 1140 |
| gcctcgtcat gacaatattt cagccgtgtt tcagacctat taccaacatc aagtcgatgg | 1200 |
| cggcaattgg tttcacctag aatggcttcg tcccttcttt tcctcatggt tggttttaaa | 1260 |
| tgtctcttgg tatctcaggc gttcgcctgc aaaccatgct tcagttcgag tcttgcagat | 1320 |
| attaagacca acactaccgc agcggcaagc tttgctgtcc tccaagacat cagttgcctt | 1380 |
| aggcatcgca actcggcctc tgaggcgatt cgcaaaatcc ctcagtgccg tacggcgata | 1440 |
| gggacacccg tgtatattac catcacagcc aatgtgacag atgagaatta tttacattct | 1500 |
| tctgatctcc tcatgctttc ttcttgcctt ttctacgctt ctgagatgag tgaaaaagga | 1560 |
| ttcaaggtgg tatttggcaa tgtgtcaggc atcgtggctg tgtgtgtcaa ttttaccagc | 1620 |
| tacgtccaac atgtcaggga gtttacccaa cgctccctgg tggtcgacca tgtgcggttg | 1680 |
| ctccatttca tgacacctga aaccatgagg tgggcaactg ttttagcctg tctttttgcc | 1740 |
| attctgctgg caatttgaat gtttaagtat gttggggaaa tgcttgaccg cgggctgttg | 1800 |
| ctcgcgattg ctttctttgt ggtgtatcgt gccgttctgt tttgctgtgc tcgccaacgc | 1860 |
| cagcgccaac agcagctccc atctacagct gatttacaac ttgacgctat gtgagctgaa | 1920 |
| tggcacagat tggctagctg ataaatttga ttgggcagtg gagagttttg tcatctttcc | 1980 |
| cgttttgact cacattgtct cctatggtgc cctcactact agccatctcc ttgacacagt | 2040 |
| cgccttagtc actgtgtcta ccgccgggtt tgttcacggg cggtatgtcc taagtagcat | 2100 |
| ctacgcggtc tgtgccctgg ctgcgttagc ttgcttcgtc attaggtttg caaagaattg | 2160 |
| catgtcctgg cgctattcgt gtaccagata taccaacttt cttctggaca ctaagggcag | 2220 |
| actctatcgt tggcattcgc ctgtcatcat agagaaaagg ggcaaagttg aggtcgaagg | 2280 |
| tcatctgatc gacctcaaaa gagttgtgct tgacggttcc gtggcaaccc ctataaccag | 2340 |
| agtttcagcg gaacaatggg gtcgtcctta gatgacttct gccatgatag tacggctcca | 2400 |
| caaaaggtgc ttttggcgtt ttctattacc tacacgccag tgatgatata tgccctaaag | 2460 |
| gtgagtcgcg gccgactgct agggcttctg cacctttga tcttcctgaa ttgtgctttc | 2520 |
| accttcgggt acatgacatt cgtgcacttt cagagtacaa ataaggtcgc gctcactatg | 2580 |
| ggagcagtag ttgcactcct ttgggggggtg tactcagcca tagaaacctg gaaattcatc | 2640 |
| acctccagat gccgtttgtg cttgctaggc cgcaagtaca ttctggcccc tgcccaccac | 2700 |
| gttgaaagtg ccgcaggctt tcatccgatt gcggcaaatg ataaccacgc atttgtcgtc | 2760 |
| cggcgtcccg gctccactac ggtcaacggc acattggtgc ccgggttgaa aagcctcgtg | 2820 |
| ttgggtggca gaaaagctgt taaacaggga gtggtaaacc ttgtcaaata tgccaaataa | 2880 |
| caacggcaag cagcagaaga gaaagaaggg ggatggccag ccagtcaatc agctgtgcca | 2940 |
| gatgctgggt aagatcatcg ctcagcaaaa ccagtccaga ggcaagggac cgggaaagaa | 3000 |
| aaacaagaag aaaaacccgg agaagcccca ttttcctcta gcgactgaag atgatgtcag | 3060 |

```
acatcacttc accccctagtg agcggcaatt gtgtctgtcg tcaatccaga ccgcctttaa    3120
tcaaggcgct gggacttgca ccctgtcaga ttcaggagg ataagttaca ctgtggagtt    3180
tagtttgcca acgcatcata ctgtgcgctt gatccgcgtc acagcatcac cctcagcatg    3240
atgggctggc attcttgagg catcccagtg tttgaattgg aagaatgcgt ggt           3293
```

```
<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence:Peptide

<400> SEQUENCE: 42

Pro Ser Ser Ser Trp
 1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence:Peptide

<400> SEQUENCE: 43

Arg Gln Arg Ile Ser
 1               5

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 44

Phe Gln Thr Ser
 1

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence:Peptide

<400> SEQUENCE: 45

Asn Gly Asn Ser Gly Ser Asn
 1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence:Peptide

<400> SEQUENCE: 46

Ser Asn Asp Ser Ser Ser His
 1               5

<210> SEQ ID NO 47
<211> LENGTH: 7
<212> TYPE: PRT
<213> ORGANISM: Artificial Sequence
```

```
<220> FEATURE:
<223> OTHER INFORMATION: Description of Artificial Sequence:Peptide

<400> SEQUENCE: 47

Ser Ser Ser Asn Ser Ser His
  1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence:Peptide

<400> SEQUENCE: 48

Ser Ala Asn Ser Ser Ser His
  1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence:Peptide

<400> SEQUENCE: 49

His Ser Asn Ser Ser Ser His
  1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence:Peptide

<400> SEQUENCE: 50

Ser Asn Ser Ser Ser Ser His
  1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence:Peptide

<400> SEQUENCE: 51

Asn Asn Ser Ser Ser Ser His
  1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence:Peptide

<400> SEQUENCE: 52

Asn Gly Gly Asp Ser Ser Thr
  1               5

<210> SEQ ID NO 53
<211> LENGTH: 7
<212> TYPE: PRT
<213> ORGANISM: Artificial Sequence
<220> FEATURE:
```

```
<223> OTHER INFORMATION: Description of Artificial Sequence:Peptide

<400> SEQUENCE: 53

Asn Gly Gly Asp Ser Ser Tyr
 1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence:Peptide

<400> SEQUENCE: 54

Ala Asn Lys Phe Asp Trp Ala Val Glu Thr
 1               5                  10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence:Peptide

<400> SEQUENCE: 55

Ala Asn Lys Phe Asp Trp Ala Val Glu Pro
 1               5                  10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence:Peptide

<400> SEQUENCE: 56

Ala Gly Glu Phe Asp Trp Ala Val Glu Thr
 1               5                  10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence:Peptide

<400> SEQUENCE: 57

Ala Asp Lys Phe Asp Trp Ala Val Glu Pro
 1               5                  10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence:Peptide

<400> SEQUENCE: 58

Ala Asp Arg Phe Asp Trp Ala Val Glu Pro
 1               5                  10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence:Peptide
```

<400> SEQUENCE: 59

Ser Ser His Phe Gly Trp Ala Val Glu Thr
 1               5                  10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence:Peptide

<400> SEQUENCE: 60

Leu Ile Cys Phe Val Ile Arg Leu Ala
 1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence:Peptide

<400> SEQUENCE: 61

Leu Thr Cys Phe Val Ile Arg Phe Ala
 1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence:Peptide

<400> SEQUENCE: 62

Leu Ile Cys Phe Val Ile Arg Phe Thr
 1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence:Peptide

<400> SEQUENCE: 63

Leu Ala Cys Phe Val Ile Arg Phe Ala
 1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence:Peptide

<400> SEQUENCE: 64

Leu Thr Cys Phe Val Ile Arg Phe Val
 1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence:Peptide

```
<400> SEQUENCE: 65

Leu Thr Cys Phe Ile Ile Arg Phe Ala
 1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence:Peptide

<400> SEQUENCE: 66

Phe Ile Cys Phe Val Ile Arg Phe Ala
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence:Peptide

<400> SEQUENCE: 67

Phe Val Cys Phe Val Ile Arg Ala Ala
 1               5

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence:Peptide

<400> SEQUENCE: 68

Leu Gln Leu Ile Tyr Asn Leu Thr Leu Cys Glu Leu Asn Gly Thr Asp
 1               5                  10                  15

Trp Leu

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 69
ctgcaagact cgaactgaa                                              19

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 70
ggggaattcg ggatagggaa tgtg                                        24

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence:
``` synthetic DNA

<400> SEQUENCE: 71 ggggatcct gttggtaata ggtctg         26

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 72 ggggatcct gttggtaata agtctg         26

<210> SEQ ID NO 73
<211> LENGTH: 28
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 73
ggtgaattcg ttttatttcc ctccgggc      28

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 74
gatagagtct gcccttag               18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 75
ggtttcacct agaatggc               18

<210> SEQ ID NO 76
<211> LENGTH: 17
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 76
gcttctgaga tgagtga                17

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

```
<400> SEQUENCE: 77
caaccaggcg taaacact                                              18

<210> SEQ ID NO 78
<211> LENGTH: 17
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 78
ctgagcaatt acagaag                                               17

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 79
gactgatggt ctggaaag                                              18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 80
ctgtatccga ttcaaacc                                              18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 81
aggttggctg gtggtctt                                              18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 82
tcgctcacta cctgtttc                                              18

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence:
      synthetic DNA
```

<400> SEQUENCE: 83
tgtgcccgcc ttgcctca                                                    18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 84
aaaccaattg cccccgtc                                                    18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 85
tatatcactg tcacagcc                                                    18

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 86
caaattgcca acagaatg                                                    18

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 87
caacttgacg ctatgtgagc                                                  20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 88
gccgcggaac catcaagcac                                                  20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 89
gactgctagg gcttctgcac                                           20

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 90
cgttgaccgt agtggagc                                             18

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 91
ccccatttcc ctctagcgac tg                                        22

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 92
cggccgtgtg gttctcgcca at                                        22

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 93
gactgcttta cggtctctc                                            19

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 94
gatgcctgac acattgcc                                             18

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 95
ctgcaagact cgaactgaa 19

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 96
gcacggatcc gaattaacat gaaatggggt 30

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 97
ccacctgcag attcaccgtg agttcgaaag 30

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 98
tgccaggatc cgtgtttaaa tatgttgggg 30

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 99
cgtggaattc atagaaaacg ccaagagcac 30

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 100
ggggatccag agtttcagcg g 21

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 101
gggaattctg gcacagctga ttgac 25

```
<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 102
ggggatcctt gttaaatatg cc                                               22

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 103
gggaattcac cacgcatt                                                    18

<210> SEQ ID NO 104
<211> LENGTH: 18
<212> TYPE: PRT
<213> ORGANISM: Porcine reproductive and respiratory syndrome virus

<400> SEQUENCE: 104

Leu Gln Leu Ile Tyr Asn Leu Thr Leu Cys Glu Leu Asn Gly Thr Asp
  1               5                  10                  15

Trp Leu

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 105
cgtcggatcc tcctacaatg gctaatagct                                       30

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 106
cgcgctgcag tgtccctatc gacgtgcggc                                       30

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 107
gtatggatcc gcaattggtt tcacctataa                                       30
```

```
<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 108
ataggaattc aacaagacgg cacgatacac                                        30
```

PROTEINS ENCODED BY POLYNUCLEIC ACIDS OF PORCINE REPRODUCTIVE AND RESPIRATORY SYNDROME VIRUS (PRRSV)

This is a continuation-in-part of application Ser. No. 08/478,316, filed Jun. 7, 1995, now U.S. Pat. No. 6,251,397, which is a continuation-in-part of application Ser. No. 08/301,435, filed on Sep. 1, 1994, now pending, which is a continuation-in-part of application Ser. No. 08/131,625, filed on Oct. 5, 1993, now U.S. Pat. No. 5,695,766, which is a continuation-in-part of application Ser. No. 07/969,071, filed on Oct. 30, 1992, now abandoned. The entire contents of application Ser. Nos. 08/301,435 and 08/131,625, filed on Sep. 1, 1994 and Oct. 5, 1993, respectively, are incorporated herein by reference in their entireties.

BACKGROUND OF THE INVENTION

1. Field of the Invention

The present invention concerns polynucleic acids isolated from a porcine reproductive and respiratory syndrome virus (PRRSV), a protein and/or a polypeptide encoded by the polynucleic acids, a vaccine which protects pigs from a PRRSV based on the protein or polynucleic acids, methods of making the proteins, polypeptides and polynucleic acids, a method of protecting a pig from PRRS using the vaccine, a method of producing the vaccine, a method of treating a pig infected by or exposed to a PRRSV, and a method of detecting a PRRSV.

2. Discussion of the Background

Porcine reproductive and respiratory syndrome (PRRS), a new and severe disease in swine, was first reported in the U.S.A. in 1987, and was rapidly recognized in many western European countries (reviewed by Goyal, J. Vet. Diagn. Invest., 1993, 5:656–664; and in U.S. application Ser. Nos. 08/131,625 and 08/301,435). The disease is characterized by reproductive failure in sows and gilts, pneumonia in young growing pigs, and an increase in preweaning mortality (Wensvoort et al., Vet. Q., 13:121–130, 1991; Christianson et al., 1992, Am. J. Vet. Res. 53:485–488; U.S. application Ser. Nos. 08/131,625 and 08/301,435).

The causative agent of PRRS, porcine reproductive and respiratory syndrome virus (PRRSV), was identified first in Europe and then in the U.S.A. (Collins et al., 1992, J. Vet. Diagn. Invest., 4:117–126). The European strain of PRRSV, designated as Lelystad virus (LV), has been cloned and sequenced (Meulenberg et al., 1993, Virology, 192:62–72 and J. Gen. Virol., 74:1697–1701; Conzelmann et al., 1993, Virology, 193:329–339).

PRRSV was provisionally classified in the proposed new virus family of Arteriviridae, which includes equine arteritis virus (EAV), lactate dehydrogenase-elevating virus (LDV) and simian hemorrhagic fever virus (SHFV) (Plagemann and Moennig, 1992, Adv. Virus. Res., 41:99–192; Godeny et al., 1993, Virology, 194:585–596; U.S. application Ser. Nos. 08/131,625 and 08/301,435). This group of single plus-strand RNA viruses shares many characteristics such as genome organization, replication strategy, morphology and macrophage tropism (Meulenberg et al., 1993; U.S. application Ser. Nos. 08/131,625 and 08/301,435). Subclinical infections and persistent viremia with concurrent antibody production are also characteristic histopathologic properties of the arteriviruses.

Antigenic, genetic and pathogenic variations have been reported among PRRSV isolates (Wensvoort et al., 1992, J. Vet. Diagn. Invest., 4:134–138; Mardassi et al., 1994, J. Gen. Virol., 75:681–685; U.S. application Ser. Nos. 08/131,625 and 08/301,435). Furthermore, U.S. and European PRRSV represent two distinct genotypes (U.S. application Ser. Nos. 08/131,625 and 08/301,435). Antigenic variability also exists among different North American isolates as well (Wensvoort et al., 1992). Marked differences in pathogenicity have been demonstrated not only between U.S. and European isolates, but also among different U.S. isolates (U.S. application Ser. Nos. 08/131,625 and 08/301,435).

The genomic organization of arteriviruses resembles coronaviruses and toroviruses in that their replication involves the formation of a 3'-coterminal nested set of subgenomic mRNAs (sg mRNAs) (Chen et al., 1993, J. Gen. Virol. 74:643–660; Den Boon et al., 1990, J. Virol., 65:2910–2920; De Vries et al., 1990, Nucleic Acids Res., 18:3241–3247; Kuo et al., 1991, J. Virol., 65:5118–5123; Kuo et al., 1992; U.S. application Ser. Nos. 08/131,625 and 08/301,435). Partial sequences of several North American isolates have also been determined (U.S. application Ser. Nos. 08/131,625 and 08/301,435; Mardassi et al., 1994, J. Gen. Virol., 75:681–685).

The genome of PRRSV is polyadenylated, about 15 kb in length and contains eight open reading frames (ORFS; Meulenberg et al., 1993; U.S. application Ser. Nos. 08/131,625 and 08/301,435). ORFs 1a and 1b probably encode viral RNA polymerase (Meulenberg et al., 1993). ORFs 5, 6 and 7 were found to encode a glycosylated membrane protein (E), an unglycosylated membrane protein (M) and a nucleocapsid protein (N), respectively (Meulenberg et al., 1995). ORFs 2 to 4 appear to have the characteristics of membrane-associated proteins (Meulenberg et al., 1993; U.S. application Ser. No. 08/301,435). However, the translation products of ORFs 2 to 4 were not detected in virus-infected cell lysates or virions (Meulenberg et al., 1995).

The major envelope glycoprotein of EAV encoded by ORF 5 may be the virus attachment protein, and neutralizing monoclonal antibodies (MAbs) are directed to this protein (de Vries, J. Virol. 1992; 66:6294–6303; Faaberg, J. Virol. 1995; 69:613–617). The primary envelope glycoprotein of LDV, a closely related member of PRRSV, is also encoded by ORF 5, and several different neutralizing MAbs were found to specifically immunoprecipitate the ORF 5 protein (Cafruny et al., Vir. Res., 1986; 5:357–375). Therefore, it is likely that the major envelope protein of PRRSV encoded by ORF 5 may induce neutralizing antibodies against PRRSV.

It has been proposed that antigenic variation of viruses is the result of direct selection of variants by the host immune responses (reviewed by Domingo et al., J. Gen. Virol. 1993, 74:2039–2045). Thus, these hypervariable regions are likely due to the host immune selection pressure and may explain the observed antigenic diversity among PRRSV isolates.

The M and N proteins of U.S. PRRSV isolates, including ISU 3927, are highly conserved (U.S. application Ser. No. 08/301,435). The M and N proteins are integral to preserving the structure of PRRSV virions, and the N protein may be under strict functional constraints. Therefore, it is unlikely either that (a) the M and N proteins are subjected to major antibody selection pressure or that (b) ORFs 6 and 7, which are likely to encode the M and N proteins, are responsible for or correlated to viral virulence. Interestingly, however, higher sequence variation of the LDV M protein was observed between LDV isolates with differing neurovirulence (Kuo et al., 1992, *Vir. Res.* 23:55–72).

ORFs 1a and 1b are predicted to translate into a single protein (viral polymerase) by frameshifting. ORFs 2 to 6 may encode the viral membrane associated proteins.

In addition to the genomic RNA, many animal viruses produce one or more sg mRNA species to allow expression of viral genes in a regulated fashion. In cells infected with PRRSV, seven species of virus-specific mRNAs representing a 3'-coterminal nested set are synthesized (mRNAs 1 to 7, in decreasing order of size). mRNA 1 represents the genomic mRNA. Each of the sg mRNAs contains a leader sequence derived from the 5'-end of the viral genome.

The numbers of the sg mRNAs differ among arteriviruses and even among different isolates of the same virus. A nested set of 6 sg mRNAs was detected in EAV-infected cells and European PRRSV-infected cells. However, a nested set of six (LDV-C) or seven (LDV-P) sg mRNAs, in addition to the genomic RNA, is present in LDV-infected cells. The additional sg MRNA 1-1 of LDV-P contains the 3'-end of ORF 1b and can potentially be translated to a protein which represents the C-terminal end of the viral polymerase. Sequence analysis of the sg mRNAs of LDV and EAV indicates that the leader-mRNA junction motif is conserved. Recently, the leader-mRNA junction sequences of the European LV were also shown to contain a common motif, UCAACC, or a highly similar sequence.

The sg mRNAs have been shown to be packaged into the virions in some coronaviruses, such as bovine coronavirus (BCV) and transmissible gastroenteritis virus (TGEV). However, only trace amounts of the sg mRNAs were detected in purified virions of mouse hepatitis virus (MHV), another coronavirus. The sg mRNAs of LDV, a closely related member of PRRSV, are also not packaged in the virions, and only the genomic RNA was detected in purified LDV virions.

The sg mRNAs of LDV and EAV have been characterized in detail. However, information regarding the sg mRNAs of PRRSV strains, especially the U.S. PRRSV, is very limited. Thus, a need is felt for a more thorough molecular characterization of the sg mRNAs of U.S. PRRSV.

The packaging signal of MHV is located in the 3'-end of ORF 1b, thus only the genomic RNA of MHV is packaged. The sg mRNAs of BCV and TGEV, however, are found in purified virions. The packaging signal of BCV and TGEV has not been determined. The Aura alphavirus sg MRNA is efficiently packaged into the virions, presumably because the packaging signal is present in the sg mRNA. The sindbis virus 26S sg mRNA is not packaged into virions because the packaging signal is located in the genome segment (not present in sg mRNA). The sg mRNAs of LDV, a closely related member of PRRSV, are also not packaged into the virions.

Many mechanisms are involved in the generation of the sg mRNAs. It has been proposed that coronaviruses utilize a unique leader RNA-primed transcription mechanism in which a leader RNA is transcribed from the 3' end of the genome-sized negative-stranded template RNA, dissociates from the template, and then rejoins the template RNA at downstream intergenic regions to prime the transcription of sg mRNAs. The model predicts that the 5'-leader contains a specific sequence at its 3'-end which is repeated further downstream in the genome, preceding each of the ORFs 2 to 7. The leader joins to the body of each of the sg mRNAs via the leader-mRNA junction segment.

PRRSV is an important cause of pneumonia in nursery and weaned pigs. PRRSV causes significant economic losses from pneumonia in nursery pigs (the exact extent of which are not fully known). Reproductive disease was the predominant clinical outcome of PRRSV infections during the past few years, due to the early prevalence of relatively low virulence strains of PRRSV. Respiratory disease has now become the main problem associated with PRRSV, due to the increasing prevalence of relatively high virulence strains of PRRSV. A need is felt for a vaccine to protect against disease caused by the various strains of PRRSV.

Surprisingly, the market for animal vaccines in the U.S. and worldwide is larger than the market for human vaccines. Thus, there exists an economic incentive to develop new veterinary vaccines, in addition to the substantial public health benefit which is derived from protecting farm animals from disease.

SUMMARY OF THE INVENTION

Accordingly, one object of the present invention is to provide a polynucleic acid isolated from a porcine reproductive and respiratory syndrome virus (PRRSV).

It is a further object of the present invention to provide an isolated polynucleic acid which encodes a PRRSV protein.

It is a further object of the present invention to provide a PRRSV protein, either isolated from a PRRSV or encoded by a PRRSV polynucleic acid.

It is a further object of the present invention to provide a protein- or polynucleic acid-based vaccine which protects a pig against PRRS.

It is a further object of the present invention to provide a method of raising an effective immunological response against a PRRSV using the vaccine.

It is a further object of the present invention to provide a method of producing a protein- or polynucleic acid-based vaccine which protects a pig against PRRS.

It is a further object of the present invention to provide a method of treating a pig exposed to a PRRSV or suffering from PRRS.

It is a further object of the present invention to provide a method of detecting PRRSV.

It is a further object of the present invention to provide an antibody which immunologically binds to a PRRSV protein or to an antigenic region of such a protein.

It is a further object of the present invention to provide an antibody which immunologically binds to a protein- or polynucleic acid-based vaccine which protects a pig against a PRRSV.

It is a further object of the present invention to provide a diagnostic kit for assaying or detecting a PRRSV.

It is a further object of the present invention to provide the above objects, where the PRRS virus is an Iowa strain of PRRSV.

These and other objects, which will become apparent during the following description of the preferred embodiments, have been provided by a purified and/or isolated polypeptide selected from the group consisting of proteins encoded by one or more open reading frames (ORF's) of an Iowa strain of porcine reproductive and respiratory syndrome virus (PRRSV), proteins at least 94% but less than 100% homologous with a protein encoded by an ORF 2 of an Iowa strain of PRRSV, proteins at least 88% but less than 100% homologous with a protein encoded by ORF 3 of an Iowa strain of PRRSV, proteins at least 93% homologous with an ORF 4 of an Iowa strain of PRRSV, proteins at least 90% homologous with an ORF 5 of an Iowa strain of PRRSV, proteins at least 97% but less than 100% homologous with proteins encoded by one or both of ORF 6 and ORF 7 of an Iowa strain of PRRSV, antigenic regions of such proteins which are at least 5 amino acids in length and which effectively stimulate protection in a porcine host against a subsequent challenge with a PRRSV isolate, and combinations thereof; an isolated polynucleic acid which encodes such a polypeptide or polypeptides; a vaccine comprising an effective amount of such a polynucleotide or polypeptide (s); antibodies which specifically bind to such a polynucleotide or polypeptide; methods of producing the same; and methods of (i) effectively protecting a pig against PRRS, (ii) treating a pig exposed to a PRRSV or suffering from PRRS, and (iii) detecting a PRRSV using the same.

BRIEF DESCRIPTION OF THE FIGURES

FIGS. 1A, 1B, 1C, 1D, 1E, 1F and 1G shows a nucleotide sequence comparison of ORFs 2 to 5 of U.S. isolates ISU 79 (SEQ ID NO: 7), ISU 1894 (SEQ ID NO: 6), ISU 3927 (SEQ ID NO: 2), ISU 22 and ISU 55 (SEQ ID NO: 4) (SEQ ID NO: 3) with other known PRRSV isolates (VR2385; SEQ ID NO: 1; VR2332; SEQ ID NO: 5);

FIGS. 2A, 2B, 2C and 2D respectively show the alignment of the deduced amino acid sequences of ORF 2, ORF 3, ORF 4 and ORF 5 of U.S. isolates ISU (SEQ ID NOS: 10, 18, 29 and 36 respectively), ISU 1894 (SEQ ID NOS: 12, 19, 27 and 35 respectively), ISU 22 (SEQ ID NO: 9, 20, 28 and 37, respectively), ISU 55 (SEQ ID NOS: 11, 17, 26 and 34, respectively) and ISU 3927 (SEQ ID NOS: 13, 21, 30 and 38 respectivley) with other known PRRSV isolates (VR 2385: SEQ ID NOS: 8, 15, 24 and 32 respectively; VR2332 SEQ ID NO: 14, 22, 25 and 33 respectively LV: SEQ ID NOS: 15, 23, and 39;

FIGS. 9A, 9B, 9C and 9D shows the sequence alignment of ORFs 2 to 7 of ISU 1894 (SEQ ID NO: 41), and ISU 79 (SEQ ID NO: 40), where the start codon of each ORF is indicated by +>, the termination codon of each ORF is indicated by asterisks (*), the determined or predicted leader-mRNA junction sequences are underlined and the locations of the leader-mRNA junction sequences relative to the start codon of each ORF are indicated by minus (–) numbers of nucleotides upstream of each ORF.

FIG. 13. Titers of monoclonal antibodies.

FIG. 15. Primers used to amplify PRRSV ORFs 2 through 7 genes with PCR.

FIG. 16. Recombinant proteins of PRRSV ORFs 2 to 5 expressed in insect cells. a=predicted $M_r$ of products of PRRSV ORFs 2 to 5 and N-glycosylation sites are based on nucleotide sequence studies (Meng et al, 1994 & Morozov et al, 1995). b=expressed products in insect cells. c=bands after tunicamycin treatment were determined by immunoblotting analysis. d=leader-free core proteins are determined on the basis of tunicamycin treatment analysis. The presence of the other bands in the recombinant products after tunicamycin treatment was possibly due to O-linked glycosylation, phosphorylation or other post-translational modifications.

DETAILED DESCRIPTION OF THE PREFERRED EMBODIMENTS

Figure 3:
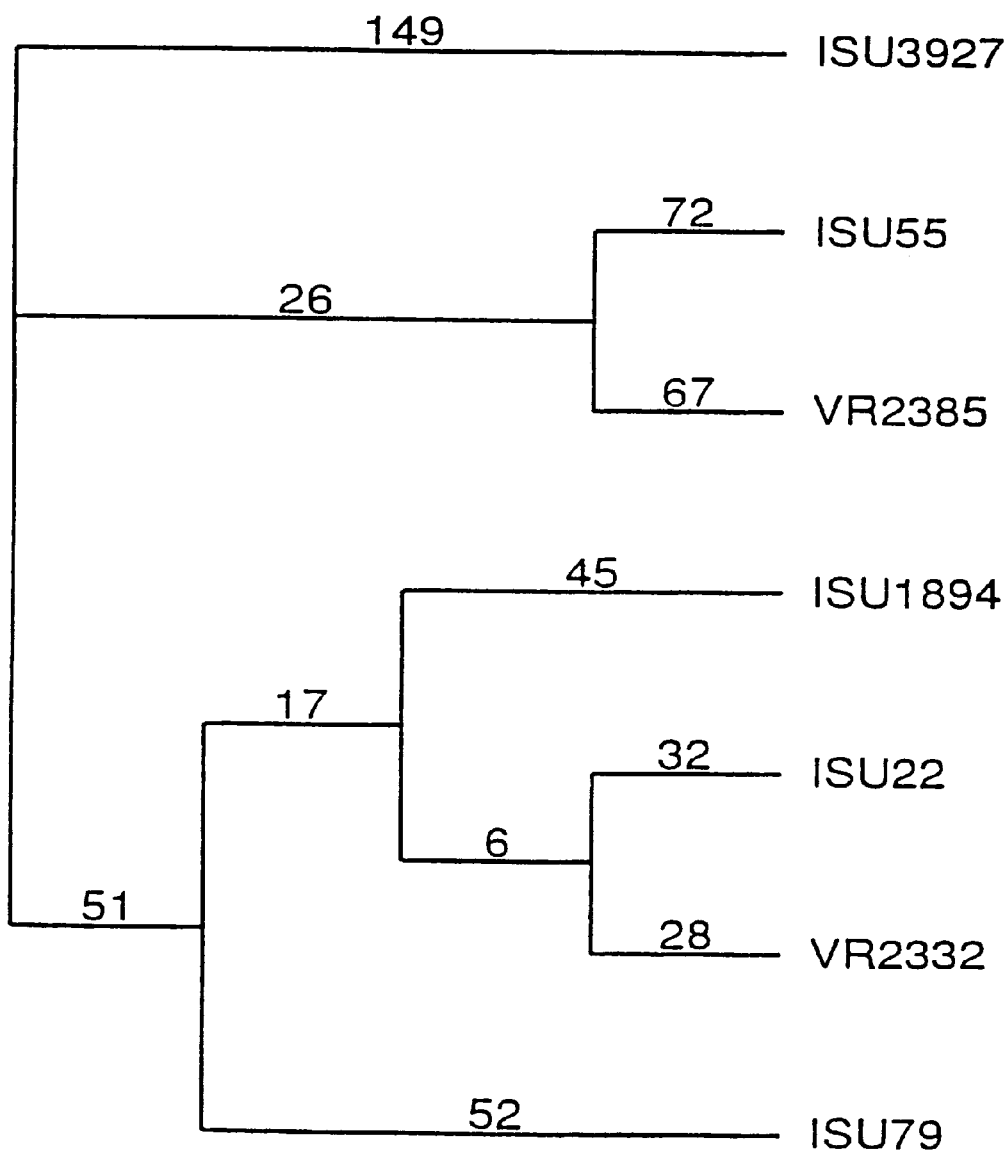
FIG. 3 shows a phylogenetic tree based on the nucleotide sequences of ORFs 2 to 7 of seven U.S. PRRSV isolates with differing virulence.

In the present application, the nucleotide sequences of the ORFs 2 to 5 of a low virulence isolate and four other Iowa strain PRRSV isolates with "moderate" and high virulence have been determined. Based on comparisons of ORFs 2 to 7 of various PRRSV isolates, the least virulent U.S. isolate known (ISU 3927) has relatively high sequence variations in ORFs 2 to 4, as compared to the variations in other U.S. isolates. Furthermore, based on analysis of the sequences of the ORFs, at least three minor genotypes exist within the major genotype of U.S. PRRSV.

Sequence analysis of the ORF 5 protein of different PRRSV isolates reveal three hypervariable regions which contained non-conserved amino acid substitutions. These regions are hydrophilic and also antigenic as predicted by computer analysis.

In the present invention, a "porcine reproductive and respiratory syndrome virus" or "PRRSV" refers to a virus which causes the diseases PRRS, PEARS, SIRS, MSD and/or PIP (the term "PIP" now appears to be disfavored), including the Iowa strain of PRRSV, other strains of PRRSV found in the United States (e.g., VR 2332), strains of PRRSV found in Canada (e.g., IAF-exp91), strains of PRRSV found in Europe (e.g., Lelystad virus, PRRSV-10), and closely-related variants of these viruses which may have appeared and which will appear in the future.

The "Iowa strain" of PRRSV includes (a) PRRSV isolates deposited in the American Type Culture Collection 10801 University Boulevard, Marasses, Va. 20110-2205 by the present inventors and/or described in this application and/or in either of prior U.S. application Ser. Nos. 08/131,625 and 08/301,435, (b) PRRS viruses which produce more than six sg mRNAs when cultured or passaged in CRL 11171 cells, (c) PRRSVs which produce at least 40% gross lung lesions or lung consolidation in 5-week-old caesarean-derived, colostrum-deprived piglets 10 days post-infection, (d) a PRRSV isolate having a genome which encodes a protein having the minimum homology to a PRRSV ORF described in Table 2 below, and/or (d) any PRRSV isolate having the identifying characteristics of such a virus.

The present vaccine is effective if it protects a pig against infection by a porcine reproductive and respiratory syndrome virus (PRRSV). A vaccine protects a pig against infection by a PRRSV if, after administration of the vaccine to one or more unaffected pigs, a subsequent challenge with a biologically pure virus isolate (e.g., VR 2385, VR 2386, or other virus isolate described below) results in a lessened severity of any gross or histopathological changes (e.g., lesions in the lung) and/or of symptoms of the disease, as compared to those changes or symptoms typically caused by the isolate in similar pigs which are unprotected (i.e., relative to an appropriate control). More particularly, the present vaccine may be shown to be effective by administering the vaccine to one or more suitable pigs in need thereof, then after an appropriate length of time (e.g., 1–4 weeks), challenging with a large sample ($10^{3-7}$ $TCID_{50}$) of a biologically pure PRRSV isolate. A blood sample is then drawn from the challenged pig after about one week, and an attempt to isolate the virus from the blood sample is then performed (e.g., see the virus isolation procedure exemplified in Experiment VIII below). Isolation of the virus is an indication that the vaccine may not be effective, and failure to isolate the virus is an indication that the vaccine may be effective.

Thus, the effectiveness of the present vaccine may be evaluated quantitatively (i.e., a decrease in the percentage of consolidated lung tissue as compared to an appropriate control group) or qualitatively (e.g., isolation of PRRSV from blood, detection of PRRSV antigen in a lung, tonsil or lymph node tissue sample by an immunoperoxidase assay method [described below], etc.). The symptoms of the porcine reproductive and respiratory disease may be evaluated quantitatively (e.g., temperature/fever), semi-quantitatively (e.g., severity of respiratory distress [explained in detail below], or qualitatively (e.g., the presence or absence of one or more symptoms or a reduction in severity of one or more symptoms, such as cyanosis, pneumonia, heart and/or brain lesions, etc.).

An unaffected pig is a pig which has either not been exposed to a porcine reproductive and respiratory disease infectious agent, or which has been exposed to a porcine reproductive and respiratory disease infectious agent but is not showing symptoms of the disease. An affected pig is one which shows symptoms of PRRS or from which PRRSV can be isolated.

The clinical signs or symptoms of PRRS may include lethargy, respiratory distress, "thumping" (forced expiration), fevers, roughened haircoats, sneezing, coughing, eye edema and occasionally conjunctivitis. Lesions may include gross and/or microscopic lung lesions, myocarditis, lymphadenitis, encephalitis and rhinitis. In addition, less virulent and non-virulent forms of PRRSV and of the Iowa strain have been found, which may cause either a subset of the above symptoms or no symptoms at all. Less virulent and non-virulent forms of PRRSV can be used according to the present invention to provide protection against porcine reproductive and respiratory diseases nonetheless.

The phrase "polynucleic acid" refers to RNA or DNA, as well as mRNA and cDNA corresponding to or complementary to the RNA or DNA isolated from the virus or infectious agent. An "ORF" refers to an open reading frame, or polypeptide-encoding segment, isolated from a viral genome, including a PRRSV genome. In the present polynucleic acid, an ORF can be included in part (as a fragment) or in whole, and can overlap with the 5'- or 3'-sequence of an adjacent ORF (see for example, FIG. 1 and Experiment 1 below). A "polynucleotide" is equivalent to a polynucleic acid, but may define a distinct molecule or group of molecules (e.g., as a subset of a group of polynucleic acids).

In the Experiments described hereinbelow, the isolation, cloning and sequencing of ORFs 2 to 5 of (a) a low virulence U.S. PRRSV isolate and (b) two other U.S. PRRSV isolates of varying virulence were determined. The nucleotide and deduced amino acid sequences of these three U.S. isolates were compared with the corresponding sequences of other known PRRSV isolates (see, for example, U.S. application Ser. No. 08/301,435). The results indicate that considerable genetic variations exist not only between U.S. PRRSV and European PRRSV, but also among the U.S. isolates as well.

The amino acid sequence identity between the seven U.S. PRRSV isolates studied was 91–99% in ORF 2, 86–98% in ORF 3, 92–99% in ORF 4 and 88–97% in ORF 5. The least virulent U.S. isolate known (ISU 3927) has higher sequence variations in ORFs 2 to 4 than in ORFs 5 to 7, as compared to other U.S. isolates. Three hypervariable regions with antigenic potential have been identified in the major envelope glycoprotein encoded by ORF 5.

Pairwise comparison of the sequences of ORFs 2 to 7 and phylogenetic tree analysis implied the existence of at least three groups of PRRSV variants (or minor genotypes) within the major genotype of U.S. PRRSV. The least virulent U.S. isolate known forms a distinct branch from other U.S. isolates with differing virulence. The results of this study have implications for the taxonomy of PRRSV and vaccine development.

In a further experiment, the sg mRNAs in PRRSV-infected cells were characterized. The data showed that a 3'-coterminal nested set of six or seven sg mRNAs is formed in cells infected with different isolates of PRRSV. However, unlike some of the coronaviruses and alphavirus, the sg mRNAs of PRRSV are not packaged into the virion, and only was the genomic RNA of PRRSV detected in purified virions. Variations in the numbers of the sg mRNAs among different PRRSV isolates with differing virulence were also observed. Further sequence analysis of ORFs 2 to 7 of two U.S. isolates and their comparison with the European LV reveal the heterogeneic nature of the leader-mRNA junction sequences of PRRSV.

As demonstrated in Experiment 2 below, a 3'-coterminal nested set of six or more sg mRNAs is formed in cells infected with different isolates of PRRSV. The presence of a nested set of sg mRNAs further indicates that U.S. PRRSV, like the European isolate Lelystad virus (LV), belongs to the newly proposed Arteriviridae family including LDV, EAV and SHFV. Northern blot analysis with ORF-specific probes indicates that the structure of the PRRSV sg mRNAs is polycistronic, and each of the sg mRNAs except for sg mRNA 7 contains multiple ORFs. Therefore, the sequence of each sg mRNA is contained within the 3'-portion of the next larger sg mRNA, and not all 5'-ends of the sg mRNAs overlap with the sequences of the smaller sg mRNAs.

There is no apparent correlation, however, between the numbers of sg mRNAs and viral pneumovirulence. An additional species, sg MRNA 4-1, was found to contain a small ORF (ORF 4-1) with a coding capacity of 45 amino acids at its 5'-end.

In Experiment 2 below, the sg mRNAs of PRRSV are shown not to be packaged into the virions. Whether sg mRNAs are packaged into virions may depend an whether the sg mRNAs contain a packaging signal. Since the sg mRNAs of PRRSV are not packaged into virions, the encapsidation signal of PRRSV is likely localized in the ORF 1 region which is unique to the viral genome, but which is not present in the sg mRNAs.

In Experiment 2 below, the junction segments (the leader-mRNA junction sequences) of sg mRNAs 3 and 4 of two U.S. isolates of PRRSV, ISU 79 and ISU 1894, are determined. The knowledge of the leader-mRNA junction sequence identities provides means for effectively producing (a) chimeric viruses to be used as an infectious clone and/or as a vaccine, and (b) vectors for inserting or "shuttling" one or more genes into a suitable, infectable host. Methods for designing and producing such chimeric viruses, infectious clones and vectors are known (see, for example, Sambrook et al, "Molecular Cloning: A Laboratory Manual", 2nd ed., Cold Spring Harbor Laboratory, Cold Spring Harbor, N.Y.).

The leader-mRNA junction sequence of sg mRNAs 3 and 4 of the two isolates are different (TTGACC for mRNA 4-1 of ISU 79, GTAACC for mRNA 3, and TTCACC for mRNA 4). Most of the nucleotide differences in the junctions are present in the first 3 nucleotides. The last 3 nucleotides are invariable, suggesting that the joining of the leader sequence to the bodies of sg mRNAs occurs within the 5'-end of the leader-mRNA junction sequence. Similar observations have been reported for LV, EAV and LDV.

The acquisition of the additional sg MRNA 4-1 in isolate ISU 79 is due to a single nucleotide substitution which generates a new leader mRNA junction sequence. This substitution occurs in the last nucleotide of the junction segment, suggesting that the last nucleotide of the leader-mRNA junction motif is critical for the binding of the leader and for the initiation of transcription.

Although the sequence homology between the leader and the intergenic regions of coronaviruses led to the hypothesis that basepairing might be essential in the leader-primed transcription, no experimental evidence has documented for the a requirement of base-pairing in transcription of the sg mRNAs. For example, the sequence at the 3'-end of the leader of both coronaviruses and arteriviruses that is involved in the fusion process remains unknown.

Several lines of evidence support the leader-primed transcription mechanism for coronaviruses, but the presence of negative-stranded sg mRNAs and sg replicative intermediates (sg RI) in coronavirus-infected cells suggests that the mechanism involved in sg mRNA synthesis is more complex than mere base-pairing of the leader sequence with a junction sequence. However, negative-stranded sg mRNAs have not been detected in arteriviruses except for LDV, and sg RIs have been detected only in EAV-infected cells. Therefore, sg mRNA synthesis in arteriviruses, and particularly in PRRSV, may be less complicated than in coronaviruses.

Sequence analysis of the ORFs 2 to 7 of two U.S. PRRSV isolates and comparison of the sequences with LV reveals the heterogeneity of the leader-mRNA junction sequences. The presence of the leader-mRNA junction motifs at positions which do not correspond to a sg mRNA raises a question as to whether the short stretch of only six nucleotides which are conserved in the leader and junction sequences in the genomes of PRRSV and other arteriviruses is sufficient for efficient binding of the leader to these specific junction sites upstream of the ORFs. This apparent discrepancy, however, may be explained by the following two possibilities.

First, additional structural elements, such as secondary structures or the sequences surrounding the leader-mRNA junction segment, are expected to be involved in the fusion (binding) of the leader to the specific sites. It has been shown that, in MHV, the sequence flanking the consensus sequence (leader-mRNA junction sequence) of UCUAAAC affects the efficiency of sg DI RNA transcription, and that the consensus sequence was necessary but not sufficient in and of itself for the synthesis of the DI mRNA.

Second, the distance between two leader-mRNA junction regions may affect the transcription of sg mRNAs. It has been demonstrated that the downstream leader-mRNA junction region was suppressing sg DI RNA synthesis of MHV from the upstream leader-mRNA junction region. The suppression was significant when the two leader-mRNA junction sequence separation was less than 35 nucleotides. However, significant inhibition of larger sg DI RNA synthesis (from the upstream leader-mRNA junction sequence) was not observed when the two leader-mRNA junction regions were separated by more than 100 nucleotides.

The previously reported experimental results are consistent with the observations reported in Experiment 2 below, where an additional species of sg mRNA 4-1, in addition to the sg mRNA 4, is observed in some of the PRRSV isolates. The leader-mRNA junction sequences of sg mRNAs 4 and 4-1 in the Iowa strain of PRRSV are separated by about 226 nucleotides. Therefore, the synthesis of the larger sg mRNA 4-1 from the upstream leader-mRNA junction sequence is not suppressed by the presence of the downstream leader-mRNA 4 junction sequence.

In contrast, multiple potential leader-mRNA junction sequences were found at different positions upstream of ORFs 3, 5, 6 and 7, but there were no sg mRNAs corresponding to these leader-mRNA junction motifs in the Northern blot analysis. Most of these leader-mRNA junction sequences are separated by less than 50 nucleotides from the downstream leader-mRNA junction region, except for ORF 7 (in which the two potential leader-mRNA junction sequences are separated by 114 nucleotides). However, sg mRNA 7 in Northern blot analysis showed a widely-diffused band. Therefore, transcription of the larger sg mRNA 7 from the upstream leader-mRNA junction sequence may not be significantly suppressed by the downstream junction sequence, but it is not easily distinguishable from the abundant sg mRNA 7 by Northern blot analysis.

THE PRESENT POLYNUCLEOTIDES AND POLYPEPTIDES

ORF's 2–7 of plaque-purified PRRSV isolate ISU-12 (deposited on Oct. 30, 1992, in the American Type Culture Collection, 10801 University Boulevard Marasses, Va.

20110-2205, U.S.A., under the accession numbers VR 2385 [3×plaque-purified] and VR 2386 [non-plaque-purified]) and ORF's 6–7 of PRRSV isolates ISU-22, ISU-55, ISU-3927 (deposited on Sep. 29, 1993, in the American Type Culture Collection under the accession numbers VR 2429, VR 2430 and VR 2431, respectively), ISU-79 and ISU-1894 (deposited on Aug. 31, 1994, in the American Type Culture Collection under the accession numbers VR 2474 and VR 2475, respectively) are described in detail in U.S. application Ser. No. 08/301,435. However, the techniques used to isolate, clone and sequence these genes can be also applied to the isolation, cloning and sequencing of the genomic polynucleic acids of any PRRSV. Thus, the present invention is not limited to the specific sequences disclosed in the Experiments below.

For example, primers for making relatively large amounts of DNA by the polymerase chain reaction (and if desired, for making RNA by transcription and/or protein by translation in accordance with known in vivo or in vitro methods) can be designed on the basis of sequence information where more than one sequence obtained from a PRRSV genome has been determined (e.g., ORF's 2–7 of VR 2385, VR 2429, VR 2430, VR 2431, VR 2474, ISU-1894, VR 2332 and Lelystad virus). A region from about 15 to 50 nucleotides in length having at least 80% and preferably at least 90% identity is selected from the determined sequences. A region where a deletion occurs in one of the sequences (e.g., of at least 5 nucleotides) can be used as the basis for preparing a selective primer for selective amplification of the polynucleic acid of one strain or type of PRRSV over another (e.g., for the differential diagnosis of North American and European PRRSV strains).

Once the genomic polynucleic acid is amplified and cloned into a suitable host by known methods, the clones can be screened with a probe designed on the basis of the sequence information disclosed herein. For example, a region of from about 50 to about 500 nucleotides in length is selected on the basis of either a high degree of identity (e.g., at least 90%) among two or more sequences (e.g., in ORF's 6–7 of the Iowa strains of PRRSV disclosed in Experiment III below), and a polynucleotide of suitable length and sequence identity can be prepared by known methods (such as automated synthesis, or restriction of a suitable fragment from a polynucleic acid containing the selected region, PCR amplification using primers which hybridize specifically to the polynucleotide, and isolation by electrophoresis). The polynucleotide may be labeled with, for example, $^{32}P$ (for radiometric identification) or biotin (for detection by fluorometry). The probe is then hybridized with the polynucleic acids of the clones and detected according to known methods.

The present Inventors have discovered that one or more of ORFs 2–4 may be related to the virulence of PRRSV. For example, at least one isolate of PRRSV which shows relatively low virulence also appears to have a deletion in ORF 4 (see, for example, Experiments VIII–XI in U.S. application Ser. No. 08/301,435). Furthermore, the least virulent known isolate (VR 2431) shows a relatively high degree of variance in both nucleotide and amino acid sequence information in ORFs 2–4, as compared to other U.S. PRRSV isolates. Thus, in one embodiment, the present invention concerns polynucleotides and polypeptides related to ORFs 2–4 of VR 2431.

In a further embodiment, the present invention is concerned with a polynucleic acid obtained from a PRRSV isolate which confers immunogenic protection directly or indirectly against a subsequent challenge with a PRRSV, but in which the polynucleic acid is deleted or mutated to an extent which would render a PRRSV containing the polynucleic acid either low-virulent (i.e., a "low virulence" (lv) phenotype; see the corresponding explanation in U.S. application Ser. No. 08/301,435) or non-virulent (a so-called "deletion mutant"). Preferably, one or more of ORFs 2–4 is/are deleted or mutated to an extent which would render a PRRS virus non-virulent. However, it may be desirable to retain regions of one or more of ORFs 2–4 in the present polynucleic acid which (i) encode an antigenic and/or immunoprotective peptide fragment and which (ii) do not confer virulence to a PRRS virus containing the polynucleic acid.

The present invention also encompasses a PRRSV per se in which one or more of ORFs 2–4 is deleted or mutated to an extent which renders it either low-virulent or non-virulent (e.g., VR 2431). Such a virus is useful as a vaccine or as a vector for transforming a suitable host (e.g., MA-104, PSP 36, CRL 11171, MARC-145 or porcine alveolar macrophage cells) with a heterologous gene. Preferred heterologous genes which may be expressed using the present deletion mutant may include those encoding a protein or an antigen other than a porcine reproductive and respiratory syndrome virus antigen (e.g., pseudorabies and/or swine influenza virus proteins and/or polypeptide-containing antigens, a porcine growth hormone, etc.) or a polypeptide-based adjuvant (such as those discussed in U.S. application Ser. No. 08/301,435 for a vaccine composition).

It may also be desirable in certain embodiments of the present polynucleic acid which contain, for example, the 3'-terminal region of a PRRSV ORF (e.g., from 200 to 700 nucleotides in length), at least part of which may overlap with the 5'-region of the ORF immediately downstream. Similarly, where the 3'-terminal region of an ORF may overlap with the 5'-terminal region of the immediate downstream ORF, it may be desirable to retain the 5'-region of the ORF which overlaps with the ORF immediately downstream.

The present inventors have also discovered that ORF 5 in the PRRSV genome appears to be related to replication of the virus in mammalian host cells capable of sustaining a culture while infected with PRRSV. Accordingly, the present invention is also concerned with polynucleic acids obtained from a PRRSV genome in which ORF 5 may be present in multiple copies (a so-called "overproduction mutant"). For example, the present polynucleic acid may contain at least two, and more preferably, from 2 to 10 copies of ORF 5 from a high-replication (hr) phenotype PRRSV isolate.

Interestingly, the PRRSV isolate ISU-12 has a surprisingly large number of potential start codons (ATG/AUG sequences) near the 5'-terminus of ORF 5, possibly indicating alternate start sites of this gene. Thus, alternate forms of the protein encoded by ORF 5 of a PRRSV isolate may exist, particularly where alternate ORF's encode a protein having a molecular weight similar to that determined experimentally (e.g., from about 150 to about 250 amino acids in length). The most likely coding region for ORF 5 of ISU-12 is indicated in FIG. 1.

One can prepare deletion and overproduction mutants in accordance with known methods. For example, one can prepare a mutant polynucleic acid which contains a "silent" or degenerate change in the sequence of a region encoding a polypeptide. By selecting and making an appropriate degenerate mutation, one can substitute a polynucleic acid sequence recognized by a known restriction enzyme (see, for example, Experiment 2 below). Thus, if a silent, degenerate mutation is made at one or two of the 3'-end of an ORF and the 5'-end of a downstream ORF, one can insert a synthetic polynucleic acid (a so-called "cassette") which may contain a polynucleic acid encoding one or multiple copies of an hr ORF 5 protein product, of a PRRSV or other viral envelope protein and/or an antigenic fragment of a PRRSV protein. The "cassette" may be preceded by a suitable initiation codon (ATG), and may be suitably terminated with a termination codon at the 3'-end (TAA, TAG or TGA). Of course, an oligonucleotide sequence which does not encode a polypeptide may be inserted, or alternatively, no cassette may be inserted. By doing so, one may provide a so-called deletion mutant.

The present invention also concerns regions and positions of the polypeptides encoded by ORFs of VR 2431 which may be responsible for the low virulence of this isolate. Accordingly, the present isolated and/or purified polypeptide may be one or more encoded by a "low-virulence mutation" of one or more of ORFs 2, 3 and 4 of a PRRSV (or a low-virulence fragment thereof at least 5 amino acids in length) in which one or more of positions 12–14 of the polypeptide encoded by ORF 2 are RGV (in which "R", "G" and "V" are the one-letter abbreviations for the corresponding amino acids), positions 44–46 are LPA, position 88 is A, position 92 is R, position 141 is G, position 183 is H, position 218 is S, position 240 is S and positions 252–256 are PSSSW (SEQ ID NO:42), or any combination thereof. Other amino acid residue identities which can be further combined with one or more of the above amino acid position identities include those at position 174 (I) and position 235 (M).

The present isolated and/or purified polypeptide may also be one encoded by an ORF 3 of a PRRSV in which one or more of the specified amino acid identities may be selected from those at positions 11 (L), 23 (V), 26–28 (TDA), 65–66 (QI), 70 (N), 79 (N), 93 (T), 100–102 (KEV), 134 (K), 140 (N), 223–227 (RQRIS:SEQ ID NO:43), 234 (A) and 235 (M), or any combination thereof, which may be further combined with one or more of positions 32 (F), 38 (M), 96 (P), 143 (L), 213–217 (FQTS;SEQ ID NO:44), 231 (R), and 252 (A).

The present isolated and/or purified polypeptide may also be one encoded by an ORF 4 of a PRRSV in which one or more of the specified amino acid identities may be selected from those at positions 13 (E), 43 (N), 56 (G), 58–59 (TT), 134 (T), 139 (I) and any combination thereof, which may be further combined with one or more of positions 2–3 (AA), 51 (G) and 63 (P).

The present invention also concerns polynucleotide sequences encoding polypeptide sequences of 5 or more amino acids, preferably 10 or more amino acids, and up to the full length of the polypeptide, encoded by any one of ORFs 2–4 of VR 2431, in which the polynucleotides at the codon(s) corresponding to the amino acid positions detailed in the preceding three paragraphs are replaced with polynucleotides encoding the corresponding amino acids of the proteins encoded by the corresponding ORF of VR 2431.

In a further embodiment of the present invention, the polynucleic acid encodes one or more proteins, or antigenic regions thereof, of a PRRSV. Preferably, the present nucleic acid encodes at least one antigenic region of a PRRSV membrane (envelope) protein. More preferably, the present polynucleic acid encodes a hypervariable region from a ORF 5 PRRSV protein product (see the discussion below) or (b) contains at least one copy of the ORF-5 gene from a high virulence (hv) phenotype isolate of PRRSV (see the description of "hv phenotype" in U.S. application Ser. No. 08/301, 435) and a sufficiently long fragment, region or sequence of at least one of ORF-2, ORF-3, ORF-4, ORF-5 and/or ORF-6 from the genome of a PRRSV isolate to encode an antigenic region of the corresponding protein(s) and effectively stimulate protection against a subsequent challenge with, for example, a hv phenotype PRRSV isolate.

Even more preferably, at least one entire envelope protein encoded by ORF-2, ORF-3, ORF-5 and/or ORF-6 of a PRRSV is contained in the present polynucleic acid, and the present polynucleic acid excludes or modifies a sufficiently long portion of one of ORFs 2–4 from a PRRSV to render a PRRSV containing the same either low-virulent or non-virulent. Most preferably, the polynucleic acid is isolated from the genome of an isolate of the Iowa strain of PRRSV (for example, VR 2385 (3×plaque-purified ISU-12), VR 2386 (non-plaque-purified ISU-12), VR 2428 (ISU-51), VR 2429 (ISU-22), VR 2430 (ISU-55), VR 2431 (ISU-3927), VR 2474 (ISU-79) and/or ISU-1894).

A further preferred embodiment of the present invention includes a polynucleotide encoding an amino acid sequence from a hypervariable region of ORF 5 of a PRRSV, preferably of an Iowa strain of PRRSV. Thus, such polynucleotides encode one (or more) of the following amino acid sequences:

TABLE 1

| Hypervariable Region 1 (positions 32–38) | | Hypervariable Region 2 (Positions 57–66) | | Hypervariable Region 3 (Pos'ns 120–128) | |
|---|---|---|---|---|---|
| NGNSGSN | (SEQ ID NO:45) | ANKFDWAVET | (SEQ ID NO:46) | LICFVIRLA | (SEQ ID NO:47) |
| SNDSSSH | (SEQ ID NO:48) | ANKFDWAVEP | (SEQ ID NO:49) | LTCFVIRFA | (SEQ ID NO:50) |
| SSSNSSH | (SEQ ID NO:51) | AGEFDWAVET | (SEQ ID NO:52) | LICFVIRFT | (SEQ ID NO:53) |
| SANSSSH | (SEQ ID NO:54) | ADKFDWAVEP | (SEQ ID NO:55) | LACFVIRFA | (SEQ ID NO:56) |
| HSNSSSH | (SEQ ID NO:57) | ADRFDWAVEP | (SEQ ID NO:58) | LTCFVIRFV | (SEQ ID NO:59) |
| SNSSSSH | (SEQ ID NO:60) | SSHFGWAVET | (SEQ ID NO:61) | LTCFIIRFA | (SEQ ID NO:62) |
| NNSSSSH | (SEQ ID NO:63) | | | FICFVIRFA | (SEQ ID NO:64) |
| NGGDSST(Y) | (SEQ ID:65–66) | | | FVCFVIRAA | (SEQ ID NO:67) |

In this embodiment, the polynucleotide may encode further amino acid sequences of a PRRSV ORF 5 (as disclosed in FIG. 3 or in U.S. application Ser. Nos. 08/131,625 or 08/301,435), as long as one or more of the hypervariable regions at positions 32–38, 57–66 and/or 120–128 are included. (The present invention specifically excludes the proteins and polynucleotides of ORF 5 of LV and VR 2332.)

A further preferred embodiment of the present invention concerns a purified preparation which may comprise, consist essentially of or consist of a polynucleic acid having a sequence of the formula (I) or (II):

$$5'\text{-}\alpha\text{-}\beta\text{-}3' \qquad (I)$$

$$5'\text{-}\alpha\text{-}\beta\text{-}\gamma 3' \qquad (II)$$

wherein α encodes at least one polypeptide, or antigenic or low-virulence fragment thereof encoded by a polynucleotide selected from the group consisting of ORFs 2, 3 and 4 of an Iowa strain of PRRSV and regions thereof encoding such antigenic and/or low-virulence fragments; and β is at least one copy of an ORF 5 from an Iowa strain of PRRSV or an antigenic fragment thereof (e.g. one or more hypervariable regions), preferably a full-length copy from a high replication (hr) phenotype; and γ encodes at least one polypeptide or antigenic fragment thereof encoded by a polynucleotide selected from the group consisting of ORF 6 and ORF 7 of an Iowa strain of PRRSV and regions thereof encoding the antigenic fragments.

Alternatively, the present invention may concern a purified preparation which may comprise, consist essentially of or consist of a polynucleic acid having a sequence of the formula (III):

$$5'\text{-}\beta\text{-}\delta\text{-}\gamma\text{-}3' \qquad (III)$$

where β and γ are as defined above; and δ is either a covalent bond or a linking polynucleic acid which does not materially affect transcription and/or translation of the polynucleic acid. Preferably, β is a polynucleotide encoding at least one hypervariable region of a protein encoded by an ORF 5 of an Iowa strain of PRRSV, and more preferably, encodes a full-length protein encoded by an ORF 5 of an Iowa strain of PRRSV.

The present invention may also concern a purified preparation which may comprise, consist essentially of or consist of a polynucleic acid having a sequence of the formula (IV):

$$5'\text{-}\alpha\text{-}\beta\text{-}\delta\text{-}\gamma\text{-}3' \qquad (IV)$$

where α, β, γ and δ are as defined in formulas (I)–(III) above.

The present invention may also concern a purified preparation which may comprise, consist essentially of or consist of a polynucleic acid, an expression vector or a plasmid having a sequence of the formula (V):

$$5'\text{-}\epsilon\text{-}\zeta\text{-}\iota\text{-}\kappa\text{-}\xi\text{-}3' \qquad (V)$$

where ε, which is optionally present, is a 5'-terminal polynucleotide sequence which provides a means for operationally expressing the polynucleotides α, β, γ and δ; ζ is a polynucleotide of the formula KTVACC, where K is T, G or U, and V is A, G or C; ι is a polynucleotide of at most about 130 (preferably at most 100) nucleotides in length; κ is a polynucleotide comprising one or more genes selected from the group consisting of a conventional marker or reporter gene, α, β, γ, and operationally linked combinations thereof, where α, β, and γ are as defined in formulas (I)–(IV) above; and ξ, which is optionally present, is a 3'-terminal polynucleotide sequence which does not suppress the operational expression of the polynucleotides α, β, γ and δ, and which may be operationally linked to ε (for example, in a plasmid).

Suitable marker or reporter genes include, e.g., those providing resistance to an antibiotic such as neomycin, erythromycin or chloramphenicol; those encoding a known, detectable enzyme such as β-lactamase, DHFR, horseradish peroxidase, glucose-6-phosphate dehydrogenase, alkaline phosphatase, and enzymes disclosed in U.S. Pat. No. 4,190, 496, col. 32, line 33 through col. 38, line 44 (incorporated herein by reference), etc.; and those encoding a known antibody (e.g., mouse IgG, rabbit IgG, rat IgG, etc.) or known antigenic protein such as Protein A, Protein G, bovine serum albumin (BSA), keyhole limpet hemocyanin (KLH), bovine gamma globulin (BGG), lactalbumin, polylysine, polyglutamate, lectin, etc.

The polynucleotide ι is preferably a polynucleotide sequence at least 80% homologous to a polynucleotide sequence from a PRRSV genome located between a leader-mRNA junction sequence and the start codon of the ORF immediately downstream. "About 130" nucleotides in length refers to a length of the polynucleotide κ which does not adversely affect the operational expression of ι. For example, in ISU 79, a leader-mRNA junction sequence which does not suppress expression of ORF 7 can be found 129 bases upstream from the start codon of ORF 7 (see Experiment 2 below). Suitable exemplary sequences for the polynucleotide ι can be deduced from the sequences shown in FIGS. 1 and 9.

The present polynucleic acid may also comprise, consist essentially of or consist of combinations of the above sequences, either as a mixture of polynucleotides or covalently linked in either a head-to-tail (sense-antisense) or head-to-head fashion. Polynucleic acids complementary to the above sequences and combinations thereof (antisense polynucleic acid) are also encompassed by the present invention. Thus, in addition to possessing multiple or variant copies of ORF 5, the present polynucleic acid may also contain multiple or variant copies of one or more of ORF's 1–7, including antigenic or hypervariable regions of ORF 5, of Iowa strain PRRSV's.

Similar to the methods described above and in the Experiments described below and in U.S. application Ser. Nos. 08/131,625 and 08/301,435, one can prepare a library of recombinant clones (e.g., using E. coli as a host) containing suitably prepared restriction fragments of a PRRSV genome (e.g., inserted into an appropriate plasmid expressible in the host). The clones are then screened with a suitable probe (e.g, based on a conserved sequence of ORF's 2–3; see, for example, FIG. 22 of U.S. application Ser. No. 08/301,435). Positive clones can then be selected and grown to an appropriate level. The polynucleic acids can then be isolated from the positive clones in accordance with known methods. A suitable primer for PCR can then be designed and prepared as described above to amplify the desired region of the polynucleic acid. The amplified polynucleic acid can then be isolated and sequenced by known methods.

The present purified preparation may also contain a polynucleic acid selected from the group consisting of sequences having at least 97% sequence identity (or homology) with at least one of ORFs 5–7 of VR 2385, VR 2430 and/or VR 2431; and sequences encoding a polypeptide having at least the minimum sequence identity (or homology) with at least one of ORF's 2–5 of VR 2385, VR 2428, VR 2429, VR 2430, VR 2431, VR 2474 and ISU-1894, as follows:

TABLE 2

| Relative to Isolate: | Minimum % Homology with ORF: | | | |
|---|---|---|---|---|
| | 2 | 3 | 4 | 5 |
| VR 2385 | 99 | 92 | 95 | 90 |
| VR 2429 | 100 | 99 | 99 | 98 |
| VR 2430 | 98 | 95 | 96 | 90 |
| VR 2431 | 94 | 88 | 93 | 92 |
| VR 2474 | 99 | 97 | 97 | 95 |
| ISU 1894 | 97 | 97 | 99 | 97 |

Preferably, the polynucleic acid excludes or modifies a sufficiently long region or portion of one or more of ORFs 2–4 of the hv PRRSV isolates VR 2385, VR 2429, ISU-28, ISU-79 and/or ISU-984 to render the isolate low-virulent or non-virulent.

In the context of the present application, "homology" refers to the percentage of identical nucleotide or amino acid residues in the sequences of two or more viruses, aligned in accordance with a conventional method for determining homology (e.g., the MACVECTOR or GENEWORKS computer programs, aligned in accordance with the procedure described in Experiment III in U.S. application Ser. No. 08/301,435).

Preferably, the present isolated polynucleic acid encodes a protein, polypeptide, or antigenic fragment thereof which is at least 10 amino acids in length and in which non-homologous amino acids which are non-essential for antigenicity may be conservatively substituted. An amino acid residue in a protein, polypeptide, or antigenic fragment thereof is conservatively substituted if it is replaced with a member of its polarity group as defined below:

Basic amino acids:
   lysine (Lys), arginine (Arg), histidine (His)
Acidic amino acids:
   aspartic acid (Asp), glutamic acid (Glu), asparagine (Asn), glutamine (Gln)
Hydrophilic, nonionic amino acids:
   serine (Ser), threonine (Thr), cysteine (Cys), asparagine (Asn), glutamine (Gln)
Sulfur-containing amino acids:
   cysteine (Cys), methionine (Met)
Hydrophobic, aromatic amino acids:
   phenylalanine (Phe), tyrosine (Tyr), tryptophan (Trp)
Hydrophobic, nonaromatic amino acids:
   glycine (Gly), alanine (Ala), valine (Val), leucine (Leu), isoleucine (Ile), proline (Pro)

More particularly, the present polynucleic acid encodes one or more of the protein(s) encoded by the second, third, fourth, fifth, sixth and/or seventh open reading frames (ORF's 2–7) of the PRRSV isolates VR 2385, VR 2386, VR 2428, VR 2429, VR 2430, VR 2431, VR 2474 and/or ISU-1894 (e.g., one or more of the sequences shown in FIG. 3 and/or SEQ ID NOS:15, 17, 19, 43, 45, 47, 49, 51, 53, 55, 57, 59, 61, 63 and 65 of U.S. application Ser. No. 08/301, 435).

ORF's 6 and 7 are not likely candidates for controlling virulence and replication phenotypes of PRRSV, as the nucleotide sequences of these genes are highly conserved among high virulence (hv) and low virulence (lv) isolates (see Experiment III of U.S. application Ser. No. 08/301, 435). However, ORF 5 in PRRSV isolates appears to be less conserved among high replication (hr) and low replication (lr) isolates. Therefore, it is believed that the presence of an ORF 5 from an hr PRRSV isolate in the present polynucleic acid will enhance the production and expression of a recombinant vaccine produced from the polynucleic acid.

Furthermore, ORF 5 of PRRSV contains three hydrophilic, hypervariable regions typically associated with antigenicity in a polypeptide. Thus, the present invention also encompasses polynucleotides encoding a polypeptide comprising one or more hypervariable regions of a PRRSV ORF 5, preferably a polypeptide of the formula a-b-c-d-e-f-g, where:

a is an amino group, a poly(amino acid) corresponding to positions 1–31 of a protein encoded by a PRSSV ORF 5, or a fragment of such a poly(amino acid) which does not adversely affect the antigenicity of the polypeptide;

b is an amino acid sequence selected from the group consisting of those sequences listed under Hypervariable Region No. 1 in Table 1 above, c is an amino acid sequence corresponding to positions 39–56 of a protein encoded by a PRSSV ORF 5 (preferably a sequence of the formula LQLIYNLTLCELNGTDWL, in which (SEQ ID NO: 104) one or more [preferably 1–10] amino acids may be conservatively substituted), d is an amino acid sequence selected from the group consisting of those sequences listed under Hypervariable Region No. 2 in Table 1 above, e is an amino acid sequence corresponding to positions 67–119 of a protein encoded by a PRRSV ORF 5, in which one or more (preferably 1–20, and more preferably 1–10) amino acid residues may be conservatively substituted and which does not adversely affect the antigenicity of the polypeptide, f is an amino acid sequence selected from the group consisting of those sequences listed under Hypervariable Region No. 3 in the Table above, and g is a carboxy group (a group of the formula —COOH), an amino acid sequence corresponding to positions 129–200 of a protein encoded by a PRSSV ORF 5 or a fragment thereof which does not adversely affect the antigenicity of the polypeptide.

Accordingly, it is preferred that the present polynucleic acid, when used for immunoprotective purposes (e.g., in the preparation of a vaccine), contain at least one copy of ORF 5 from a high-replication isolate (i.e., an isolate which grows to a titer of $10^6$–$10^7$ $TCID_{50}$ in, for example, CRL 11171 cells; also see the discussions in Experiments VIII–XI U.S. application Ser. No. 08/301,435).

On the other hand, the lv isolate VR 2431 appears to be a deletion mutant, relative to hv isolates (see Experiments III and VIII–XI U.S. application Ser. No. 08/301,435). The deletion appears to be in ORF 4, based on Northern blot analysis. Accordingly, when used for immunoprotective purposes, the present polynucleic acid preferably does not contain a region of ORF 4 from an hv isolate responsible for high virulence, and more preferably, excludes the region of ORF 4 which does not overlap with the adjacent ORF's 3 and 5.

It is also known (at least for PRRSV) that neither the nucleocapsid protein nor antibodies thereto confer immunological protection against PRRSV to pigs. Accordingly, the present polynucleic acid, when used for immunoprotective purposes, contains one or more copies of one or more regions from ORF's 2, 3, 4, 5 and 6 of a PRRSV isolate encoding an antigenic region of the viral envelope protein, but which does not result in the symptoms or histopathological changes associated with PRRS when administered to a pig. Preferably, this region is immunologically cross-reactive with antibodies to envelope proteins of other PRRSV isolates.

Similarly, the protein encoded by the present polynucleic acid confers protection against PRRS to a pig administered a composition comprising the protein, and antibodies to this protein are immunologically cross-reactive with the envelope proteins of other PRRSV isolates. More preferably, the present polynucleic acid encodes the entire envelope protein of a PRRSV isolate or a protein at least 80% homologous thereto and in which non-homologous residues are conservatively substituted, or alternatively a protein at least 98% homologous thereto. Most preferably, the present polynucleotide is one of the sequences shown in FIG. 1, encompassing at least one of the open reading frames recited therein.

Relatively short segments of polynucleic acid (about 20 bp or longer) in the genome of a virus can be used to screen or identify tissue and/or biological fluid samples from infected animals, and/or to identify related viruses, by methods described herein and known to those of ordinary skill in the fields of veterinary and viral diagnostics and veterinary medicine. Accordingly, a further aspect of the present invention encompasses an isolated (and if desired, purified) polynucleic acid consisting essentially of a fragment of from 15 to 2000 bp, preferably from 18 to 1000 bp, and more preferably from 21 to 100 bp in length, derived from ORF's 2–7 of a PRRSV genome (preferably the Iowa strain of PRRSV). Particularly preferably, the present isolated polynucleic acid fragments are obtained from a terminus of one or more of ORF's 2–7 of the genome of the Iowa strain of PRRSV, and most preferably, are selected from the group consisting of the primers described in Experiments 1 and 2 below and SEQ ID NOS:1–12, 22 and 28–34 of U.S. application Ser. No. 08/301,435.

The present invention also concerns a diagnostic kit for assaying a porcine reproductive and respiratory syndrome virus, comprising (a) a first primer comprising a polynucleotide having a sequence of from 10 to 50 nucleotides in length which hybridizes to a genomic polynucleic acid from an Iowa strain of porcine reproductive and respiratory syndrome virus at a temperature of from 25 to 75° C., (b) a second primer comprising a polynucleotide having a sequence of from 10 to 50 nucleotides in length, said sequence of said second primer being found in said genomic polynucleic acid from said Iowa strain of porcine reproductive and respiratory syndrome virus and being downstream from the sequence to which the first primer hybridizes, and (c) a reagent which enables detection of an amplified polynucleic acid. Preferably, the reagent is an intercalating dye, the fluorescent properties of which change upon intercalation into double-stranded DNA.

The present isolated polynucleic acid fragments can be obtained by: (i) digestion of the cDNA corresponding to (complementary to) the viral polynucleic acids with one or more appropriate restriction enzymes, (ii) amplification by PCR (using appropriate primers complimentary to the 5'and 3'-terminal regions of the desired ORF(s) or to regions upstream of the 5'-terminus or downstream from the 3'-terminus) and cloning, or (iii) synthesis using a commercially available automated polynucleotide synthesizer.

Another embodiment of the present invention concerns one or more proteins or antigenic fragments thereof from a PRRS virus, preferably from the Iowa strain of PRRSV. As described above, an antigenic fragment of a protein from a PRRS virus (preferably from the Iowa strain of PRRSV) is at least 5 amino acids in length, particularly preferably at least 10 amino acids in length, and provides or stimulates an immunologically protective response in a pig administered a composition containing the antigenic fragment.

Methods of determining the antigenic portion of a protein are known to those of ordinary skill in the art (see the description above). In addition, one may also determine an essential antigenic fragment of a protein by first showing that the full-length protein is antigenic in a host animal (e.g., a pig). If the protein is still antigenic in the presence of an antibody which specifically binds to a particular region or sequence of the protein, then that region or sequence may be non-essential for immunoprotection. On the other hand, if the protein is no longer antigenic in the presence of an antibody which specifically binds to a particular region or sequence of the protein, then that region or sequence is considered to be essential for antigenicity.

Three hypervariable regions in ORF 5 of PRRSV have been identified by comparing the amino acid sequences of the ORF 5 product of all available PRRSV isolates (see, for example, FIG. 2D). Amino acid variations in these three regions are significant, and are not structurally conserved (FIG. 2D). All three hypervariable regions are hydrophilic and antigenic. Thus, these regions are likely to be exposed to the viral membrane and thus be under host immune selection pressure. hypervariable regions as antigenic determinants in the ORF 5 envelope protein.

The present invention also concerns a protein or antigenic fragment thereof encoded by one or more of the polynucleic acids defined above, and preferably by one or more of the ORF's of a PRRSV, more preferably of the Iowa strain of PRRSV. The present proteins and antigenic fragments are useful in immunizing pigs against PRRSV, in serological tests for screening pigs for exposure to or infection by PRRSV (particularly the Iowa strain of PRRSV), etc.

For example, the present protein may be selected from the group consisting of the proteins encoded by ORF's 2–7 of VR 2385, ISU-22 (VR 2429), ISU-55 (VR 2430), ISU-1894, ISU-79 (VR 2474) and ISU-3927 (VR 2431) (e.g., one or more of the sequences shown in FIG. 2 and/or SEQ ID NOS:15, 17, 19, 43, 45, 47, 49, 51, 53, 55, 57, 59, 61, 67, 69 and 71 of U.S. application Ser. No. 08/301,435); antigenic regions of at least one of these proteins having a length of from 5 amino acids to less than the full length of the protein; polypeptides having the minimum homology with the protein encoded by the PRSSV ORF indicated in Table 2 above; and polypeptides at least 97% homologous with a protein encoded by one of the ORF's 6–7 of VR 2385, VR 2429, VR 2430, ISU-1894, ISU-79 and VR 2431 (e.g., SEQ ID NOS:17, 19, 43, 45, 47, 49, 51, 53, 55, 57, 59 and 61 of U.S. application Ser. No. 08/301,435). Preferably, the present protein has a sequence encoded by an ORF selected from the group consisting of ORFs 2–5 of VR 2385, VR 2428, VR 2429, VR 2430, VR 2431, VR 2474 and ISU-1894 (see, for example, FIGS. 2A–D); variants thereof which provide effective immunological protection to a pig administered the same and in which from 1 to 100 (preferably from 1 to 50 and more preferably from 1 to 25) deletions or conservative substitutions in the amino acid sequence exist; and antigenic fragments thereof at least 5 and preferably at least 10 amino acids in length which provide effective immunological protection to a pig administered the same.

More preferably, the present protein variant or protein fragment has a binding affinity (or association constant) of at least 1% and preferably at least 10% of the binding affinity of the corresponding full-length, naturally-occurring protein to a monoclonal antibody which specifically binds to the full-length, naturally-occurring protein (i.e., the protein encoded by a PRRSV ORF).

The present invention also concerns a method of producing a polypeptide, comprising expressing the present polynucleic acid in an operational expression system, and purifying the expressed polypeptide from the expression system.

Suitable expression systems include those conventionally used for either in vitro or in vivo expression of proteins and polypeptides, such as a rabbit reticulocyte system for in vitro expression, and for in vivo expression, a modified or chimeric PRRSV (used to infect an infectable host cell line, such as MA-104, CRL 11171, PSP-36, PSP-36-SAH, MARC-145 and porcine alveolar macrophages), or a conventional expression vector containing the present polynucleic acid, under the operational control of a known promoter (e.g., a thymidine kinase promoter, SV40, etc.) for use in conventional expression systems (e.g., bacterial plasmids and corresponding host bacteria, yeast expression systems and corresponding host yeasts, etc.). The expressed polypeptide or protein is then purified or isolated from the expression system by conventional purification and/or isolation methods.

Other features of the invention will become apparent in the course of the following descriptions of exemplary embodiments, which are given for illustration of the invention, and are not intended to be limiting thereof.

EXAMPLE 1

Summary

The sequences of ORFs 2 to 5 of one low virulence, one "moderate" virulence and one high virulence U.S. PRRSV isolate have been determined and analyzed. Comparisons with known sequences of other PRRSV isolates show that considerable sequence variations at both nucleotide and amino acid levels exist in ORFs 2 to 5 of seven U.S. isolates with differing virulence. However, ORFs 6 and 7 of these seven U.S. isolates are highly conserved (U.S. application Ser. No. 08/301,435). Extensive sequence variations were also found in ORFs 2 to 7 between the European LV and the U.S. isolates. The least virulent U.S. PRRSV isolate known (ISU-3927) displayed the most sequence variation, in comparison with other U.S. isolates.

The phylogenetic relationship of the U.S. isolates was also analyzed. Phylogenetic analysis of the ORFs 2 to 7 of the U.S. isolates indicated that there are at least three groups of PRRSV variants (or minor genotypes) within the major U.S. PRRSV genotype. Consequently, it is highly likely that a number of additional major or minor genotypes will be identified as more virus isolates from different geographic regions are examined.

Interestingly, the least virulent U.S. isolate known (ISU 3927) forms a branch distinct from other U.S. isolates. Analysis of the nucleotide and amino acid sequences also showed that the isolate ISU 3927 exhibits the most variations in ORFs 2 to 4, relative to other U.S. isolates. Many of these variations in isolate ISU 3927 result in non-conserved amino acid substitutions. However, these non-conserved changes in isolate ISU 3927, as compared to other U.S. isolates, do not appear to be limited to a particular region; they are present throughout ORFs 2 to 4. Therefore, a specific correlation between sequence variations and viral virulence is not yet fully elucidated (although certain positions in ORF 3 appear to be possibly related to virulence; see FIG. 2B, positions 30, 48, 54–56, 134, 140, 143, 147, 153, 206, and 215; amino acids at one or more of these positions may serve as a basis for mutating other known proteins encoded by a PRRSV ORF 3).

Results

The amino acid sequence identity between seven U.S. PRRSV isolates was 91–99% in ORF 2, 86–98% in ORF 3, 92–99% in ORF 4 and 88–97% in ORF 5. The least virulent U.S. isolate known has higher sequence variations in the ORFs 2 to 4 than in ORFs 5 to 7, as compared to other U.S. isolates. Three hypervariable regions with antigenic potential were identified in the major envelope glycoprotein encoded by ORF 5.

Pairwise comparison of the sequences of ORFs 2 to 7 and phylogenetic tree analysis implied the existence of at least three groups of PRRSV variants (or minor genotypes) within the major genotype of U.S. PRRSV. The least virulent U.S. isolate known forms a distinct branch from other U.S. isolates with differing virulence. The results of this study have implications for the taxonomy of PRRSV and vaccine development.

FIG. 1 shows a nucleotide sequence comparison of ORFs 2 to 5 of U.S. isolates ISU 3927, ISU 22 and ISU 55 with other known PRRSV isolates. The nucleotide sequence of VR 2385 is shown on top, and only differences are indicated. The start codon of each ORF is indicated by +>, and the termination codon of each ORF is indicated by asterisks (*). The leader-mRNA junction sequences for subgenomic mRNAs 3, 4 and 4-1 are underlined, and the locations of the junction sequences relative to the start codon of each ORF are indicated by minus (−) numbers of nucleotides upstream of each ORF. The sequences of VR 2385 (U.S. application Ser. Nos. 08/131,625 and 08/301,435), VR 2332, ISU 79 and ISU 1894 (U.S. application Ser. No. 08/301,435) used in this alignment were previously reported.

Materials and Methods

Cells and viruses:

The ATCC CRL 11171 cell line was used to propagate the PRRSV. The cells were grown in Dulbecco's minimal essential medium (DMEM) supplemented with 10% fetal bovine serum (FBS) and 1× antibiotics (penicillin G 10,000 unit/ml, streptomycin 10,000 mg/ml and amphotericin B 25 mg/ml).

Three U.S. isolates of PRRSV used in this study, designated as ISU 22, ISU 55 and ISU 3927, were isolated from pig lungs obtained from different farms in Iowa during PRRS outbreaks. All three isolates were plaque-purified three times on CRL 11171 cells before further experimentation. Comparative pathogenicity studies showed that isolate ISU 3927 is the least virulent isolate among 10 different U.S. PRRSV isolates. Isolate ISU 22 is a high virulence isolate and isolate ISU 55 is "moderately" pathogenic. All of the three virus isolates used in this experiment were at seventh passage.

Isolation of PRRSV intracellular RNAs:

Confluent monolayers of CRL 11171 cells were infected with the three U.S. isolates of PRRSV, ISU 22, ISU 55 and ISU 3927, respectively, at a multiplicity of infection (m.o.i.) of 0.1. At 24 hrs. postinfection, the infected cells were washed three times with cold PBS buffer. The total intracellular RNAs were then isolated by guanidinium isothiocyanate and phenol-chloroform extraction (Stratagene). The presence of virus-specific RNA species in the RNA preparation was confirmed by Northern blot hybridization (data not shown). The total intracellular RNAs were quantified spectrophotometrically.

Reverse transcription and polymerase chain reaction (RT-PCR):

First strand complementary (c) DNA was synthesized from the total intracellular RNAs by reverse transcription using random primers as described previously (Meng et al., 1993, J. Vet. Diagn. Invest., 5:254–258). For amplification of the entire protein coding regions of the ORFs 2 to 5 of the three isolates of PRRSV, two sets of primers were designed on the basis of the sequences of VR 2385 and LV. Primers JM259 (5'-GGGGATCCTTTTGTGGAGCCGT-3'; SEQ ID NO:68) and JM260 (5'-GGGGAATTCGGGATAGGGAATGTG-3'; SEQ ID NO:69) amplified the sequence of ORFs 4 and 5, and primers XM992 (5'-GGGGGATCCTGTTGG-TAATAG(A) GTCTG-3'; SEQ ID NOS:70:71 and XM993 (5'-GGTGAATTCGTTTTATTTCCCTCCGGGC (SEQ ID NO:72) amplified the sequence of ORFs 2 and 4. Unique restriction sites (EcoRI or BamHI) at the 5' end of these primers were introduced to facilitate cloning. A degenerate base, G (A), was synthesized in primer XM 992 based on the sequences of VR 2385 and LV (Meulenberg et al., 1993; U.S. application Ser. No. 30 08/301,435). PCR was performed as described previously (Meng et al., 1993, J. Vet. Diagn. Invest., 5:254–258).

Cloning and nucleotide sequencing:

The RT-PCR products were analyzed by a 0.8% agarose gel electrophoresis. The two PCR fragments representing ORFs 2 and 3 as well as ORFs 4 and 5, respectively, were purified by the glassmilk procedure (GENECLEAN kit, BIO 101, Inc.). The purified fragments were each digested with BamHI and EcoRI, and cloned into the vector pSK+ as described previously (Meng et al., 1993). The E. Coli DH 5α cells were used for transformation of recombinant plasmids. White colonies were selected and grown in LB broth containing 100 mg/ml ampicillin. The E. Coli cells containing recombinant plasmid were lysed with lysozyme, and the plasmids were then isolated by using the Qiagen column (QIAGEN Inc.).

Plasmids containing viral inserts were sequenced with an automated DNA Sequencer (Applied Biosystem, Inc.). Three or more independent CDNA clones representing the entire sequence of ORFs 2 to 5 from each of the three PRRSV isolates were sequenced with universal and reverse primers. Several virus-specific primers, XM969 (5'-GATAGAGTCTGCCCTTAG-3'; SEQ ID NO: 73), XM970 (5'-GGTTTCACCTAGAATGGC SEQ ID NO: 74), XM1006 (5'-GCTTCTGAGATGAGTGA (SEQ ID NO: 75), XM077 (5'-CAACCAGGCGTAAACACT SEQ ID NO: 76) and XM078 (5'-CTGAGCAATT ACAGAAG SEQ ID NO: 77), were also used to determine the sequence of ORFs 2 to 5.

Sequence analyses:

Sequence data were combined and analyzed by using MacVector (International Biotechnologies, Inc.) and Gene-Works (IntelliGenetics, Inc.) computer software programs. Phylogenetic analyses were performed using the PAUP software package version 3.1.1 (David L. Swofford, Illinois Natural History Survey, Champaign, Ill.). PAUP employs the maximum parsimony algorithm to construct phylogenetic trees.

Results

Nucleotide sequence analyses of ORFs 2 to 5:

The sequences of ORFs 2 to 5 of five PRRSV isolates, ISU 79, ISU 1894, ISU 22, ISU 55 and ISU 3927, were determined and compared with other known PRRSV isolates including VR 2385, VR 2332 and LV (Meulenberg et al., 1993). The sequences of ORFs 6 and 7 of isolates VR 2385, ISU 22, ISU 55, ISU 79, ISU 1894 and ISU 3927 were reported previously (U.S. application Ser. No. 08/301,435). The isolates used in this experiment have been shown to differ in pneumovirulence in experimentally-infected pigs (U.S. application Ser. Nos. 08/131,625 and 08/301,435). ISU 3927 is the least virulent isolate among ten different U.S. PRRSV isolates (U.S. application Ser. Nos. 08/131,625 and 08/301,435).

Like other U.S. PRRSV isolates, ORFs 2 to 4 of these isolates overlapped each other (FIG. 1). However, unlike LV, ORFs 4 and 5 of the U.S. isolates are separated by 10 nucleotides (FIG. 1). ORFs 4 and 5 of LV overlapped by one nucleotide. The single nucleotide substitution from A of the start codon of ORF 5 in LV to T in the U.S. isolates places the start codon of ORF 5 of the U.S. isolates 10 nucleotides downstream of the ORF 4 stop codon. Therefore, a 10-nucleotide noncoding sequence appears between ORFs 4 and 5 of the known U.S. isolates (FIG. 1).

ORF 2 of ISU 79 is 3 nucleotides shorter than other U.S. isolates. The single nucleotide substitution from TGG to TAG just before the stop codon of ORF 2 creates a new stop codon in ISU 79 (FIG. 1). A 3-nucleotide deletion was also found in ORF 5 of ISU 3927, compared to other U.S. isolates (FIG. 1). The size of ORFs 2 to 5 of all the U.S. isolates are identical, except for the ORF 2 of ISU 79 and ORF 5 of ISU 3927, both of which are 3 nucleotides shorter than the other ORFs (FIG. 1).

Sequence comparisons of ORFs 2 to 5 of the seven U.S. PRRSV isolates shown in FIG. 1 indicate that there are considerable nucleotide sequence variations in ORFs 2 to 5 of the U.S. isolates (FIG. 1). The nucleotide sequence identity was 96–98% in ORF 2, 92–98% in ORF 3, 92–99% in ORF 4, and 90–98% in ORF 5 between VR 2385, VR 2332, ISU 22, ISU 55, ISU 79, and ISU 1894 (Table 3).

The least virulent isolate ISU 3927 has the most variations among the seven U.S. isolates (FIG. 1 and Table 3). The nucleotide sequence identity between ISU 3927 and other U.S. isolates was 93–94% in ORF 2, 89–90% in ORF 3, and 91–93% in ORF 4 (Table 3). Like ORFs 6 and 7 (U.S. application Ser. No. 08/301,435), ORF 5 of ISU 3927 has no significant changes except for a 3-nucleotide deletion (FIG. 1). ORF 5 of ISU 3927 shares 91–93% nucleotide sequence identity with the ORF 5 of other U.S. isolates (Table 3).

However, extensive sequence variation was found in ORFs 2 to 5 between LV and the U.S. isolates (FIG. 1 and Table 3). The nucleotide sequence identity between LV and the U.S. isolates was 65–67% in ORF 2, 61–64% in ORF 3, 63–66% in ORF 4, and 61–63% in ORF 5 (Table 3). Extensive genetic variations in ORFs 6 and 7 between LV and U.S. PRRSV also exists (U.S. application Ser. Nos. 08/131,625 and 08/301,435). These results indicate that the least virulent isolate ISU 3927 is also the most distantly related of the U.S. isolates, with genetic variations occurring mostly in ORFs 2 to 4.

The single nucleotide substitution from TGG to TAG before the stop codon in ORF 2 observed in ISU 79 was also present in isolates ISU 55 and ISU 3927, both of which produce seven sg mRNAs, but not in isolates ISU 22, ISU 1894 or VR 2385, which each synthesize only six sg mRNAs (U.S. application Ser. Nos. 08/131,625 and 08/301,435). The results indicate that the leader-mRNA 4-1 junction sequence of ISU 55 and ISU 3927 is very likely to be the same as ISU 79 (FIG. 1).

The leader-mRNA junction sequences for sg mRNAs 3 and 4 of ISU 79 and ISU 1894 were determined to be GUAACC at 89 nucleotides upstream of ORF 3 for sg mRNA 3, and UUCACC at 10 nucleotides upstream of ORF 4 for sg mRNA 4 (U.S. application Ser. No. 08/301,435; see also Experiment 2 below). A sequence comparison of isolates ISU 22, ISU 55 and ISU 3927 with isolates VR 2385, ISU 79 and ISU 1894 indicates that the leader-mRNA junction sequences for sg mRNAs 3 and 4 are conserved among the U.S. isolates (FIG. 1).

Analysis of the deduced amino acid sequences encoded by ORFs 2 to 5:

FIG. 2 shows the alignment of the deduced amino acid sequences of ORF 2 (A), ORF 3 (B), ORF 4 (C) and ORF 5 (D) of U.S. isolates ISU 22, ISU 55 and ISU 3927 with other known PRRSV isolates. The sequence of VR 2385 is shown on top, and only differences are indicated. Deletions are indicated by (-). The proposed signal peptide sequence in the ORF 5 of LV (D) is underlined (Meulenberg et al., 1995). Three hypervariable regions with antigenic potentials in ORF 5 (D) were indicated by asterisks (*). The published sequences used in this alignment were LV (Meulenberg et al., 1993), VR 2385 (U.S. application Ser. Nos. 08/131,625 and 08/301,435), VR 2332, ISU 79 and ISU 1894 (U.S. application Ser. No. 08/301,435).

On the basis of its high content of basic amino acids and its hydrophilic nature, the translation product of ORF 7 is predicted to be the nucleocapsid protein (U.S. application Ser. Nos. 08/131,625 and 08/301,435; Meulenberg et al., 1993; Conzelmann et al., 1993; Mardassi et al., 1994). The ORF 6 product lacks a potential amino-terminal signal sequence and contains several hydrophobic regions which may represent the potential transmembrane fragments. Therefore, the ORF 6 product was predicted to be the M protein (U.S. application Ser. Nos. 08/131,625 and 08/301, 435; Meulenberg et al., 30 1993; Conzelmann et al., 1993).

Computer analysis shows that the products encoded by ORFs 2 to 5 of the U.S. isolates all have hydropathy characteristics reminiscent of membrane-associated proteins. The translation products of ORFs 2 to 5 each contain a hydrophobic amino terminus. The N-terminal hydrophobic sequences may function as a signal sequence for each of these ORFs, and they may be involved in the transportation of ORFs 2 to 5 to the endoplasmic reticulum of infected cells. At least one additional hydrophobic domain in each of ORFs 2 to 5 was found at the carboxy termini. These additional hydrophobic domains may function as membrane anchors.

The deduced amino acid sequences of ORFs 2 to 5 of the seven U.S. isolates examined also varied considerably (FIG. 2), indicating that most of the nucleotide differences observed in FIG. 1 are not silent mutations. The amino acid sequence identity between VR 2385, VR 2332, ISU 22, ISU 55, ISU 79, and ISU 1894 was 95–99% in ORF 2, 90–98% in ORF 3, 94–98% in ORF 4, and 88–97% in ORF 5 (Table 3).

Again, the least virulent isolate ISU 3927 displayed more variations with other U.S. isolates in ORFs 2 to 4 (FIG. 2 and Table 3) than in ORFs 5 to 7 (U.S. application Ser. No. 08/301,435 and Table 3). ORFs 2 to 5 of LV share only 57–61%, 55–56%, 65–67%, and 51–55% amino acid sequence identity with those ORFs of the U.S. isolates, respectively (Table 3). Deletions or insertions were found throughout ORFs 2 to 5 in comparing European LV and U.S. isolates (FIG. 2).

Sequence comparison of the ORF 5 product showed that the N-terminal region of ORF 5 is extremely variable, both (a) between U.S. isolates and LV and also (b) among the various U.S. isolates (FIG. 2D). In LV, the first 32–33 amino acid residues of ORF 5 may represent the signal sequence (Meulenberg et al., 1995; FIG. 2D). Therefore, the potential signal sequence of ORF 5 in all the PRRSV isolates is very heterogeneous. This heterogeneity is not due to any host immune selection pressure, because the signal peptide will be cleaved out and not be present in mature virions.

Three additional hypervariable regions were also identified by comparing the amino acid sequences of ORF 5 of all the PRRSV isolates available (FIG. 2D). Amino acid variations in these three regions are significant, and are not structurally conserved (FIG. 2D). Computer analysis indicates that all three hypervariable regions are hydrophilic and antigenic. Thus, it is likely that these regions are exposed to the viral membrane and are under host immune selection pressure. However, further experiments may be necessary to confirm the specific functions of these hypervariable regions as antigenic determinants in the ORF 5 envelope protein.

The Phylogenetic relationships among U.S. isolates of PRRSV:

It has been shown previously that U.S. PRRSV and European PRRSV represent two distinct genotypes, based on analysis of the M and N genes (U.S. application Ser. No. 08/301,435). To determine the phylogenetic relationships of U.S. PRRSV isolates, ORFs 2 to 7 of the seven U.S. PRRSV isolates shown in FIGS. 1 and 2 were first aligned with the GeneWorks program (intelligenetics, Inc.). The PAUP program (David L. Swofford, Illinois Natural History Survey, Champaign, Ill.) was then used to construct phylogenetic tree illustrating relationship among U.S. isolates of PRRSV.

The phylogenetic tree of FIG. 3 was constructed by maximum parsimony methods with the aid of the PAUP software package version 3.1.1. The branch with the shortest length (most parsimonious) was found by implementing the exhaustive search option. The branch lengths (numbers of amino acid substitutions) are given above each branch. The sequences used in the analysis are LV, VR 2385, VR 2332, ISU 79 and ISU 1894.

The phylogenetic tree indicates that at least three groups of variants (or minor genotypes) exist within the major U.S. PRRSV genotype. The least virulent U.S. PRRSV isolate ISU 3927 forms a branch distinct from other U.S. isolates (FIG. 3). Isolates ISU 22, ISU 79, ISU 1894, and VR 2332 form another branch, representing a second minor genotype. The third minor genotype is represented by isolates ISU 79 and VR 2385 (FIG. 3). A very similar tree was also obtained by analyzing the last 60 nucleotides of ORF 1b of the seven U.S. isolates presented in FIG. 1 (data not shown). Identical tree topology was also produced by the unweighted pair-group method with arithmetic mean (UPGMA) using the GeneWorks program (data not shown).

In summary, the different genotypes of PRRSV have been confirmed and further elucidated. At least three minor genotypes within the major genotype of U.S. PRRSV have been identified, based on an analysis of the sequence of ORFs 2 to 7. Genetic variations not only between the European PRRSV and the U.S. PRRSV but among the U.S. PRRSV isolates have also been further confirmed as well, indicating the heterogeneous nature of PRRSV. The least virulent U.S. PRRSV isolate ISU 3927 has unexpectedly high sequence variations in ORFs 2 to 4, as compared to other U.S. isolates.

TABLE 3

Nucleotide and deduced amino acid sequence identities (%) of ORFs 2 to 5 of PRRSV

|  | VR2385 | ISU22 | ISU55 | ISU79 | ISU1894 | ISU3927 | VR2332 | LV |
|---|---|---|---|---|---|---|---|---|
| ORF 2 |  |  |  |  |  |  |  |  |
| VR2385 | ** | 97 | 96 | 96 | 95 | 91 | 98 | 58 |
| ISU22 | 97 | ** | 96 | 98 | 96 | 93 | 99 | 59 |
| ISU55 | 98 | 97 | ** | 96 | 95 | 91 | 97 | 61 |

TABLE 3-continued

Nucleotide and deduced amino acid sequence
identities (%) of ORFs 2 to 5 of PRRSV

|         | VR2385 | ISU22 | ISU55 | ISU79 | ISU1894 | ISU3927 | VR2332 | LV |
|---------|--------|-------|-------|-------|---------|---------|--------|-----|
| ISU79   | 96     | 97    | 97    | **    | 96      | 91      | 98     | 60 |
| ISU1894 | 96     | 97    | 96    | 96    | **      | 93      | 96     | 57 |
| ISU3927 | 94     | 94    | 94    | 93    | 93      | **      | 93     | 58 |
| VR2332  | 97     | 98    | 97    | 98    | 97      | 94      | **     | 59 |
| LV      | 65     | 66    | 66    | 67    | 66      | 65      | 66     | ** |
| ORF 3   |        |       |       |       |         |         |        |    |
| VR2385  | **     | 91    | 94    | 92    | 90      | 87      | 91     | 55 |
| ISU22   | 92     | **    | 93    | 96    | 96      | 88      | 98     | 56 |
| ISU55   | 94     | 93    | **    | 94    | 93      | 87      | 94     | 56 |
| ISU79   | 94     | 96    | 94    | **    | 95      | 87      | 96     | 56 |
| ISU1894 | 92     | 97    | 93    | 96    | **      | 86      | 96     | 55 |
| ISU3927 | 90     | 90    | 89    | 90    | 90      | **      | 87     | 55 |
| VR2332  | 93     | 98    | 94    | 97    | 97      | 90      | **     | 56 |
| LV      | 64     | 63    | 62    | 63    | 63      | 61      | 63     | ** |
| ORF 4   |        |       |       |       |         |         |        |    |
| VR2385  | **     | 94    | 96    | 94    | 95      | 83      | 94     | 66 |
| ISU22   | 93     | **    | 94    | 97    | 99      | 93      | 98     | 66 |
| ISU55   | 96     | 94    | **    | 96    | 96      | 93      | 95     | 67 |
| ISU79   | 93     | 97    | 94    | **    | 98      | 92      | 96     | 66 |
| ISU1894 | 92     | 98    | 94    | 96    | **      | 93      | 98     | 66 |
| ISU3927 | 91     | 93    | 92    | 91    | 91      | **      | 92     | 67 |
| VR2332  | 94     | 99    | 95    | 97    | 98      | 92      | **     | 65 |
| LV      | 66     | 66    | 63    | 65    | 66      | 65      | 65     | ** |
| ORF 5   |        |       |       |       |         |         |        |    |
| VR2385  | **     | 90    | 91    | 88    | 89      | 91      | 89     | 54 |
| ISU22   | 93     | **    | 90    | 94    | 96      | 92      | 97     | 52 |
| ISU55   | 94     | 92    | **    | 89    | 89      | 90      | 89     | 51 |
| ISU79   | 91     | 95    | 91    | **    | 95      | 89      | 94     | 53 |
| ISU1894 | 92     | 97    | 90    | 94    | **      | 91      | 96     | 53 |
| ISU3927 | 91     | 93    | 91    | 91    | 91      | **      | 91     | 55 |
| VR2332  | 93     | 98    | 91    | 95    | 97      | 92      | **     | 53 |
| LV      | 63     | 63    | 63    | 61    | 62      | 63      | 63     | ** |

Note:
The amino acid sequence comparisons are presented in the upper right half, and the nucleotide sequence comparisons are presented in the lower left half.

EXAMPLE 2

During the replication of PRRSV, six subgenomic mRNAs (sg mRNAs), in addition to the genomic RNA, are synthesized. These sg mRNAs were characterized in this experiment.

The sg mRNAs of PRRSV form a 3'-coterminal nested set in PRRSV-infected cells. Each of these sg mRNAs is polycistronic and contains multiple open reading frames, except for sg mRNA 7 (as shown by Northern blot analysis using ORF-specific probes). The sg mRNAs were not packaged into virions, and only the genomic RNA was detected in purified virions, suggesting that the encapsidation signal of PRRSV is likely localized in the ORF 1 region.

The numbers of sg mRNAs in PRRSV-infected cells varies among PRRSV isolates with differing virulence. An additional species of sg mRNA in some PRRSV isolates was shown in Experiment 1 above to be derived from the sequence upstream of ORF 4, and has been designated as sg mRNA 4-1.

The leader-mRNA junction sequences of sg mRNAs 3 and 4 of isolates ISU 79 and ISU 1894, as well as sg mRNA 4-1 of the isolate ISU 79, contain a common six nucleotide sequence motif, T(G)TA(G/C)ACC. Sequence analysis of the genomic RNA of these two U.S. isolates and comparison with Lelystad virus (LV) revealed heterogeneity of the leader-mRNA junction sequences among PRRSV isolates. The numbers, locations and the sequences of the leader-mRNA junction regions varied between U.S. isolates and LV, as well as among U.S. isolates. The last three nucleotides, ACC, of the leader-mRNA junction sequences are invariable. Variations were found in the first three nucleotides.

By comparing the 5'-terminal sequence of sg mRNA 4-1 with the genomic sequence of ISU 79 and ISU 1894, it was found that a single nucleotide substitution, from T in ISU 1894 to C in ISU 79, led to a new leader-mRNA junction sequence in ISU 79, and therefore, an additional species of sg mRNA (sg mRNA 4-1). A small ORF, designated as ORF 4-1, with a coding capacity of 45 amino acids was identified at the 5'-end of sg mRNA 4-1.

Materials and Methods

Viruses and cells. The PRRSV isolates used (ISU 22, ISU 55, ISU 79, ISU 1894 and ISU 3927) were isolated from pig lungs obtained from different farms in Iowa. A continuous cell line, ATCC CRL 11171, was used for isolation and growth (culturing) of viruses. These PRRSV isolates were biologically cloned by three rounds of plaque purification and grown on the CRL 11171 cells. All of the virus isolates used in this study were at the seventh passage.

ISU 22 and ISU 79 are highly pathogenic and produce from 50 to 80% consolidation of the lung tissues in experimentally-infected five-week-old caesarean-derived colostrum-deprived pigs necropsied at 10 days post-inoculation. By contrast, ISU 55, ISU 1894 and ISU 3927 are of low pathogenicity and produce only 10 to 25% consolidation of lung tissues in the same experiment (U.S. application Ser. Nos. 08/131,625 and 08/301,435).

Preparation of virus-specific total intracellular RNAs, poly $(A)^+$ RNA and virion RNA. Confluent monolayers of CRL 11171 cells were infected with different isolates of PRRSV at the seventh passage at a multiplicity of infection (m.o.i.) of 0.1. PRRSV-specific total intracellular RNAs were isolated from PRRSV-infected cells by a conventional guanidinium isothiocyanate method (Stratagene). The poly $(A)^+$ RNA was enriched from the total intracellular RNAs by oligo (dT)-cellulose column chromatography (Invitrogen).

For isolation of PRRSV virion RNA, confluent CRL 11171 cells were infected with isolate ISU 3927 of PRRSV at a m.o.i. of 0.1. When more than 70% of the infected cells showed a cytopathic effect, the cultures were frozen and thawed three times, and the culture medium was clarified at 1200×g for 20 min. at 4° C. The virus was then precipitated with polyethylene glycol and subsequently purified by cesium chloride gradient centrifugation as described in U.S. application Ser. No. 08/131,625. The purified virus was treated with RNase A at a final concentration of 20 $\mu$/ml for 90 min. at 37° C. The virus was then pelleted, and the virion RNA was isolated using a conventional guanidinium isothiocyanate method.

cDNA synthesis and polymerase chain reaction. cDNA was synthesized from total intracellular RNAs by reverse transcription using random primers and amplified by the polymerase chain reaction (RT-PCR) as described previously (Meng et al., 1993, J. Vet. Diagn. Invest., 5:254–258).

Northern blot analyses. Ten $\mu$g of total intracellular RNAs from virus infected cells and mock-infected cells were used per lane in a formaldehyde-agarose gel. For separation of poly $(A)^+$ RNA and virion RNA, fifteen ng of virion RNA and 0.2 $\mu$g of poly $(A)^+$ RNA were loaded per lane. The RNA was denatured with formaldehyde according to a conventional method (Sambrook et al, "Molecular Cloning: A Laboratory Manual", 2nd ed., Cold Spring Harbor Laboratory, Cold Spring Harbor, N.Y.). Electrophoretic separation of RNA, RNA blotting, and hybridization were performed as described in U.S. application Ser. No. 08/131,625. In some experiments, glyoxal-DMSO agarose gels were also performed as described in U.S. application Ser. No. 08/131,625.

For preparation of probes, a specific cDNA fragment from each of the ORFs 1b to 7 was generated by RT-PCR with ORF-specific primers. The primers were designed in such a way that each primer pair amplifies only a specific fragment of a given ORF, and the overlapping, neighboring ORFs are not included in any given cDNA probe. The primer pairs for generating cDNA probes representing ORFs 1b through 7 are IM729/IM782 for ORF 1b, IM312/IM313 for ORF 2, XM1022/IM258 for ORF 3, XM1024/XMI 023 for ORF 4, PP287/PP286 for ORF 5, PP289/XM780 for ORF 6, and PP285/PP284 for ORF 7 (Table 4).

Cloning, sequencing and nucleotide sequence analyses. Primers for RT-PCR were designed on the basis of PRRSV isolate VR 2385 sequences, which amplified the entire protein coding regions of ORFs 2 to 5 of PRRSV isolates ISU 79 and ISU 1894. Primers JM259 and JM260 were used for amplification of ORFs 4 and 5, and XM992 and XM993 for amplification of ORFs 2 and 3 (Table 4). Unique restriction sites (EcoRI and BamHI) at the termini of the PCR products were introduced, thus enabling a cassette approach to replacement of these ORFs.

The PCR products of ORFs 2–3 and ORFs 4–5 of ISU 79 and ISU 1984 were each digested with EcoRI and BamHI, then purified and cloned into vector pSK+ as described previously (Meng et al., 1993, J. Vet. Diagn. Invest., 5:254–258). Plasmids containing viral inserts were sequenced with a conventional automated DNA sequencer (Applied Biosystem, Inc.). At least three cDNA clones representing the entire sequence of ORFs 2 to 5 from each virus isolate were sequenced with universal and reverse primers, as well as other virus-specific sequencing primers (XM969, XM970, XM1006, XM078 and XM077; see Table 4).

To determine the leader-mRNA junction sequences of sg mRNAs 3, 4 and 4-1, primer pair IM755 and DP586 (Table 4) was used for RT-PCR to amplify the corresponding 5'-terminal sequences. The resulting PCR products were purified and sequenced by direct PCR sequencing using virus specific primers XMD77 and XM141 (Table 4). The sequences were combined and analyzed by MacVector (International Biotechnologies, Inc.) and GeneWorks (IntelliGenetics, Inc) computer software programs.

Oligonucleotides. The synthetic oligonucleotides used in this study were summarized in Table 4. These oligonucleotides were synthesized as single stranded DNA using an automated DNA synthesizer (Applied Biosystem) and purified by high pressure liquid chromatography (HPLC).

Results

Sg mRNAs are not packaged into PRRSV virions. To determine whether the sg mRNAs of PRRSV are packaged, virions of PRRSV isolate ISU 3927 were purified by CsCl gradient. The purified virions were treated with RNase A before pelleting the virion and extracting RNA, to remove any RNA species which may have adhered to the virion surface. RNAs from RNase A-treated virions along with the total intracellular RNAs from isolate ISU 3927 of PRRSV-infected cells were separated in a formaldehyde gel and hybridized with a probe generated from the 3'-terminal sequence of the viral genome by PCR with primers PP284 and PP285 (U.S. application Ser. No. 08/131,625; Table 4).

Figure 4:
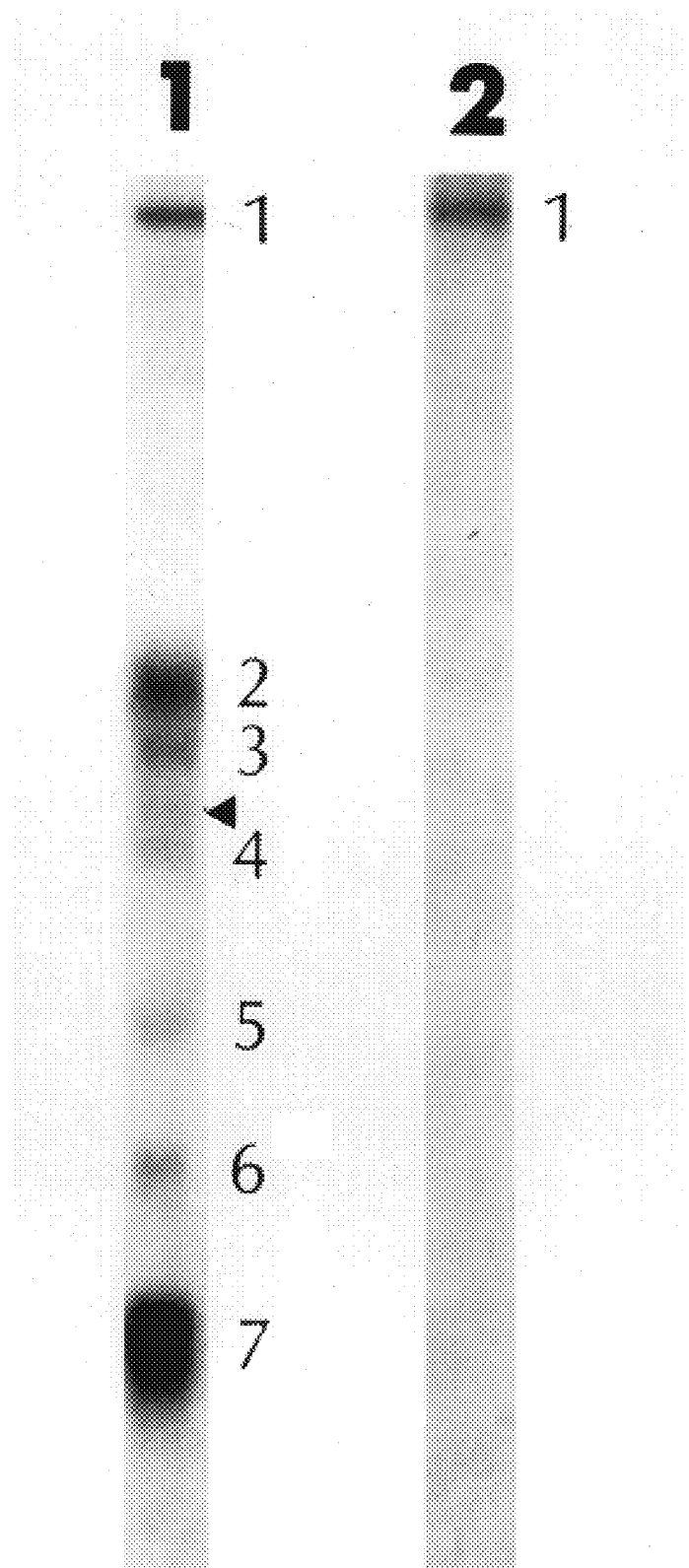
FIG. 4 shows a Northern blot analysis of RNAs isolated from ISU 3927-infected CRL 11171 cells (lane 1) and from purified virions of ISU 3927 (lane 2)

Only the genomic RNA was detected in the purified virions of PRRSV isolate ISU 3927 (FIG. 4), and no detectable amounts of sg mRNAs were observed in the purified virions even after 3 weeks exposure. In contrast, seven species of sg mRNAs, in addition to the genomic RNA, were detected in ISU 3927-infected cells (FIG. 4). Similar results were observed with two other U.S. isolates, ISU 55 and ISU 79.

Variation in the numbers of the sg mRNAs among U.S. PRRSV isolates with differing virulence. All arteriviruses known prior to the present invention, including U.S. PRRSV and European PRRSV, have been shown to produce six sg mRNAs, except for three LDV variants (LDV-P, LDV-a and LDV-v), which synthesize seven sg mRNAs. However, a nested set of six sg mRNAs is produced in the LDV-C strain.

To compare if there are any variations in the sg mRNAs among U.S. PRRSV isolates, confluent monolayers of CRL 11171 cells were infected with five different isolates of U.S. PRRSV with differing virulence at a m.o.i. of 0.1. Total intracellular RNAs were isolated from virus-infected cells at 24 h post-infection. A cDNA fragment was generated from the extreme 3'-end of the viral genome by PCR with primers PP284 and PP285 (Table 4). The cDNA fragment was labelled with $^{32}$p-dCTP by the random primer extension method, and hybridized with the total intracellular RNAs (separated on a formaldehyde gel).

Analyses of the RNAs showed that a nested set of six or more sg mRNAs, in addition to the genomic RNA, was present in cells infected with one of the five isolates of U.S.

Figure 5:
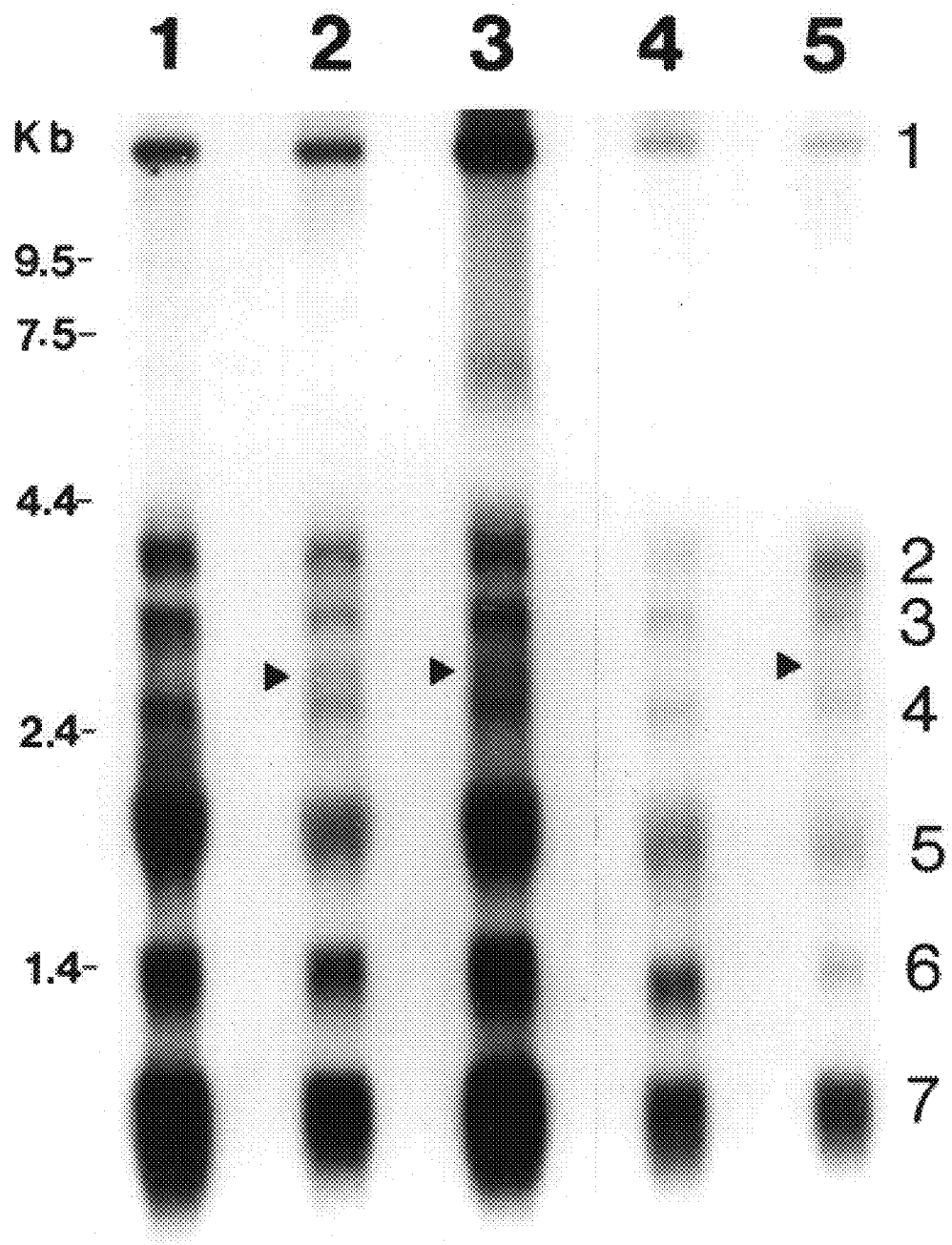
FIG. 5 shows a Northern blot analysis of total intracellular RNAs isolated from CRL 11171 cells infected with ISU22 (lane 1), ISU 55 (lane 2), ISU 79 (lane 3), ISU 1894 (lane 4) and ISU 3927 (lane 5), respectively.

PRRSV with differing virulence (FIG. 5). Similar results were obtained when the total intracellular RNAs were separated on a glyoxal-DMSO agarose gel. PRRSV isolates ISU 55, ISU 79 and ISU 3927 produced seven easily distinguishable sg mRNAs, whereas isolates ISU 22 and ISU 1894 produced six sg mRNAs (FIG. 5). The U.S. PRRSV isolate VR 2385 also produces six sg mRNAs (U.S. application Ser. No. 08/131,625). An additional species of sg mRNA was located between sg mRNAs 3 and 4, and was designated as sg mRNA 4-1. The sg mRNAs differed little, if any, in size among the five isolates of PRRSV (FIG. 5). There appears to be no correlation, however, between the pneumovirulence and the numbers of the sg mRNAs observed in these five isolates.

Sg mRNA 4-1 is not a defective-interfering RNA and is not a result of nonspecific binding of the probes to ribosomal RNAs. It has been shown that, in coronaviruses, a variety of defective interfering RNA (DI RNA) of different sizes were generated when MHV was serially passaged in tissue culture at a high m.o.i. DI RNAs were also observed in cells infected with torovirus during undiluted passage. Therefore, the possibility of sg mRNA 4-1 of PRRSV being a DI RNA was investigated.

To exclude this possibility, the original virus stock of PRRSV isolate ISU 79, which produces the additional species of sg mRNA 4-1, was passaged four times in CRL 11171 cells at different m.o.i. of 0.1, 0.01 and 0.001, respectively. In a control experiment, four undiluted passages of the original virus stock of ISU 79 were performed. After four passages, total intracellular RNAs were isolated from virus-infected cells and Northern blot analysis was repeated with the same probe generated from the extreme 3'-end of the viral genome.

Figures 6A, 6B:
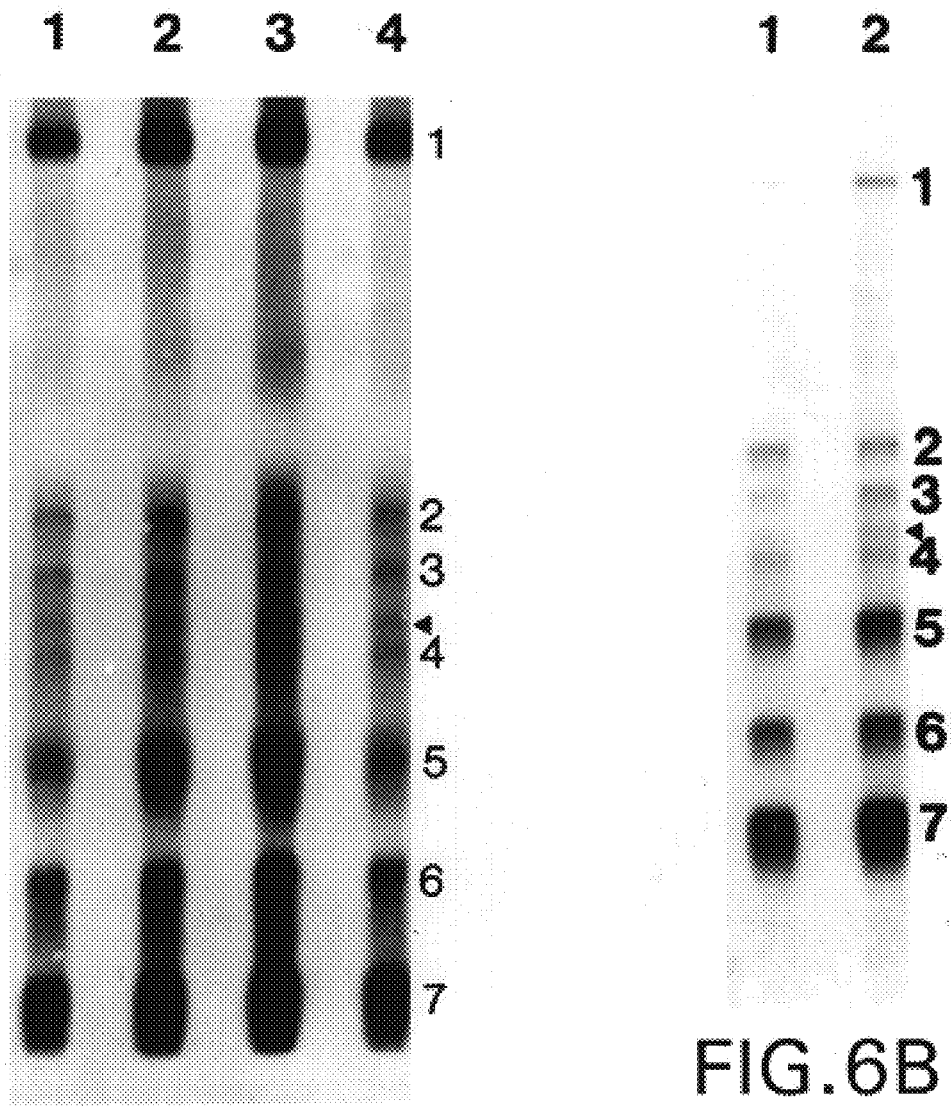
FIGS. 6A and 6B show a Northern hybridization of total RNAs isolated from CRL 11171 cells infected with ISU 79 at different multiplicities of infection (m.o.i.) (A), and polyadenylated RNA from cells infected with PRRSV isolates ISU 55 and ISU 79 (B)

Analyses of the sg mRNAs showed that the additional species of sg mRNA 4-1 was still present in all RNA preparations with different m.o.i., as well as in RNA preparations from undiluted passages (FIG. 6A). Moreover, there was no interference or reduction in the synthesis of other sg mRNAs in the presence of sg mRNA 4-1, as is usually the case with DI RNA.

It has been demonstrated that the DI RNAs of MHV disappeared after two high-dilution passages. Therefore, if the original virus stock of ISU 79 contained DI RNA, then the DI RNA should disappear after four high-dilution passages. The experimental data above suggests that, unlike DI RNA, the replication of sg mRNA 4-1 is independent of the amount of standard virus. Thus, sg mRNA 4-1 is not a DI RNA.

In Northern blot analysis of total intracellular RNAS, the probes may nonspecifically bind to the 18S and 28S ribosomal RNAs, which are abundant in total cytoplasmic RNA preparations. Alternatively, the abundant ribosomal RNAs may cause retardation of virus-specific sg mRNAs which may co-migrate corrugate with the ribosomal RNAs in the gel.

Two additional bands due to the nonspecific binding of probes to the ribosomal RNAs have been observed in LV-infected cells and LDV-infected cells. Therefore, it is possible that sg mRNA 4-1 of PRRSV is due to the nonspecific binding of probes to the ribosomal RNAS.

To rule out this possibility, polyadenylated RNA was isolated from total intracellular RNAs of CRL 11171 cells infected with either of two PRRSV isolates, ISU 55 and ISU 79. Both ISU 55 and ISU 79 produce the additional species of sg mRNA 4-1 (FIG. 5). Northern blot analysis of the polyadenylated RNA showed that the additional species of sg mRNA 4-1 in cells infected with either of these two isolates was still present (FIG. 6B), indicating that sg mRNA 4-1 is not due to the nonspecific binding of a probe to the ribosomal RNAS.

The sg mRNAs represent a 3'-coterminal nested set and the sg mRNA 4-1 is derived from the sequence upstream of ORF 4. Six sg mRNAs, in addition to the genomic RNA, are detected in cells infected with VR 2385 using a cDNA probe from the extreme 3'-end of the viral genome (U.S. application Ser. No. 08/131,625). Thus, like Berne virus (BEV), LDV, EAV, coronaviruses and LV, the replication of U.S. PRRSV also requires the synthesis of a 3'-coterminal nested set of sg mRNAs (U.S. application Ser. Nos. 08/131,625 and 08/301,435).

To analyze these sg mRNAs in more detail, seven cDNA fragments specific for each of ORFs 1b through 7 were amplified by PCR. The design of primers for PCR was based on the sequence of VR 2385. The sequences and locations of the primers, IM729 and IM782 for ORF 1b, IM312 and IM313 for ORF 2, XM1022 and IM258 for ORF 3, XM1024 and XM1023 for ORF 4, PP286 and PP287 for ORF 5, PP289 and XM780 for ORF 6, and PP284 and PP285 for ORF 7 and the 3' noncoding region (NCR), are shown in Table 4. The primers were designed in such a way that each set of primers will only amplify a fragment from a particular ORF, and the overlapping sequences between neighboring ORFs are not included in any given fragment. Therefore, each of these seven DNA fragments represents only one particular ORF except for fragment 7, which represents both ORF 7 and the 3'-NCR.

These seven DNA fragments were labeled with $^{32}$P-dCTP and hybridized to Northern blots of total intracellular RNAs extracted from cells infected with either of two U.S. isolates of PRRSV, ISU 1894 and ISU 79. Total intracellular RNAs isolated from mock-infected CRL 11171 cells were included as a control.

Figure 7A:
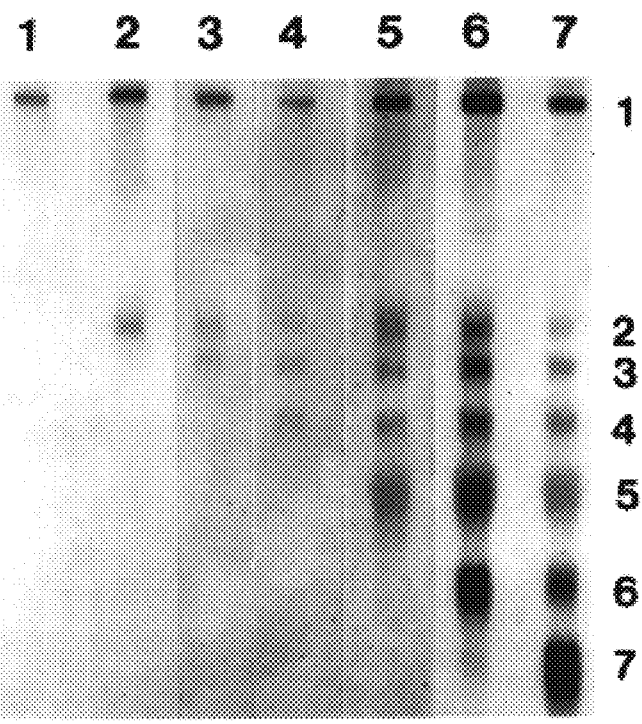
FIGS. 7A and 7B show a Northern blot analysis of total intracellular mRNAs isolated from CRL 11171 cells infected with ISU 1894 (A) and ISU 79 (B)
Figure 7B:
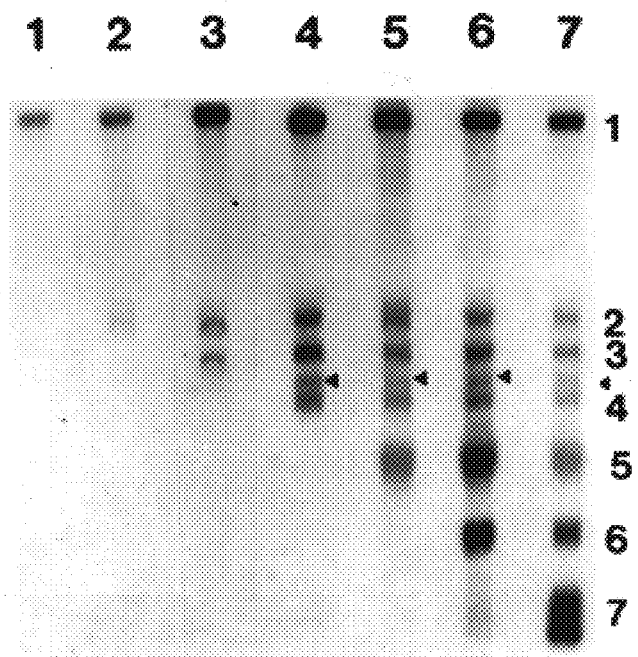

Northern blot analyses showed that Probe 1, generated from ORF 1b, hybridized only with the genomic RNA. Probes 2 through 7 each hybridized with one more additional RNA species besides the genomic RNA (FIG. 7). The results indicate that a 3'-coterminal nested set of six (ISU 1894) or more (ISU 79) sg mRNAs is formed in PRRSV-infected cells (FIGS. 7A and 7B), with the smallest 3'-terminal RNA (sg mRNA 7) encoding ORF 7. The sg mRNAs of U.S. PRRSV all contain the 3'-end of the genomic RNA, but extend for various distances towards the 5'-end of the genome, depending on the size of the given sg mRNA.

The sg mRNA 4-1 of PRRSV isolate ISU 79 hybridized with probes 4 through 7, but not with probes 1, 2 and 3 (FIG. 7B), suggesting that sg mRNA 4-1 contains ORFs 4 through 7 as well as the 3'-NCR. Therefore, sg mRNA 4-1 is generated from the sequence upstream of ORF 4.

A single nucleotide substitution leads to the acquisition of the additional species of sg mRNA 4-1. Northern blot hybridization data showed that sg mRNA 4-1 is derived from the sequence upstream of ORF 4 (FIG. 7B). To determine the exact location and the leader-mRNA junction sequence of sg mRNA 4-1, a set of primers, IM755 and DP586, was designed (Table 4). The forward primer IM755 was based on the 3'-end of the leader sequence of VR 2385, and the reverse primer DP586 is located in ORF 4 (Table 4).

RT-PCR with primers IM755 and DP586 was performed using total intracellular RNAs isolated from cells infected with either of ISU 1894 or ISU 79. ISU 79 produces sg mRNA 4-1, but ISU 1894 does not (FIG. 5). A 30-second PCR extension time was applied to preferentially amplify the short fragments representing the 5'-terminal sequences of sg mRNAs 3, 4 and 4-1.

Figures 8A, 8B:
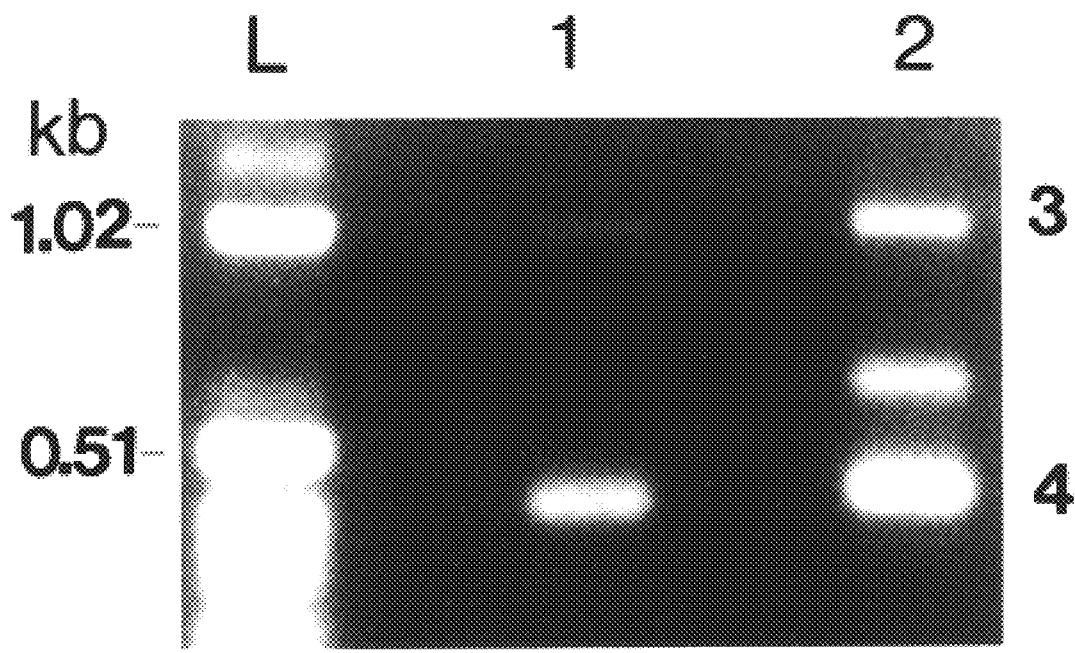
FIGS. 8A and 8B show RT-PCR amplification of the 5'-terminal sequences of the sg mRNAs 3 and 4 of ISU 1894 (lane 1) and sg mRNAs 3, 4 and 4-1 of ISU 79 (lane 2) (A) where lane L is a 1-kb marker; and the leader-mRNA junction sequences of sg mRNAs 3 and 4 of ISU 79 and ISU 1894 and of sg mRNA 4-1 of ISU 79 (B), where the locations of the leader-mRNA junction sequences in the genomes relative to the start codon of each ORF were indicated by minus (–) numbers of nucleotides upstream of the ORFs.
Figure 10A:
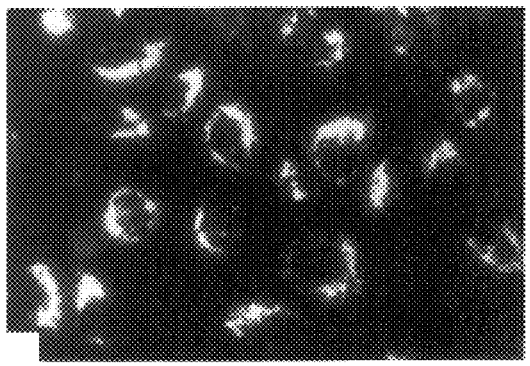
FIGS. 10A, 10B, 10C, 10D. Immunofluorescence assay of the MAbs with PRRSV-infected cells. Hybridoma supernatant was tested with IFA on infected ATCC CRL 11171 cells. Typical immunofluorescence from reaction with protein-specific MAbs is shown here. A. GP4-specific MAb, PP4bB3; B. E-specific MAb, PP5dB4; C. N-specific MAb, PP7eFl 1; and D. Negative control, PPAc8.
Figure 10B:
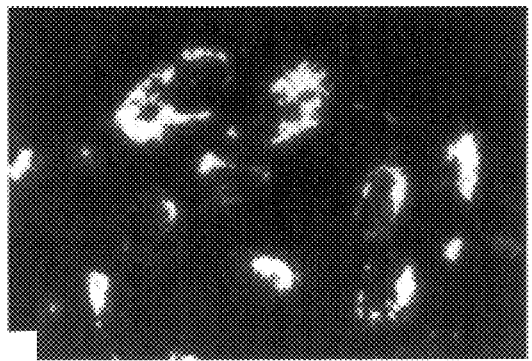
Figure 10C:
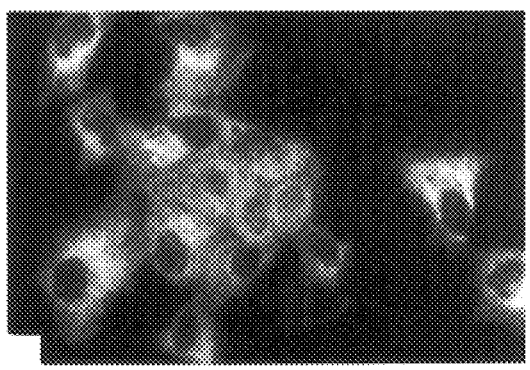
Figure 10D:
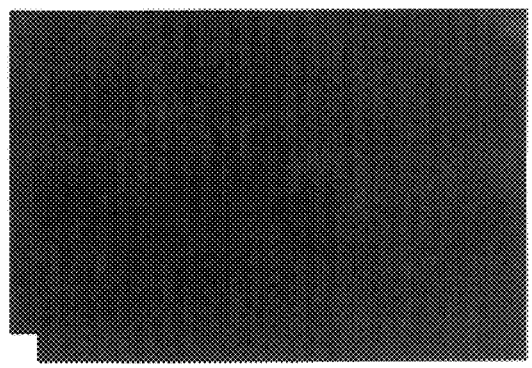

Analysis of the RT-PCR products showed that two fragments with sizes of about 1.1 kb and 0.45 kb were amplified from the total RNAs of ISU 1894 virus-infected cells (FIG. 8A). These two fragments represent 5'-portions of sg mRNAs 3 and 4, respectively. In addition to the two fragments observed in the isolate of ISU 1894, a third fragment of about 0.6 kb representing the 5'-portion of sg mRNA 4-1 was also amplified from total RNAs of cells infected with ISU 79 (FIG. 8A).

To determine the leader-mRNA junction sequences of sg mRNAs 3, 4 and 4-1, the RT-PCR products of ISU 79 and ISU 1894 were purified from an agarose gel using a GENECLEAN kit (Bio 101, Inc.), and sequenced directly with an automated DNA Sequencer (Applied Biosystems). The primers used for sequencing the 5'-end of the RT-PCR products (XM141 and XM077, Table 4) were designed on the basis of the genomic sequences of ISU 79 and ISU 1894 (FIG. 9). The leader-mRNA junction sequences (in which the leader joins the mRNA body during the synthesis of sg mRNAs) of sg mRNAs 3, 4, and 4-1 of the two U.S. PRRSV isolates were determined by comparing the sequences of the 5'-end of the sg mRNAs and the genomic RNA of the two isolates (FIG. 8B).

The leader-mRNA junction sequences of sg mRNAs 3 and 4 of ISU 1894 and ISU 79 were identical. For sg mRNA 3, the leader-junction sequence (GUAACC) is located 89 nucleotides upstream of ORF 3. For sg mRNA 4, UUCACC is located 10 nucleotides upstream of ORF 4 (FIG. 8B and FIG. 9). The leader-mRNA junction sequence of sg mRNA 4-1 of ISU 79 is UUGACC, located 236 nucleotides upstream of ORF 4 (FIGS. 8B and 9).

Sequence alignment of the genomic sequences of ISU 79 and ISU 1894 shows that a single nucleotide substitution, from T in ISU 1894 to C in ISU 79, leads to the acquisition of an additional leader-mRNA junction sequence, UUGACC, in ISU 79 (FIGS. 8B and 9). Therefore, an additional species of sg mRNA (4-1) is formed (FIG. 5). In addition to ORFs 4 to 7 contained within sg mRNA 4, sg mRNA 4-1 contains at the 5'-end an additional small ORF (ORF 4-1) with a coding capacity of 45 amino acids (FIG. 9). This small ORF stops just one nucleotide before the start codon of ORF 4.

Sequence analyses of ORFs 2 to 7 of two U.S. isolates reveal heterogeneity of the leader mRNA junction sequences. ORFs 2 to 5 of ISU 79 and ISU 1894 were cloned and sequenced (see Experiment 1 above). ISU 79 produces seven easily distinguishable sg mRNAs, whereas ISU 1894 produces six distinguishable sg mRNAs (FIGS. 5 and 7). At least three cDNA clones at any given region of ORFs 2 to 5 were sequenced for each virus isolate, using universal and reverse primers as well as virus-specific primers XM969, XM970, XM1006, XM078, and XM077 (Table 4). The sequences of ORFs 6 and 7 of ISU 1894 and ISU 79 are disclosed in U.S. application Ser. No. 08/301,435.

Sequence analysis showed that the ORFs 2 to 7 of ISU 79 and ISU 1894 overlap each other except for a 10-nucleotide noncoding region between ORF 4 and ORF 5. The same observation was previously made for VR 2385 (U.S. application Ser. No. 08/301,435). This is very unusual, since all members of the proposed Arteriviridae family, including LV, contain overlapping ORFs. However, the ORFs of coronaviruses are separated by intergenic noncoding sequences. Therefore, U.S. PRRSV appears to be somewhat similar to the coronaviruses in terms of the genomic organization in junction regions of ORFs 4 and 5.

ORF 2 of ISU 1894 was one amino acid longer than that of ISU 79 (FIG. 9). The stop codon of ORF 2, TAG, was changed to TGG in ISU 1894 immediately followed by a new stop codon (TGA) in ISU 1894 (FIG. 9). The sizes of other ORFs of ISU 79 and ISU 1894 were identical (FIG. 9). There were no deletions or insertions in ORFs 2 to 7 of these isolates. However, numerous substitutions are present throughout the entire sequence of ORFs 2 to 7 between ISU 79 and ISU 1894 (FIG. 9).

The numbers and locations of the determined or predicted leader-mRNA junction sequences varied between ISU 1894 and ISU 79 (FIG. 9). In addition to the regular leader-mRNA 4 junction sequence, TTCACC, 10 nucleotides upstream of ORF 4, there was an additional leader-mRNA 4-1 junction sequence (TTGACC) located 236 nucleotides upstream of ORF 4 in ISU 79 (FIG. 9). The leader-mRNA junction sequences of sg mRNAs 4 and 4-1 were separated by 226 nucleotides, which correlated with the estimated sizes of sg mRNAs 4 and 4-1 observed in Northern blot analysis (FIG. 5) and RT-PCR amplification (FIG. 8A).

The leader-mRNA 3 junction sequence is identical between ISU 1894 and ISU 79, GTAACC, located 89 nucleotides upstream of ORF 3. The predicted leader-mRNA junction sequences of sg mRNAs 2 and 6 of ISU 1894 and ISU 79 were also the same (FIG. 9).

However, the predicted leader-mRNA 5 junction sequences of ISU 1894 and ISU 79 are different (FIG. 9). There are 3 potential leader-mRNA 5 junction sequences for ISU 79 (GCAACC, GAGACC and TCGACC, located 55, 70 and 105 nucleotides upstream of ORF 5, respectively). Two potential leader-mRNA 5 junction sequences were also found in ISU 1894 (GAAACC and TCGACC, located 70 and 105 nucleotides upstream of ORF 5, respectively) (FIG. 9). The differences were due to the two-nucleotide substitutions in the predicted leader-mRNA 5 junction sequences of these isolates (FIG. 9).

In addition to the leader-mRNA 7 junction sequence 15 nucleotides upstream of ORF 7, an additional leader-mRNA 7 junction sequence was found (ATAACC), located 129 nucleotides upstream of ORF 7 in each of these two isolates (FIG. 9). However, the sg mRNA corresponding to this additional leader-mRNA 7 junction sequence was not clearly distinguishable from the abundant sg mRNA 7 which produced a widely-diffused band in the Northern blot (FIGS. 5, 6 and 7).

Variations in the numbers and locations of the leader-mRNA junction sequences between LV and the two U.S. isolates analyzed in this experiment were also found by comparing the leader-mRNA junction sequences of LV with those of the two U.S. isolates ISU 1894 and ISU 79. Taken together, these data indicate that the sg mRNAs of PRRSV are polymorphic, and the numbers and the exact sizes of the sg mRNAs depend on the particular PRRSV isolate analyzed. However, a nested set of six sg mRNAs most likely reflects the standard arterivirus genome organization and transcription.

TABLE 4

Synthetic oligonucleotides used in Experiment 2

| Oligo Name | Sequence | | Location (nucleotides)[a] | Polarity[b] |
|---|---|---|---|---|
| IM729 | 5'-GACTGATGGTCTGGAAAG-3' | (SEQ ID NO:78) | ORF1b, −507 to −490 upstream of ORF2 | + |
| IM782 | 5'-CTGTATCCGATTCAAACC-3' | (SEQ ID NO:79) | ORF1b, −180 to −163 upstream of ORF2 | − |
| IM312 | 5'-AGGTTGGCTGGTGGTCTT-3' | (SEQ ID NO:80) | ORF2, 131 to 148 downstream of ORF2 | + |
| IM313 | 5'-TCGCTCACTACCTGTTTC-3' | (SEQ ID NO:81) | ORF2, 381 to 398 downstream of ORF2 | − |
| XM1022 | 5'-TGTGCCCGCCTTGCCTCA-3' | (SEQ ID NO:82) | ORF3, 168 to 175 downstream of ORF3 | + |
| IM268 | 5'-AAACCAATTGCCCCCGTC-3' | (SEQ ID NO:83) | ORF3, 520 to 537 downstream of ORF3 | − |
| XM1024 | 5'-TATATCACTGTCACAGCC-3' | (SEQ ID NO:84) | ORF4, 232 to 249 downstream of ORF4 | + |
| XM1023 | 5'-CAAATTGCCAACAGAATG-3' | (SEQ ID NO:85) | ORF4, 519 to 536 downstream of ORF4 | − |
| PP287 | 5'-CAACTTGACGCTATGTGAGC-3' | (SEQ ID NO:86) | ORF5, 129 tO 148 downstream of ORF5 | + |
| PP286 | 5'-GCCGCGGAACCATCAAGCAC-3' | (SEQ ID NO:87) | ORF5, 538 to 667 downstream of ORF5 | − |
| PP289 | 5'-GACTGCTAGGGCTTCTGCAC-3' | (SEQ ID NO:88) | ORF6, 119 to 138 downstream of ORF6 | + |
| XM780 | 5'-CGTTGACCGTAGTGGAGC-3' | (SEQ ID NO:89) | ORF6, 416 to 433 downstream of ORF6 | − |
| PP285 | 5'-CCCCATTTCCCTCTAGCGACTG-3' | (SEQ ID NO:90) | ORF7, 157 to 178 downstream of ORF7 | + |
| PP284 | 5'-CGGCCGTGTGGTTCTCGCCAAT-3' | (SEQ ID NO:91) | 3'-NCR, −27 to −6 upstream of poly (A) | − |
| JM260 | 5'-GGGGAATTCGGGATAGGGAATGTG-3' | (SEQ ID NO:69) | ORF3, 338 to 356 downstream of ORF3 | + |
| JM259 | 5'-GGGGATCCTTTTGTGGAGCCGT-3' | (SEQ ID NO:68) | ORF6, 34 to 52 downstream of ORF6 | − |
| XM993 | 5'-GGTGAATTCGTTTTATTTCCCTCCGGG-3' | (SEQ ID NO:72) | ORF1b, −53 tO −35 upstream of ORF2 | + |
| XM992 | 5'-GGGGGATCCTGTTGGTAATAG/AGTCTG-3' | (SEQ ID NO:70—71) | ORF3, −50 to −34 upstream of ORF4 | − |
| XM970 | 5'-GGTTTCACCTAGAATGGC-3' | (SEQ ID NO:74) | ORF2, 522 to 550 downstream of ORF2 | + |
| XM969 | 5'-GATAGAGTCTGCCCTTAG-3' | (SEQ ID NO:73) | ORF5, 443 to 460 downstream of ORF6 | − |
| XM1006 | 5'-GCTTCTGAGATGAGTGA-3' | (SEQ ID NO:75) | ORF4, 316 tO 332 downstream of ORF4 | + |
| XM078 | 5'-CTGAGCAATTACAGAAG-3' | (SEQ ID NO:76) | ORF2, 202 tO 218 downstream of ORF2 | + |
| XM077 | 5'-CAACCAGGCGTAAACACT-3' | (SEQ ID NO:95) | ORF3, 316 to 333 downstream of ORF3 | − |
| IM755 | 5'-GACTGCTTTACGGTCTCTC-3' | (SEQ ID NO:92) | Leader, 3' end of the Leader sequence | + |
| DP586 | 5'-GATGCCTGACACATTGCC-3' | (SEQ ID NO:93) | ORF4, 355 to 372 downstream of ORF4 | − |
| XM141 | 5'-CTGCAAGACTCGAACTGAA-3' | (SEQ ID NO:94) | ORF4 78 to 97 downstream of ORF4 | − |

[a]The oligonucleotides were designed on the basis of sequence data presented in this application and U.S. application Ser. Nos. 08/131,625 and 08/301,435
[b]Oligonucleotides complementary to the genomic RNA have negative (-) polarities.

EXAMPLE 3

Cell line ATCC CRL 11171 was used for the propagation of PRRSV isolates. The maintenance of the cell line and isolation of virus were the same as previously described (Meng et al., *J. Gen. Virol.* 75:1795–1801 (1994); Meng et al., *J. of Veterinary Diagnostic Investigation* 8:374–381 (1996). Plasmacytoma cell line SP2/O was used for cell fusion in MAb preparation. PRRSV ATCC VR 2385 was used as antigen for screening of hybridomas secreting PRRSV specific monoclonal antibodies.

Indirect Immunofluorescence Assay (IFA). Monolayers of ATCC CRL 11171 cells were inoculated with PRRSV VR 2385 at 0.1 multiplicities of infection, incubated for 48 hrs and fixed with methanol. Hybridoma supernatant was incubated on the fixed-cell monolayer at 37° C. for 30 min. Fluorescein-labeled goat anti-mouse IgG (H+L) conjugate was used to detect the specific reaction. One PRRSV N (ORF 7 products) specific monoclonal antibody, PP7eF11 was used as a positive control and cell culture supernatant from a non-PRRSV specific MAb, PPAc8 was used as a negative control.

MAb preparation. The whole cell lysates from insect cells infected with recombinant baculoviruses of PRRSV ORFs 4 and 5 were used as immunogen to immunize mice. Construction of the recombinant baculoviruses containing the PRRSV ORFs 4 and 5 was done with the strategies as previously described (Bream et al. *J. Virol.* 67:2665–2663 (1993)). Briefly, PRRSV ORFs 4 and 5 genes were PCR amplified separately from the template of pPSP.PRRSV2-7 plasmid (Morozov et al., *Archives of Virology* 140:1313–1319 (1995)) with primers containing restriction sites of BamHI and EcoRI. The amplified fragments were cut with the restriction enzymes indicated above and ligated into the vector PVL1393 (Invitrogen). The inserted genes were under control of the polyhedrin gene promotor (O'Reilly et al., *Baculovirus Expression Vectors: A Laboratory Manual*, pages 107–234, $2^{nd}$ Edition, New York: W. H. Freeman and Company (1992)) and verified with restriction enzyme digestion and PCR amplification. Then the recombinant vector DNA and linearized Autographa California multinuclear polyhedrosis virus DNA (Invitrogen) were co-transfected into Sf9 cells as described in the instruction manual. The inserted genes in the recombinant baculoviruses were verified with hybridization and PCR amplification (O'Reilly et al., 1992). The recombinant viruses were used to inoculate insect cells and the cell lysate was used for immunization of mice. The immunization was carried out with 3 to 5 times of intraperitoneal injections at two weeks interval. Spleenocytes were hybridized with SP2/O myeloma cells as previously described (Brown & Ling, "Murine Moncolonal Antibodies," In *Antibodies: a practical approach*, pp. 81–104, Edited by Catty D. Zoxford, Washing, D.C. IRL Press (1988)). Hybridomas were screened for secreting PRRSV specific antibodies with IFA to detect reaction with PRRSV ATCC VR 2385. Positive hybridomas were selected and cloned three times. Four MAbs were developed to the GP4 and six Mabs to the protein. Mabs were isotyped with MonoAb ID kits (Zymed Laboratories Inc).

Enzyme-linked immunosorbent assay (ELISA). ELISA has been well described (Harlow & Lane, *Antibodies: A laboratory manual*, pp. 471–612, Cold Spring Harbor Laboratory New York (1988); Ausubel et al., *Short protocols in molecular biology*, pp. 11.5–11.7, $2^{nd}$ Edition, New York, Greene Publishing Associates and John Wiley & Sons (1992)). Coating antigens were extracted with 1% Triton X-100 from PRRSV VR 2385-infected cells. MAbs were tested for binding activity in ELISA with the antigens binding to plates. Extract from normal cells and cell culture medium from the non-PRRSV specific MAb, PPAc8 were included as a negative antigen and a negative antibody controls respectively. The PRRSV N-specific MAb, PP7eF11 was used as a positive control. Specific reactions were detected with goat anti-mouse IgG (H+L) peroxidase conjugate and revealed with substrate 2,2'-azino-bis(3-ethylbenzthiazoline-6-sulfonic acid) (ABTS). Then the optical density was measured at 405 nm ($A_{405}$).

Fixed-cell ELISA was conducted as previously reported (van Nieuwstadt et al.,*J. Virol.* 70:4767–4772 (1991)) to test the reactivity of MAbs with PRRSV field isolates. Briefly, monolayers of ATCC CRL 11171 cells were inoculated with PRRSV field isolates at 0.001 multiplicities of infection, incubated for 48 hrs and fixed with methanol. Then the cells were blocked with 1% BSA for 1 hour at room temperature. Cell culture supernatant of MAbs were diluted in two-fold series and added to the fixed-cell plates. The PP7eF11 and PPAc8 were used as positive and negative controls respectively. Specific reactions were detected as described above.

Immunoblotting. Western immunoblot analyses were carried out as described previously (Harlow & Lane, *Antibodies:A laboratory manual*, pp. 471–612, Cold Spring Harbor Laboratory, New York (1988)). Protein samples were treated under different conditions before separated in gel. For denaturing conditions samples were treated at 100° C. for 3 minutes in Laemmli sample buffer containing 2% SDS and 5% 2-mercaptoethanol and run in SDS-PAGE. Under non-denaturing conditions, samples were treated at 40° C. for 20 min in sample buffer containing 1% triton X-100 and run in PAGE. Then separated proteins were transferred to nitrocellulose membrane by electrophoresis. The nitrocellulose membrane was blocked with 3% BSA. MAbs were screened for the reactivity with the antigens on the membrane with multi-screening apparatus. Pig anti-PRRSV serum was used as a positive control and cell culture supernatant from PPAc8 as a negative control. Bound antibodies were detected by incubation with goat anti-mouse IgG+IgA+IgM peroxidase conjugate or goat anti-pig IgG peroxidase conjugate followed by color development in 4-chloro-1-naphthol substrate.

Virus neutralization (VN) test. Virus neutralizing activity of MAbs was tested as described previously (Mecham et al., *Viral Immunol.* 3:161–170 (1990) & White et al., *J. Gen. Virol.* 71:4767–4772 (1990)) with some modifications. Hybridoma supernatant was mixed with the same volume of PRRSV dilution containing 30–70 plaque forming units, which was diluted with DMEM containing 10% guinea pig complement. The virus-antibody mixture was incubated at 37° C. for 1 hr, and then transferred to the monolayer of ATCC CRL 11171 cells in six-well plate for 1 more hr incubation at 37° C. Then an agarose-medium mixture overlaid the monolayer. After 3-day incubation at 37° C., the monolayer was stained with 0.05% neutral red in agarose. Pig anti-PRRSV serum was used as a positive control and hybridoma cell culture medium from a non-PRRSV specific MAb was included as a negative control.

PRRSV specific Mabs identified with IFA. Hybridomas were screened with IFA on PRRSV VR 2385-infected ATCC CRL 11171 cells. IFA positive hybridomas were selected, amplified and cloned. Six MAbs were developed against PRRSV E protein and four to the GP4. All of them showed strong perinuclear fluorescence with a little difference in intensity, which was different from the cytoplasmic staining of PRRSV N protein specific MAb (FIG. 10). This result indicated that the GP4 and E glycoproteins were synthesized and accumulated in subcellular compartments in PRRSV-infected cells as transferring of oligosaccharides to a glycoprotein is generally processed in a particular compartment such as the endoplasmic reticulum and the Golgi complex (Pfeffer et al., *Ann. Rev. Biochem.* 56:829–852 (1987)). GP4 and E were predicted as membrane-associated glycoproteins (Meng et al., 1994 & Morozov et al., *Archives of Virology* 140:1313–1319 (1995)). In contrast, the PRRSV N protein is highly basic and hydrophilic, and is synthesized in the cytoplasm of PRRSV-infected cells, which was shown by the observation of cytosol distribution of fluorescence in IFA with N-specific MAb staining. All the MAbs were identified as subtype IgM.

Figure 11:
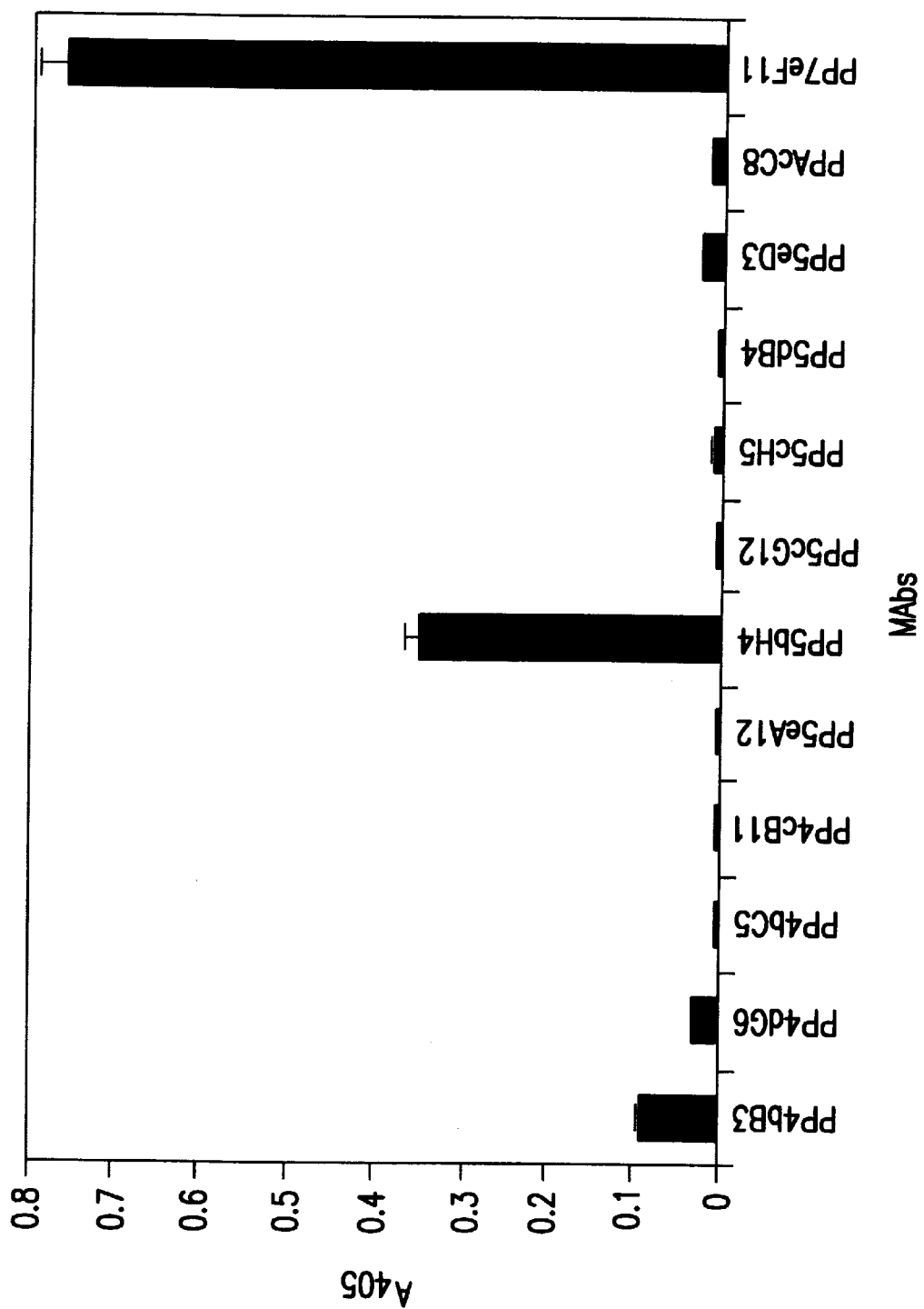
FIG. 11. Reactivity of the MAbs and detergent extracted PRRSV antigen in ELISA. Plates were coated with antigen extracted from PRRSV-infected cells with detergent 1% Triton X-100 and blocked with 1% BSA. Hybridoma supernatant was tested along with positive and negative controls, PP7eFl 1 and PPACS respectively. Specific reactions were detected with anti-mouse IgG peroxidase conjugate. ABTS substrate was incubated in the plates for 20 min before A405 was measured. The first four MAbs starting from PP4bB3 are GP4-specific antibodies, and the next six MAbs starting from PP5bH4 are E-specific antibodies.

Reactivity with PRRSV antigen in ELISA. In order to determine the sensitivity of the epitopes to detergent treatment, ELISAs were run to test the reactivity of the MAbs with 1% Triton X-100 extracted PRRSV antigen. Among the MAbs to the E protein, only PP5bH4 showed strong reactivity to the PRRSV antigen (FIG. 11). No clear reaction was detected between the rest of the E-specific MAbs and the PRRSV antigen. Among the MAbs to the GP4, only PP4bB3 showed a mild reactivity with the PRRSV antigen. The other three of the MAbs to GP4 failed to show any reactivity. The negative controls did not show reaction in ELISA.

Out of the 10 MAbs, only PP5bH4 and PP4bB3 showed reactivity in the ELISA with detergent extracted PRRSV antigen. This result indicated that the epitope recognized by PP5bH4 was resistant to Triton X-100 treatment and the epitope of PP4bB3 was partially resistant to the detergent. The epitopes recognized by the other 8 MAbs were sensitive to the treatment, and may be conformationally dependent. Triton X-100 is generally selected to disrupt cell membranes for its nondenaturing property (Deutscher, "Guide to protein purification," *Methods in Enzymology*, Vol. 182, San Diego, Calif., Academic Press, Inc. (1990)), but in this test the epitopes in the PRRSV proteins were somehow altered during the extraction process as monitored by the MAb binding.

Figure 12:
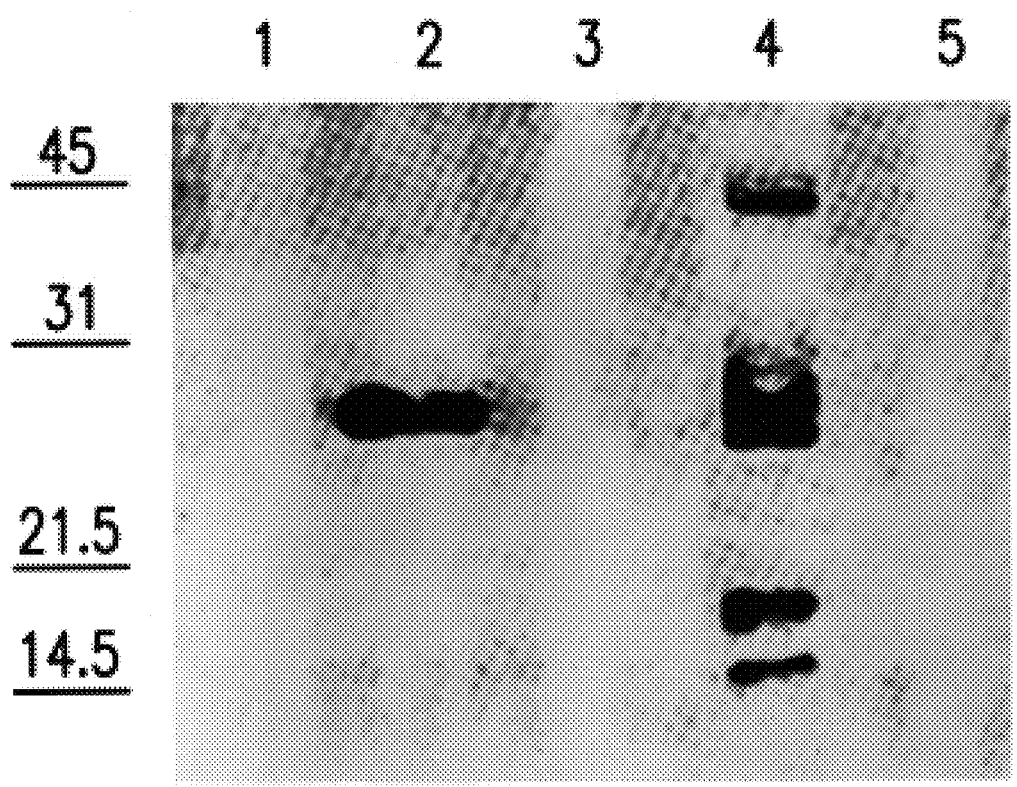
FIG. 12. Reactivity of the E specific MAbs and extract of PRRSV virions in Immunoblotting. MW standards (in kDa) are indicated on the left side of the figure. Lanes: 1, PP5dB4; 2, PP5bH4; 3, Negative control: PPAc8; 4, Positive control: pig anti-PRRSV serum; 5, Negative control: normal pig serum.
Figure 14:
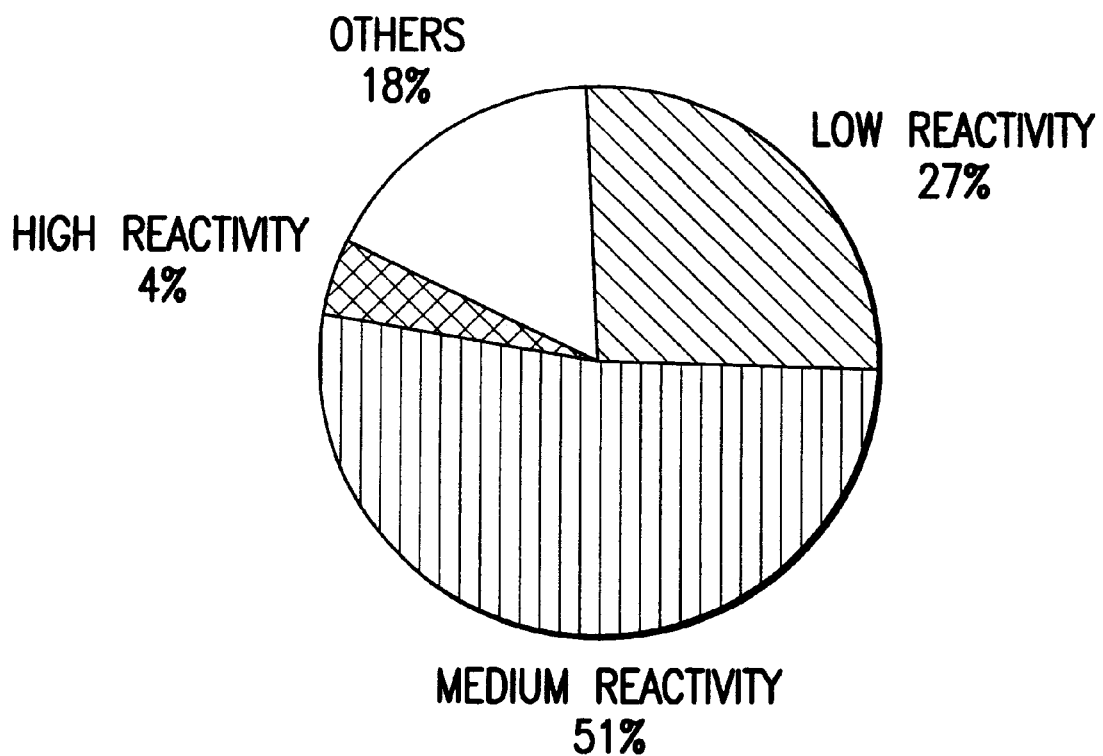
FIG. 14. Reactivity pattern of PRRSSV isolates with the MAbs to PRRSV. Titers of the MAbs were shown in FIG. 13. The reactivity pattern was determined according to the titers of at least 6 MAbs with any one isolate:<=32—low reactivity; 64 to 128—medium reactivity; >=256—high reactivity. Those isolates not belonging to the groups above were grouped as other. Total isolates tested were 23.

Immunoblotting assay. Western-blotting was carried out to determine the reactivity of the MAbs with PRRSV antigen to confirm the speculation that the MAbs were against conformationally dependent epitopes. Under denatured conditions in SDS-PAGE, only the PP5bH4 recognized a band of purified PRRSV virions in the position of 26 kDa which corresponded with the putative E detected with pig anti-PRRSV serum (FIG. 12). Then immunoblotting was carried out with non-denatured PAGE to test if the epitopes were preserved under nondenaturing conditions. Among the six MAbs to E, only PP5bH4 showed reaction with the PRRSV antigen. Of the MAbs to GP4, none recognized the PRRSV antigen in purified virions or in infected cells under either conditions in this test (result not shown).

The MAbs except PP5bH4 failed to recognize the PRRSV antigen in immunoblot, which indicated that the epitopes recognized by these MAbs were not derived from continuous structure. MAb PP5bH4 reacted with PRRSV in the position of 26 kDa, which confirmed the report about the molecular mass of E (Meulenberg et al., *Virology* 192:62–72 (1995)). This result showed that the epitopes recognized by the other 9 MAbs were sensitive to detergent treatment and corresponded to that of ELISA. Again the result indicated that the epitopes were conformationally dependent. PP4bB3 failed to show any reaction with PRRSV antigen in Western-blot, which could be due to the epitope loss or alternation during PAGE and transfer. The sample of purified PRRSV showed three bands with molecular mass of about 19, 26–31 and 45 kDa (FIG. 12). The missing 15 kDa band of N protein could not be explained.

Virus neutralizing activity. Plaque-reduction assay was run to test whether there was any virus neutralizing activity among the MAbs to the E and GP4 proteins. Only one E-specific MAb, PP5dB4 showed the ability of homologous neutralization to the VR 2385 isolate. All the other MAbs failed to show any neutralizing activity to this isolate. The positive control, pig anti-PRRSV serum also showed virus neutralizing activity.

Among the ten MAbs to GP4 and E, at least PP5dB4 showed homologous virus neutralizing activity against PRRSV VR 2385. The neutralizing epitope was conformationally dependent as PP5dB4 failed to recognize PRRSV antigen in ELISA and in Western-blot. Also the neutralizing activity of PP5dB4 indicates that at least part of the epitope is located on the virion surface and accessible by the MAb. The mechanism of neutralizing activity of PP5dB4 is not clear. It could be due to blocking of the virus binding or entry into the cells.

Reactivity with other PRRSV isolates. PRRSV field isolates were propagated to test the cross-reactivity of the MAbs in fixed-cell ELISA and to determine the epitope presence in other PRRSV isolates (Table 5). Fixed-cell ELISA was used because most of these MAbs recognized conformationally dependent epitopes and these epitopes could be preserved in fixed cells. All the MAbs react with all the isolates but with different titers. The result indicates that the epitopes recognized by the MAbs were conserved among the isolates tested. However, there were antigenic differences among the isolates tested. Reactivity intensity was arbitrarily defined as high if titers were greater than or equal to 256, as medium if titers were 64 to 128, and as low if titers were smaller than or equal to 32. Out of the 23 isolates tested, only PRRSV VR 2385 had high reactivity with 7 of the 10 MAbs. Five isolates had low reactivity with at least 6 of the 10 MAbs, 12 isolates had medium reactivity with at least 6 of the 10 MAbs and the other 5 isolates had low reactivity with half of the MAbs. The MAb PP4dG6 and PP5bH4 showed lower reactivity with most of the isolates than other MAbs. The PP4bB3 showed the strongest reactivity among all the MAbs against GP4 and E proteins. The titer difference was as high as 64-fold for the reaction of one MAb with the different isolates, such as the titers of MAb PP4cBl 1 reacting with PRRSV RP 10 and RP 12, 16 and 1024 respectively. On the other hand, the titer difference of MAbs with one isolate was as high as 128-fold, such as the titers of MAbs PP4bB3 and PP4bC5 reacting with PRRSV RP11, 1024 and 8 respectively. This result indicated that the epitopes recognized by the different MAbs were different. The positive MAb control show strong reactivity with all the isolates except the ISU-51. The reactivity difference of MAbs with PRRSV isolates was consistent with the report that the amino acid sequence identity of VR 2385, ISU22, ISU55 and RP45 was 94–98% in ORF 4 and 88–97% in ORF 5 (Meng et al., *J. Gen. Virol.* 140:745–755 (1995)).

In summary, six MAbs were developed to the PRRSV E protein and four to the GP4. All of them except PP5bH4 were against conformationally dependent epitopes as determined by ELISA and immunoblotting. MAb PP5dB4 showed virus neutralizing activity against VR 2385. Reactivity pattern of the MAbs with PRRSV field isolates indicated that there are antigenic difference in PRRSV GP4 and E, which confirmed previous reports on MAbs against PRRSV N and ORF 3 product (Nelson et al., *J. Clinical Microbiology* 31:3184–3189 (1993); Drew et al., *J. General Virol.* 76:1361–1369 (1995); Wieczorek-Krohmer et al., *Veterinary Microbiology* 51:257–266 (1996)).

EXAMPLE 4

Cells and viruses. ATCC CRL11171 cells were used to propagate PRRSV and PRRSV purification was done as previously described (Meng et al., *J. Gen. Virol.,* 75:1795–1801 (1994); Meng et al., *J. Vet. Diag. Invest.* 8:374–381 (1996); Halbur et al. *Vet. Pathol.* 32:648–660, (1995). PRRSV isolate ATCC VR 2385 (Meng et al., 1994 & Morozov et al., 1995) was used for PCR amplification of ORFs 2 to 4 genes.

*Spodoptera frugiperda* clone 9 (Sf9) and High Five™ (Invitrogen) insect cells were cultured for propagation of baculovirus. The baculovirus strain Autographa California multinuclear polyhedrosis virus (AcMNPV) was used as parent virus for recombinant baculovirus construction.

Construction of AcMNPV recombinant transfer vector. Construction of the baculovirus transfer vectors containing the PRRSV ORFs 2, 3 and 4 separately was done with the strategies as previously described (Bream et al., *J. Virol.* 67:2655–2663(1993). Briefly, PRRSV ORFs 2 to 4 genes were PCR amplified separately from the template of pPSP.PRRSV2-7 plasmid with primers containing restriction sites of BamHI and Pst I for genes of ORFs 2 and 3, BamHI and EcoRI for ORF 4.

The forward primer for ORF 2 was 5'GCACGG ATC-CGAATTAACATGAAATGGGGT3' (SEQ ID NO: 96) and the reverse primer was 5'CCACCT GCAGATTCACCGT-GAGTTCGAAAG3' (SEQ ID NO 97). The forward primer for ORF 3 was 5'CGTCGGATCCTCCTACAATGGCTAAT-AGCT3' (SEQ ID NO: 105) and the reverse primer was 5'CGCGCTGCAGTGTCCCTATCGACGTGCGGC3' (SEQ ID NO: 106). The forward primer for ORF 4 was 5'GTATG-GATCCGCAATTGGTTTCACCTATAA3' (SEQ ID NO: 107) and the reverse primer was 5'ATAGGAATTCAACAA-GACGGCACGATACAC3' (SEQ ID NO: 108). The amplified fragments were cut with restriction enzymes as indicated above and ligated into the vector pFastBAC1 (GIBCO BRL) for ORFs 2 and 3 fragments, and the vector PVL1393 (Invitrogen) for ORF 4 fragment. The inserted genes were under control of the polyhedrin gene promotor (O'Reilly et al., Baculovirus Expression Vectors: A Laboratory Manual, W. H. Freeman & Co., New York (1992) and verified with restriction enzyme digestion and PCR amplification. Then the recombinant vectors containing the ORFs 2 to 4 genes separately were isolated and designated as pPSP.Ac-p2 for ORF 2 transfer vector, pPSP.Ac-p3 for ORF 3 transfer vector and pPSP.Ac-p4 for ORF 4 transfer vector. For pPSP.Ac-p2 and pPSP.Ac-p3, their DNA were isolated and transfected into competent DH10BAC E. Coli cells (GIBCO BRL) containing the whole genome of baculovirus called Bacmid.

Transfection and selection of recombinant viruses. For ORFs 2 and 3, recombinant viruses were generated with the BAC-TO-BAC™ expression system (GIBCO BRL). The isolated recombinant Bacmid DNA were transfected into Sf9 insect cells and then the cell culture medium was collected as virus stock. For ORF 4 recombinant virus construction, pPSP.Ac-p4 DNA and linearized AcMNPV DNA (Invitrogen) were co-transfected into Sf9 cells as described in the instruction manual. Putative recombinant baculoviruses were selected following three rounds of occlusion body-negative plaque purification. The inserted genes in the recombinant viruses were verified with hybridization and PCR amplification (O'Reilly et al., 1992). Four recombinants were selected for each of the 3 strains of recombinant baculoviruses. Indirect immunofluorescence assays with pig anti-PRRSV serum showed that the four recombinants for each strain had similar level of protein expression. One was chosen from each strain for further study and designated as vAc-P2 for recombinant virus of ORF 2, vAc-P3 for that of ORF 3, and vAc-P4 for that of ORF 4.

Indirect Immunofluorescence Assay (IFA). IFA was well described elsewhere (O'Reilly et al., 1992). Briefly, Monolayer of High Five™ cells were infected with wild type (wt) AcMNPV or recombinant viruses of vAc-P2, vAc-P3 and vAc-P4 respectively at a multiplicity of infection of 0.1 and incubated for 72 hrs. Pig anti-PRRSV serum was used to detect specific proteins expressed in insect calls. Total protein expression was detected in the infected cells fixed, stained and observed under fluorescence microscope. Cell surface expression was detected on unfixed and unpermeabilized cells incubated with pig anti-PRRSV serum for 1 hr at 4° C., stained with fluorescein-labeled goat anti-pig IgG conjugate for 1 hr at 4° C., and then observed under fluorescence microscope.

Immunoblotting. Western immunoblotting was conducted as previously described (Harlow & Lane, Antibodies: A Laboratory Manual, Cold Spring Harbor Laboratory (1988)). Cell extract from insect cells infected with recombinant viruses or wt AcMNPV were used for this analysis. The proteins were separated with SDS-PAGE and transferred to nitrocellulose membrane by electrophoresis. The membrane was incubated with pig anti-PRRSV serum for 1 hour at room temperature. Specific reactions were detected with goat anti-pig IgG peroxidase conjugate, followed by color development in 4-chloro-1-naphthol substrate.

Tunicamycin treatment. High Five™ cells were infected with vAc-P2, vAc-P3, vAc-P4 or wt AcMNPV and incubated with 5 $\mu$g/ml tunicamycin in cell-culture medium from 0 to 72 hrs post infection. Non-treated insect cells were infected at the same time as controls. Cell lysate was harvested for SDS-PAGE and immunoblotting (O'Reilly et al., 1992).

Immunogenecity of the recombinant proteins. Cell lysates of insect cells infected with vAc-P2, vAc-P3 and vAc-P4 were used to test the recombinant protein's immunogenecity in rabbits. Two twelve-week old rabbits were injected intramuscularly and subcutaneously for each of these recombinant proteins. Blood was collected 10 days after two booster injections. Antibodies were tested with indirect ELISA (Ausubel et al., Short Protocols in Molecular Biology, pp. 11.5–11.7, 2$^{nd}$ Edition, New York Green Publishing Associates and John Wiley and Sons (1992)). Purified PRRSV virions were sonicated and used to coat 96-well plates and goat anti-rabbit IgG peroxidase conjugate was used to detect anti-PRRSV antibodies in rabbit serum samples. Preimmune rabbit serum was used as negative control. Substrate 2,2'-azino-bis(3ethylbenzthiazoline-6-sulfonic acid) (ABTS) was used to reveal specific reactions.

Results

Construction and verification of recombinant viruses. Details of construction strategy are mentioned under Methods. For ORFs 2 and 3, the recombinant baculoviruses were selected from *E. coli* containing the recombinant Bacmid and then collected from transfection of Sf9 insect cells. The recombinant viruses were further confirmed by DNA hybridization and PCR amplification. Both hybridization of DNA from infected cells with specific probes from the PRRSV genes of ORFs 2 to 4 and PCR amplification showed that the recombinant baculoviruses had the right genes cloned (data not shown).

Surface immunofluorescence of recombinant viruses vAc-P2, vAc-P3 and vAc-P4. High Five™ cells were infected with vAc-P2, vAc-P3, vAc-P3, vAc-P4, or wt AcMNPV, incubated for 72 hrs, and fixed with methanol for examination of total protein expression by IFA with pig anti-PRRSV serum. Unfixed and unpermeabilized insect cells were stained at 4° C. to detect cell surface immunofluorescence by IFA. There was weak cytoplasmic fluorescence in vAc-P2 infected cells, intense cytoplasmic fluorescence in vAc-P3 or vAc-P4 infected insect cells and no specific fluorescence in wt AcMNPV infected cells (FIG. 13). There was clear cell surface immunofluorescence in vAc-P2, vAc-P3 and vAc-P4 infected insect cells stained at 4° C. without fixation and permeabilization (FIG. 14). No cell surface staining was detected in wt AcMNPV infected insect cells. Also, recombinant virus infected insect cells in the absence of antibody did not show any fluorescence (data not shown).

Analysis of expressed recombinant proteins. Monolayer of High Five™ cells was infected at a multiplicity of infection of 0.1 with vAc-P2, vAc-P3, vAc-P4, or wt AcMNPV and incubated for 72 hrs. Expression of the recombinant proteins in insect cells was analyzed with whole cell extracts. Total protein samples were run on SDS-PAGE, transferred to nitrocellulose membrane by western-blotting and detected with pig anti-PRRSV serum. Purified PRRS virions were added and analyzed in the same gel. The ORF 2 product expressed in insect cells was detected as 27 and 29 kDa bands in $M_r$. The ORF 3 product was detected as 22, 25, 27–31 and 35–43 kDa multi-band species. The signals in $M_r$ of 27–31 and 35–43 kDa were hard to differentiate into single bands and may be due to differential glycosylation or partial proteolysis. The ORF 4 product was found as 15, 18, 22, 24, 28 and 30 kDa multi-band species. These specific bands were not detected in wt AcMNPV infected insect cells. There were at least four bands in purified PRRSV sample: 15, 19, 27–31 and 45 kDa in $M_r$. The specific bands detected in purified PRRS virions were not observed in normal cell control (FIG. 15).

The recombinant proteins were glycosylated. Tunicamycin treatment of insect cells infected with recombinant baculoviruses or wt AcMNPV was conducted to test if the recombinant proteins were N-glycosylated as tunicamycin inhibit N-linked glycosylation. After the treatment, the 29 kDa band of the ORF 2 recombinant protein was disappeared, a 25 kDa appeared and the 27 kDa species remained unchanged. For the ORF 3 recombinant protein, the species of 27–31 and 35–43 kDa were disappeared and the 22–27 kDa bands remained unchanged. The 27 kDa species of ORF 3 recombinant protein became more abundant after tunicamycin treatment. After the N-glycosylation inhibition, the ORF 4 recombinant protein was shown as 15 and 18 kDa species only and the bands of 22–30 kDa were disappeared. The 15 and 18 kDa bands became sharper and darker after the tunicamycin treatment. No signal was detected in extracts from wt AcMNPV infected insect cells.

Immunogenecity of the recombinant proteins. The recombinant proteins of ORFs 2 to 4 products were tested for immunogenecity by immunization of rabbits with lysates of insect cells infected with vAc-P2, vAc-P3 and vAc-P4. The presence of anti-PRRSV antibodies in the rabbit serum samples was detected by ELISA. The average titers of immunized rabbits were 192, 128 and 382 for the groups of vAc-P2, vAc-P3 and vAc-P4 cell lysate respectively (Table 6).

Discussion

The genes of ORFs 2 to 4 of PRRSV were cloned into BEVS and the recombinant proteins were expressed in insect cells. The cloning strategy for ORFs 2 and 3 was much faster than that for ORF 4 as the selection process of recombinant baculovirus was done in *E. Coli* instead of choosing occlusion body-negative plaques on Sf9 cells. Sf9 cells were used for the propagation of baculovirus, and High Five™ cells were used for protein expression as protein yield in High Five™ cells was believed to be higher than that in Sf9 cells (Wickham et al. Biotechnology Progress 8:391–396 (1992) & Davis et al., In Vitro Cell and Developmental Biology 29A: 388–390 (1993)). The High Five™ cells were adapted to serum free medium, which benefits for future protein purification, and can be adapted to suspension culture, which is suitable for large scale industrial production.

The recombinant proteins were shown by IFA to express in insect cells infected with vAc-P2, vAc-P3 and vAc-P4 recombinant viruses. There was weak cytoplasmic fluorescence in vAc-P2 infected cells, strong cytoplasmic fluorescence in vAc-P3 and vAc-P4 infected cells. The reason for the weak fluorescence of vAc-P2 infected cells is not known and could be due to epitope alternation after fixation with methanol. The unfixed and unpermeabilized insect cells were stained at 4 OC to make sure that the pig anti-PRRSV antibody reacted with cell surface proteins only and did not enter into cytoplasm. There was clear cell surface immunofluorescence on the insect cells infected with vAc-P2, vAc-P3 or vAc-P4, which indicates that the recombinant proteins were efficiently processed and transported to cell surface. This result indicates that ORFs 2 to 4 products are membrane-associated proteins, which is consistent with the predictions from sequence studies (Morozov et al., Archives of Virology 140:1313–1319 (1995)). However, it is not clear if these products are also transported to cell surface of PRRSV infected mammalian cells or assembled into virions as surface proteins. Recent report showed that the ORFs 3 and 4 products are viral structural proteins (VAN Nieuwstadt et al, J. Virol. 70:4767–4772 (1996)). Further experiment is needed to investigate the destiny of these proteins.

Immunoblotting results showed that the recombinant proteins were efficiently expressed in insect cells. The ORF 2 product was detected as 27 and 29 kDa species in $M_r$. Tunicamycin treatment eliminated the 29 kDa band and introduced the 25 kDa species with the 27 kDa unchanged, which indicated that the 29 kDa was N-glycosylated. The predicted $M_r$ of PRRSV VR 2385 ORF 2 is 29.5 kDa with two potential glycosylation sites (Morozov et al., 1995). The 25 kDa species may be the core protein of ORF 2 if the 37–38 signal sequence (Meulenberg et al., Virology 192:62–72 (1995)) are removed in the mature protein. The 4 kDa difference between the 29 and 25 kDa bands may be due to carbohydrate structures as one glycosyl moiety has a $M_r$ of about 2–3 kDa (Trimble et al., J. Biol. Chem. 250:2562–2567 (1983)). The 27 kDa species was not sensitive to the tunicamycin treatment and may be modified by 0-linked glycosylation or other post-translational modifications.

The ORF 3 product in insect cells was shown as 22–43 kDa multi-band species detected by immunoblotting. The 28–43 kDa species were eliminated by tunicamycin treatment of vAc-P3 infected insect cells, which indicated that they were N-linked glycoproteins and the multi-bands were due to differential glycosylation. The predicted $M_r$ of PRRSV VR 2385 ORF 3 product is 28.7 kDa (about 2 kDa less than the counterpart of LV) with 7 potential N-linked glycosylation sites (Morozov et al., 1995). The 27 kDa species of ORF 3 recombinant protein may be the core protein because it became more abundant after tunicamycin treatment and because a 27 kDa band appeared and a 45 kDa band disappeared after endoglycosidase F treatment of purified PRRSV virion (data not shown). The species smaller than 27 kDa may be truncated proteins or products of proteolysis. The 27–43 kDa bands in nontreated sample are hard to differentiate into individual bands, which may be due to overloading or partial proteolysis. The 43 kDa species may be the fully glycosylated product as there are 7 N-linked glycosylation sites and about 2–3 kDa are counted for each glycosyl moiety (Trimble et al., 1983). The recent report showed that ORF 3 of LV encodes a 45–50 kDa structural protein and that recombinant proteins of ORF 3 in insect cells were detected as 28–44 kDa in M, by radioimmunoprecipitation (VAN Nieuwstadt et al., 1996). The 28 kDa species was found as the core protein of LV ORF 3 product. It seems there is difference in Mr of recombinant proteins from ORF 3 of US PRRSV and LV, which may be due to the different expression system used or the difference in this gene between the two isolates. Another report showed that the recombinant fusion protein of carboxyterminal 199 amino acids of LV ORF 3 expressed in baculovirus was not N-glycosylated (Katz et al., Vet. Microbiol. 44:65–76 (1995)), which demonstrates the diversity of expressed products from the same gene.

The ORF 4 product in insect cells was detected as 15–30 kDa multi-band species. After tunicamycin treatment the 22–30 kDa bands were eliminated and the 15, 18 kDa bands remained unchanged, which indicated that the 22–30 kDa species were N glycosylated to various degrees. The ORF 4 of PRRSV VR 2385 was predicted to encode a 19.5 kDa protein with 4 potential N glycosylation sites (Morozov et al., 1995). The 15 kDa species of ORF 4 product may be the core protein and the 18 kDa band may be the core protein plus 0-linked glycosyl moiety or other modifications. It was reported that LV ORF 4 encoded a 31–35 kDa structural protein and that the recombinant protein of ORF 4 expressed in insect cells was detected as 20–29 kDa species with a 17 kDa core protein (VAN Nieuwstadt et al., 1996). Again, the reason for the difference in Mr may be due to the cloned gene's difference and the different expression systems. Another report demonstrated the difference by showing that ORF 4 is not a well conserved region (Kwang et al., J. Vet. Diag. Invest. 6:293–296 (1994)).

The immunization of rabbits with the recombinant proteins showed that they had induced anti-PRRSV antibodies. This result indicates that these recombinant proteins may have the similar immunogenecity as their native counterparts in PRRSV infected mammalian cells.

This study showed that the ORFs 2 to 4 of PRRSV VR 2385 were expressed in BEVS and detected both in cytoplasm and on cell surface of insect cells. The recombinant proteins of ORFs 2 to 4 were N-linked glycoproteins with differential glycosylation. The purified PRRSV virions were analyzed as the same time and showed 4 bands in immunoblotting. But due to lack of oligoclonal or monoclonal antibodies it is hard to tell if any of ORFs 2 to 4 products was detected in the purified virions. The reaction of pig anti-PRRSV serum with the recombinant proteins indicated that the native counterpart of these proteins induced immune response in natural host. The induction of anti-PRRSV antibodies in rabbits indicated that these recombinant proteins had similar immunogenecity as the native ORFs 2 to 4 products in PRRSV infected natural host.

TABLE 6

Rabbit antiserum titers tested with ELISA

| Groups of insect cells infected with | Number of rabbits | Means of titers* |
|---|---|---|
| vAc-P2 | 2 | 192 |
| vAc-P3 | 2 | 128 |
| vAc-P4 | 2 | 384 |

*Titers were expressed as the reciprocals of the highest dilutions shown positive in ELISA.

EXAMPLE 5

Cells and viruses. ATCC CRL11171 cells were used to propagate PRRSV (Meng et al., 1994 and 1996; Halbur et al., 1995). *Spodoptera frugiperda* clone 9 (Sf9) and High Five™ (Invitrogen) insect cells were used for propagation of baculovirus. PRRSV isolate VR 2385 (Meng et al., 1994 and 1996) was used for gene amplification and cloning into BEVS. PRRSV virions were purified as previously described (Meng et al., 1994). The baculovirus strain Autographa california multinuclear polyhedrosis virus (AcMNPV) was used as parent virus for recombinant virus construction.

Construction of AcMNPV recombinant transfer vector. The nucleic acid sequence of the ORFs 5–7 of PRRSV VR2385 was previously described (Meng et al. 1994). Construction of the baculovirus transfer vectors containing the PRRSV ORFs 5 to 7 separately was done with the strategies as described previously (Bream et al. 1993). Briefly, PRRSV ORFs 5 to 7 genes were PCR amplified separately from the template pPSP.PRRSV2-7 plasmid with primers containing restriction sites of BamHI and EcoRI. The forward primer for ORF5 was 5'TGCCAGGATCCGT-GTTTAAATATGTTGGGG3' (SEQ ID NO:98) and the reverse primer was 5'CGTGGAATTCATAGAAAACGC-CAAGAGCAC3' (SEQ ID NO 98). The forward primer for ORF6 was 5'GGGGATCCAGAGTTTCAGCGG3' (SEQ ID NO 100) and the reverse primer was 5'GGGAATTCTG-GCACAGCTGATTGAC3' (SEQ ID NO 101). The forward primer for ORF7 was 5'GGGGATCCTTCTTAAATAT-GCC3' and the reverse primer was 5'GGGAATTCAC-CACGCATTC3' (SEQ ID NO 103). The fragments amplified were cut with BamHI and EcoRI, isolated and ligated into vector PVL1393 (Invitrogen) which was also cut with BamHI and EcoRI to insure correct orientations. The inserted genes were under control of the polyhedrin gene promotor (O'Reilly et al., 1992) and verified with restriction enzyme digestion and PCR amplification. The recombinant vectors containing the ORFs 5 to 7 genes separately were isolated, pPSP.Ac-E for ORF5, pPSP.Ac-M for ORF6 and pPSP.Ac-N for ORF7 transfer vectors. Transfection and selection of recombinant viruses. Sf9 insect cells were cotransfected with linearized AcMNPV DNA (Invitrogen) and recombinant plasmid DNA of pPSP.Ac-E, pPSP.Ac-M, and pPSP.Ac-N respectively as per manufacturer's instructions. Putative recombinant viruses were selected following three-round of purification of occlusion-negative plaques. The inserted genes in the recombinant viruses were verified with hybridization and PCR amplification (O'Reilly et al., 1992). Four recombinants were selected for each of the 3 strains of recombinant viruses and were found to be similar in immunofluorescence assays using pig anti-PRRSV serum. One recombinant virus was chosen arbitrarily from each strain and designated as vAc-E1 for recombinant virus containing ORF5, vAc-M1 for that with ORF6, and vAc-N1 for that with ORF7.

Immunoblotting. Western immunoblot analyses were carried out as described previously (Harlow and Lane, 1988). Whole proteins from infected insect cells, purified PRRSV or normal cells were used as samples. Proteins were separated with SDS-PAGE and transferred to nitrocellulose membrane by electrophoresis. The nitrocellulose membrane was blocked with 3% BSA and reacted with pig anti-PRRSV serum for 1 hour at room temperature. Bound antibodies were detected by incubation with goat anti-pig IgG peroxidase conjugate, followed by color development with 4-chloro-1-naphthol substrate.

Tunicamycin treatment. Infected High Five™ cells were incubated with 5 $\mu$g/ml tunicamycin in cell-culture medium from 0 to 72 hr post infection and harvested for SDS-PAGE (O'Reilly et al., 1992).

Cleavage with glycosidases. Endoglycosidase F/N-glycosidase F mixture (PNGase F) and endoglycosidase H (Boehringer-Mannheim Biochemicals) were used to treat lysates from infected High Five™ cells (0.1 PFU/cell; 72 hr post infection) in the case of recombinant proteins or purified PRRSV as per manufacturer's instructions. Briefly, $10^5$ cells were laced with 30 $\mu$g lysis buffer. Then 10 $\mu$g of cell lysates was digested with PNGase F, endoglycosidase H or kept untreated and used as non-treated control. The samples were incubated at 37° C. for 24 hrs before analysis on SDS-PAGE.

Radioimmunoprecipitation (RIP). High Five™ cells infected with recombinant baculovirus or wild type (wt) AcMNPV and uninfected High Five™ cells were washed once with methionine-free medium and starved for one hour at 48 hr post-infection. Then 50 $\mu$g/ml Tran$^{35}$S-label (methionine and cystine) (Amersham Life Science Inc.) in methionine-free medium was added to the infected cells. Three hours later the cells were rinsed with PBS and laced in RIPA lysis buffer (10 mM Tris-HCI, pH8.0; 1 mM EDTA; 150 mM NaCl; 1% NP40; 1% sodium deoxycholate; 0.1% SDS). Immunoprecipitation and gel electrophoresis were performed as described previously (Hutchinson et al., J. Virol. 66:2240–2250 (1992).

Indirect Immunofluorescence Assay (IFA). IFA was conducted as previously described (O'Reilly et al., 1992). Monolayer of High Five™ cells were inoculated with wt AcMNPV or recombinant baculoviruses, incubated for 72 hrs and fixed to detect all recombinant protein expression with pig anti-PRRSV serum. The inoculated insect cells were also examined for the presence of cell surface proteins. Unfixed and unpermeabilized cells were reacted with the pig antiserum at 4° C. for 1 hr, incubated with fluorescein-labeled goat anti-pig IgG conjugate for 1 more hr at 4° C. and then observed under fluorescent microscope.

Immunogenecity of the recombinant proteins. Twelve-week old rabbits were injected intramuscularly and subcutaneouslly with lysates of insect cells infected with vAc-El, vAc-Ml and vAc-Nl. Two rabbits were immunized for each of E, M, and N recombinant proteins. Two booster injections were given in an interval of three weeks. The injection dose was cell lysates from $2\times10^6$ insect cells. Blood was collected 10 days after the second booster injection. Antibodies were tested with indirect ELISA. Purified PRRSV virions were sonicated and used to coat 96-well plates and goat anti-rabbit IgG peroxidase conjugate was used to detect anti-PRRSV antibodies in rabbit serum samples. Pre-immune rabbit serum was used as negative control. Substrate 2,2'-azino-bis(3-ethylbenzthiazoline-6-sulfonic acid) (ABTS) was used to reveal specific reactions.

Results

Confirmation for the presence of PRRSV gene in recombinant baculovirus. Hybridization and PCR amplification were performed to verify the presence of the cloned genes in recombinant baculovirus. Hybridization of probes from the PRRSV genes with recombinant baculovirus showed that the PRRSV genes were present in the recombinant baculovirus. PCR amplification with specific primers from PRRSV genes showed a single band from the recombinant virus and absent from the wt AcMNPV (results not shown). These tests confirmed that the recombinant baculoviruses contain the PRRSV genes ORFs 5 to 7.

Surface immunofluorescence of recombinant viruses vAc-E1 and vAc-M1, but not vAc-N1. High Five™ cells infected with vAc-E1, vAc-M1, vAc-N1, and wt AcMNPV were examined for the presence of total expressed protein and cell surface expression. There was weak cytoplasmic fluorescence in vAc-E1 and vAc-M1-infected cells. In contrast, there was intense cytoplasmic fluorescence in vAc-N1-infected insect cells and no fluorescence in wt AcMNPV infected cells. Clear cell surface immunofluorescence was detected in vAc-E1 and vAc-M1 infected insect cells. However, there was no surface immunofluorescence in insect cells infected with vAc-N 1 or wt AcMNPV. Also, in the absence of antibody insect cells infected with the recombinant viruses did not show any fluorescence (data not shown).

Analysis of ORFs 5–7 products expressed in insect cells. To analyze the expression of the expected proteins in insect cells, confluent monolayers of High Five™ cells were infected at a multiplicity of infection of 0.1 PFU/cell with vAc-E1, vAc-M1 and vAc-N1 respectively and incubated for 72 hr. Total protein samples were run on SDS-PAGE and analyzed by western-blotting using pig anti-PRRSV serum. The recombinant protein E expressed in insect cells was detected as multi-band species of 16,18, 20, 24, and 26 kDa. The E expressed in insect cells showed more diversity and lower $M_r$ compared with the native E, 26 kDa species, in the purified PRRSV. The M expressed in insect cells was detected as a 19 kDa band, which corresponded to the native M in purified PRRSV. The N expressed in insect cells was detected as a 15 kDa band, which also corresponded to the native N in the purified PRRSV. These specific bands were not detected in normal insect cells (results not shown) and those infected with wt AcMNPV. Purified PRRS virions were analyzed in the same gel. There were at least five bands: 15, 19, 24, 26–30 and 45 kDa. The specific bands detected in purified PRRS virions were not observed in normal mammalian cell controls.

Immunoprecipitation was also carried out to confirm the expression of E, M and N in insect cells. Pig anti-PRRSV serum was used to react with the recombinant proteins expressed in insect cells and protein A beads were used to precipitate the antigen-antibody complex. A 19 kDa band was detected in the vAc-M1 infected cells. The $M_r$ of protein detected in insect cells infected with vAc-N1 was a 15 kDa band. In preliminary studies, only some weak bands were observed in RIP in insect cells infected with vAc-E1 (result not shown).

Glycosylation analysis of baculovirus expressed E, M, and N. To determine if the E, M, and N expressed in insect cells underwent N-glycosylation, the insect cells infected with the recombinant baculoviruses were treated with tunicamycin to inhibit N-linked glycosylation. After tunicamycin treatment, the 20–26 kDa species were not detected in insect cells infected with the vAc-E1, while the 16 and 18 kDa bands became more abundant. In the cells infected with vAc-M1 and vAc-N1, no changes in $M_r$ of M and N proteins were detected after the tunicamycin treatment.

To further investigate the glycosylation of recombinant E, M and N expressed in insect cells, proteins were treated with endoglycosidases F and H and analyzed. Following treatment, the 15 kDa band of N remained unchanged as compared with the 15 kDa band in the purified PRRS virus. No change in the 19 kDa band of M was detected after the enzyme digestion (result not shown). In the PNGase F treated purified PRRSV, at least two bands, 26 and 45 kDa, disappeared and two more bands, 16 and 27 kDa, appeared compared to the non-treated PRRSV. In the endoglycosidase H were treated PRRSV, less amount of the species around 28 kDa was detected while other bands remained unchanged. The result that 15 and 19 kDa bands remained unchanged after PNGase F and H treatment was consistent with that of the tunicamycin treatment of insect cells infected with vAc-M1 and vAc-N1.

Immunogenecity of the recombinant proteins. The recombinant proteins E, M, and N were tested for immunogenecity by immunization of rabbits with lysates of insect cells infected with vAc-E1, vAc-M1 and vAc-N1. Then ELISA was carried out to test for the presence of anti-PRRSV antibodies in the rabbit serum samples. The average titers of E, M and N immunized rabbits were 384, 320 and 2,056 respectively (Table 7).

Discussion

Recombinant baculoviruses containing the genes E, M, and N of PRRSV were constructed to express E, M, and N in insect cells. Sf9 cells were used for the propagation of baculovirus, and High Five™ cells were used for protein expression as protein yield in High Five™ cells was believed to be higher than that in Sf9 cells (Wickham et al., 1992 and Davis et al., 1993).

Immunofluorescence analysis showed that E, M and N were expressed in insect cells infected with recombinant viruses containing those genes and showed that E and M were transported to the cell surface in insect cells. This result indicates that E and M expressed in insect cells are membrane-associated proteins and efficiently processed in post-translational modification. The reason for low intensity of cytoplasmic immunofluorescence of E and M in insect cells is unclear. It may be due to the epitope loss or modification after fixation of the infected insect cells. In insect cells infected with vAc-N1, only intense cytoplasmic immunofluorescence was observed and no surface fluorescence was detected. This result indicated that baculovirus expressed N was not transported to cell surface but located in the cytosol. This characteristic is consistent with its nature as a very hydrophilic nucleocapsid protein as predicated from sequence studies (Meng et al., 1994).

The recombinant E protein showed multi-bands in immunoblotting, the bands with $M_r$ smaller than 26 kDa were not found in the purified PRRSV. The E expressed in insect cells showed more diversity and lower $M_r$ compared with the native E, 26 kDa species, in the purified PRRSV. The multi-bands may be due to differential glycosylation in insect cells during post-translational modification. Tunicamycin treatment eliminated the 20–26 kDa bands and increased the intensity of the 16 kDa band. The presence of the 18 kDa band after treatment could be due to 0-linked glycosylation, phosphorylation or other post-translational modifications. The 20–26 bands represent those of differential N-glycosylated species of E in insect cells. The 16 kDa band may be the non-glycosylated leader-free core protein. Preliminary studies of PNGase F and endoglycosidase H treatment of recombinant protein E showed that it underwent complex glycosylation. The recombinant M and N did not undergo N-linked glycosylation as both the tunicamycin and PNGase F and endoglycosidase H treatments did not alter the mobilities of the 19 and 15 kDa bands. These results indicate that the recombinant protein E of 20–26 kDa is N-glycosylated, and that the recombinant M and N proteins expressed in insect cells are not N-glycosylated. The changes in mobility after tunicamycin treatment were consistent with the presence of two N-linked glycosylation sites in the E polypeptide as determined from sequence studies (Meng et al., 1994). However, sequence studies indicated that there are 2 and 1 potential N-linked glycosylation sites in the M and N polypeptides respectively. In the baculovirus expressed M and N, there was no N-linked glycosylation detected. Compared with the native counterparts, the recombinant proteins in insect cells were much more abundant as seen from the immunoblot (the loading amount of the recombinant proteins was about one percent of the PRRSV lane). However, it is difficult to measure the difference without oligoclonal or monoclonal antibodies.

For the purified PRRSV, there are at least five bands: 15, 19, 24, 26–30 and 45 kDa. This result is consistent with the previous reports that there are at least three structural proteins in the PRRSV virion (Conzelmann et al., Virology 193:329–339 (1993); Nelson et al., J. Clin. Microbiol. 31:3184–3189 (1994) and Mardassi et al., Arch. Virol. 140:1405–1418 (1994)). The 45 kDa band in the purified PRRSV may be the ORF3 product as reported (Kapur et al., J. Gen. Virol. 77:1271–1276 (1996)). The nature of the 24, 27–30 kDa species can not be figured out. After treatment with PNGase F and endoglycosidase H, the band pattern changed for the PRRSV sample. In the PNGase F treated PRRSV, the 16-kDa band may represent the non-glycosylated leader-removed core protein of E, the 27-kDa band may indicate another structural protein of PRRSV besides E, M and N. However, the nature of these bands needs to be determined by oligoclonal or monoclonal antibodies.

The results from rabbit immunization test indicated that the antibodies generated from the immunization of rabbits with the recombinant proteins could recognize the native PRRSV viral antigens. The recombinant proteins showed the same antigenicity as their native counterparts in PRRSV infected mammalian cells, especially the recombinant N which induced higher antibody titers in rabbits than did E and M.

TABLE 7

Rabbit antiserum titers tested with ELISA

| Groups of insect cells infected with | Number of rabbits | Means of titers* |
|---|---|---|
| vAc-E1 | 2 | 384 |
| vAc-M1 | 2 | 320 |
| vAc-N1 | 2 | 2056 |

*Titers were expressed as the reciprocals of the highest dilutions of serum that showed positive reading.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A composition comprising a purified polynucleic acid encoding at least one polypeptide selected from the group consisting of:

proteins encoded by one or more open reading frames (ORF's) of an Iowa strain of porcine reproductive and respiratory syndrome virus (PRRSV);

proteins with at least 99% but less than 100% amino acid homology with proteins encoded by one or more of ORFs 2 of VR 2385 and VR 2474, ORF 3 of VR 2429, and ORFs 4 of VR 2429 and ISU 1894;

proteins with at least 98% but less than 100% amino acid homology with proteins encoded by one or more of ORF 2 of VR 2430 and ORF 5 of VR 2429;

proteins with at least 97% but less than 100% amino acid homology with proteins encoded by one or more of ORF 2 of ISU 1894, ORFs 3 of VR 2474 and ISU 1894, ORF 4 of VR 2474 and ORF 5 of ISU 1894;

proteins with at least 96% but less than 100% amino acid homology with the protein encoded by ORF 4 of VR 2430;

proteins with at least 95% but less than 100% amino acid homology with proteins encoded by one or more of ORF 3 of VR 2430, ORF 4 VR 2385, and ORF 5 of VR 2474;

proteins with at least 94% but less than 100% amino acid homology with the protein encoded by ORF 2 of VR 2431;

proteins with at least 93% but less than 100% amino acid homology with the protein encoded by ORF 3 of VR 2431;

proteins with at least 92% but less than 100% amino acid homology with the proteins encoded by one or more of ORF 3 of VR 2385 and ORF 5 of VR 2431;

proteins with at least 90% but less than 100% amino acid homology with those encoded by one or more of ORFs 5 of VR 2385 and VR 2430;

proteins with at least 88% but less than 100% amino acid homology with the protein encoded by ORF 3 of VR 2431;

proteins with at least 97% but less than 100% amino acid homology with proteins encoded by one or both of ORF 6 and ORF 7 of an Iowa strain of PRRSV;

and combinations thereof.

2. The composition of claim 1, wherein said polynucleic acid has a sequence selected from the group consisting of the formulas (I), (II), (III) and (IV):

$$5'-\alpha-\beta-3' \qquad (I)$$

$$5'-\alpha-\beta-\gamma-3' \qquad (II)$$

$$5'-\alpha-\beta-\delta-\gamma-3' \qquad (III)$$

$$5'-\alpha-\beta-\delta-\gamma-3' \qquad (IV)$$

wherein:

$\alpha$ encodes at least one polypeptide, low-virulence mutant thereof, or antigenic or low-virulence fragment thereof encoded by a polynucleotide selected from the group consisting of ORFs 2, 3 and 4 of an Iowa strain of PRRSV;

$\beta$ is at least one copy of an ORF 5 from an Iowa strain of PRRSV or one or more hypervariable regions thereof;

$\gamma$ encodes at least one polypeptide encoded by a polynucleotide selected from the group consisting of ORF 6 and ORF 7 of an Iowa strain of PRRSV; and $\delta$ is either a covalent bond or a linking polynucleic acid which does not materially affect transcription and/or translation of the polynucleic acid.

3. The composition of claim 1, wherein said polynucleotide encodes at least one hypervariable region of a protein encoded by an ORF 5 of an Iowa strain of PRRSV.

4. The composition of claim 1, wherein said polypeptide is selected from the group consisting of proteins with at least 97% amino acid homology with proteins encoded by ORF 6 of VR 2385, VR 2429 (ISU-22), ISU-79 and VR 2431 (ISU3927); proteins with at least 90% amino acid homology with proteins encoded by ORFs 5 of VR 2385 and VR 2430; proteins with at least 94% amino acid homology with the protein encoded by ORF 2, at least 88% amino acid homology with the protein encoded by ORF 3, and at least 93% amino acid homology with the protein encoded by ORF 4 of VR 2431.

5. The composition of claim 4, wherein said polypeptide is encoded by a polynucleic acid selected from the group consisting of ORF 2 of VR2385, ORF 3 of VR2385, ORF 4 of VR2385, ORF 5 of VR2385, ORF 6 of VR2385, ORF 7 of VR2385, ORF 2 of VR2431, ORF 3 of VR2431, ORF 4 of VR2431, ORF 5 of VR2431, ORF 6 of VR2431, and ORF 7 of VR2431.

6. A composition comprising a polynucleic acid having the formula (V):

$$5'-\epsilon-\zeta-\iota-\kappa-\xi-3' \qquad (V):$$

where:

$\kappa$ is a polynucleotide comprising one or more polynucleotides selected from the group consisting of (a) polynucleotide encoding at least one polypeptide encoded by one or more of ORFs 2, 3 and 4 of an Iowa strain of PRRSV; (b) polynucleotide encoding at least one polypeptide encoded by an ORF 5 from an Iowa strain of PRRSV; (c) polynucleotide encoding at least one polypeptide encoded by an ORF 6 or ORF 7 of an Iowa strain of PRRSV; and (d) operationally linked combinations thereof; and wherein $\kappa$ optionally further comprises a polynucleic acid encoding a conventional marker or a reporter gene;

$\epsilon$, which is optionally present, is a 5'-terminal polynucleotide sequence which provides a means for operationally expressing the polynucleotide $\epsilon$;

$\zeta$ is a polynucleotide of the formula KTVACC, where K is T, G or U, and V is A, G or C;

$\iota$ is a polynucleotide not more than 130 nucleotides in length;

and $\xi$, which is optionally present and when present may be operationally linked to $\xi$, and is a 3'-terminal polynucleotide sequence which does not suppress the operational expression of the polynucleotide $\epsilon$.

* * * * *